United States Patent
Bonrath et al.

(10) Patent No.: US 9,452,961 B2
(45) Date of Patent: *Sep. 27, 2016

(54) (6R,10R)-6,10,14-TRIMETYLPENTADECAN-2-ONE PREPARED FROM 6,10-DIMETYLUNDEC-5-EN-2-ONE OR 6,10-DIMETYLUNDECA-5,9-DIEN-2-ONE

(71) Applicant: DSM IP ASSETS B.V., Heerlen (NL)

(72) Inventors: Werner Bonrath, Kaiseraugst (CH); Thomas Netscher, Kaiseraugst (CH); Jonathan Alan Medlock, Kaiseraugst (CH); René Tobias Stemmler, Kaiseraugst (CH); Johannes Tschumi, Baltschieder (CH); Gerardus Karel Maria Verzijl, Geleen (NL); Andreas Hendrikus Maria De Vries, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,303

(22) PCT Filed: Dec. 18, 2013

(86) PCT No.: PCT/EP2013/077187
§ 371 (c)(1),
(2) Date: Jun. 15, 2015

(87) PCT Pub. No.: WO2014/096065
PCT Pub. Date: Jun. 26, 2014

(65) Prior Publication Data
US 2015/0329457 A1    Nov. 19, 2015

(30) Foreign Application Priority Data
Dec. 18, 2012 (EP) .................................... 12197835

(51) Int. Cl.
| | |
|---|---|
| C07C 45/53 | (2006.01) |
| C07C 49/00 | (2006.01) |
| C07C 29/00 | (2006.01) |
| C07D 309/00 | (2006.01) |
| C07C 29/17 | (2006.01) |
| C07C 29/44 | (2006.01) |
| C07C 45/51 | (2006.01) |
| C07C 45/59 | (2006.01) |
| C07C 45/62 | (2006.01) |
| C07C 45/67 | (2006.01) |
| C07C 45/71 | (2006.01) |
| C07C 45/90 | (2006.01) |
| C07F 9/50 | (2006.01) |
| C07F 15/00 | (2006.01) |
| C07D 311/58 | (2006.01) |
| C07D 319/06 | (2006.01) |

(52) U.S. Cl.
CPC ............... *C07C 29/17* (2013.01); *C07C 29/44* (2013.01); *C07C 45/511* (2013.01); *C07C 45/59* (2013.01); *C07C 45/62* (2013.01); *C07C 45/67* (2013.01); *C07C 45/71* (2013.01); *C07C 45/90* (2013.01); *C07D 311/58* (2013.01); *C07D 319/06* (2013.01); *C07F 9/5045* (2013.01); *C07F 15/0033* (2013.01); *C07B 2200/07* (2013.01)

(58) Field of Classification Search
CPC ....... C07C 45/53; C07C 45/62; C07C 45/67; C07C 45/71; C07C 49/203; C07C 29/141; C07D 309/06
USPC ........................ 568/409, 880, 909.5; 549/356
See application file for complete search history.

(56) References Cited

U.S. PATENT DOCUMENTS

| | | | |
|---|---|---|---|
| 4,028,385 A | 6/1977 | Fujita et al. | |
| 4,292,459 A | 9/1981 | Cardenas et al. | |
| 5,600,015 A | 2/1997 | Broger et al. | |
| 5,955,636 A | 9/1999 | Kido et al. | |
| 2008/0039638 A1 | 2/2008 | Bonrath et al. | |

FOREIGN PATENT DOCUMENTS

CN    200580044518.4    12/2007

OTHER PUBLICATIONS

International Search Report for PCT/EP2013/077187 mailed Mar. 25, 2014, four pages.
Kimel et al., "Synthesis of Pseudoionone Homologs and Related Compounds", *The Journal or Organic Chemistry*, vol. 22, No. 12, Dec. 1, 1957, pp. 1611-1618.
Odinokov et al., "New Approach to the Synthesis of (2RS,4"R,8"R)-[alpha]-Tocopherol (Vitamin E)", *Doklady Chemistry*, vol. 380, No. 1-3, Sep. 1, 2001, pp. 255-257.
CN Appln. No. 201380065785.4, Official Action (Feb. 14, 2016).

*Primary Examiner* — Sikarl Witherspoon
(74) *Attorney, Agent, or Firm* — Nixon & Vanderhye P.C.

(57) ABSTRACT

The present invention relates to a process of manufacturing (6R,10R)-6,10,14-trimetylpentadecan-2-one in a multistep synthesis from 6,10-dimetylundec-5-en-2-one or 6,10-dimetylundeca-5,9-dien-2-one. The process is very advantageous in that it forms in an efficient way the desired chiral product from a mixture of stereoisomers of the starting product.

17 Claims, 7 Drawing Sheets

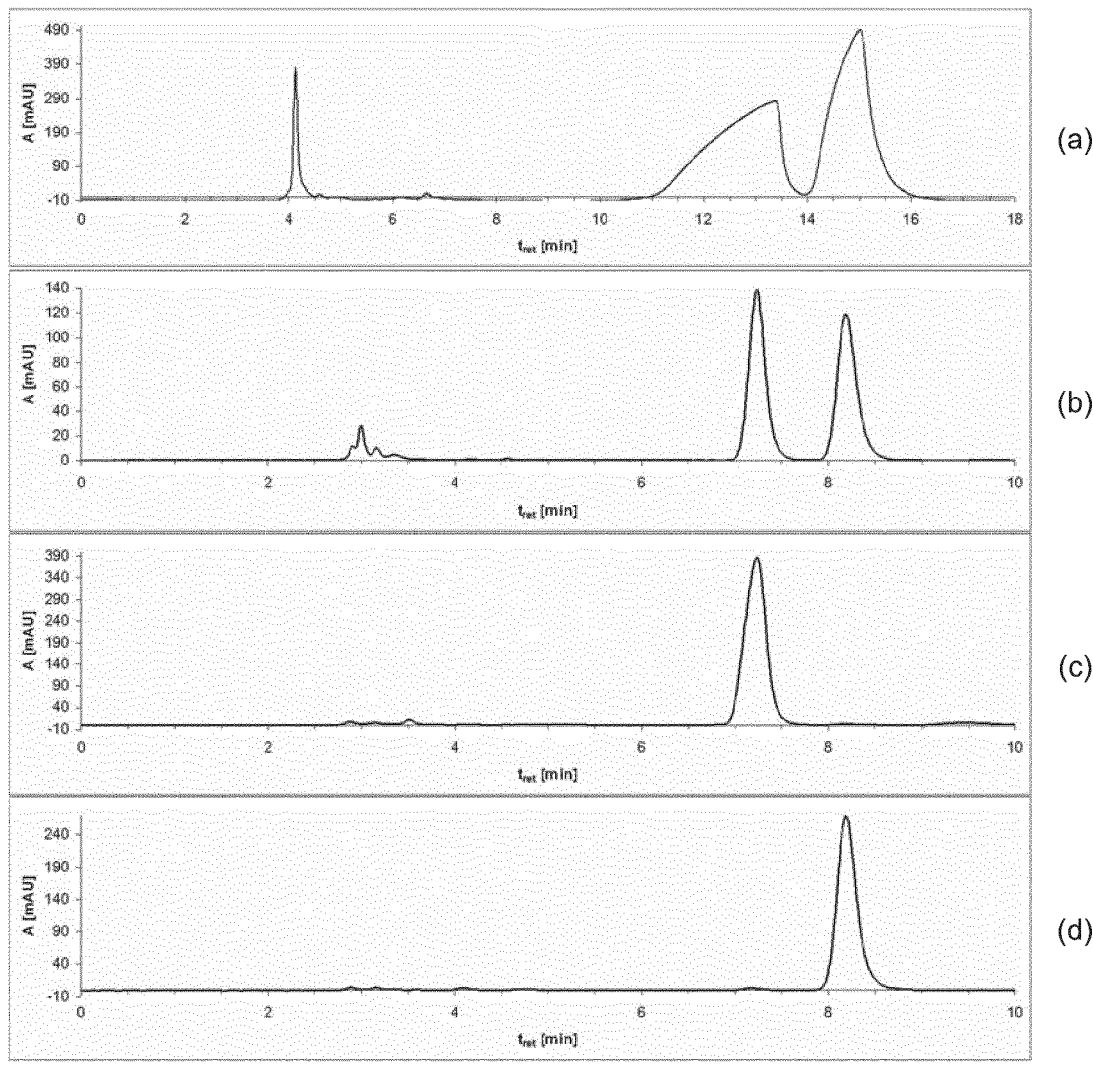
Fig. 7 Chromatograms of separation of 2-*ambo*-α-tocopherol

(6R,10R)-6,10,14-TRIMETYLPENTADECAN-2-ONE PREPARED FROM 6,10-DIMETYLUNDEC-5-EN-2-ONE OR 6,10-DIMETYLUNDECA-5,9-DIEN-2-ONE

This application is the U.S. national phase of International Application No. PCT/EP2013/077187 filed 18 Dec. 2013 which designated the U.S. and claims priority to EP Patent Application No. 12197835.7 filed 18 Dec. 2012, the entire contents of each of which are hereby incorporated by reference.

TECHNICAL FIELD

The present invention relates to the field of (6R,10R)-6,10,14-trimethylpentadecan-2-one and the reaction products thereof.

BACKGROUND OF THE INVENTION (6R,10R)-6,10,14-Trimethylpentadecan-2-one is an important intermediate, particularly for the synthesis of (R,R)-isophytol [=(3RS,7R,11R)-3,7,11,15-tetramethylhexadec-1-en-3-ol], (R,R)-phytol and tocopherols.

Isophytol, phytol and tocopherols are chiral substances, the latter two of which occur in nature in the form of the "all-R" stereoisomer. Phytol contains 2 stereocentres and in addition a trisubstituted carbon-carbon double bond which gives rise to E/Z-steroisomers, while isophytol and tocopherols have 3 stereocentres. Therefore, there are multiple isomers.

It has been shown that of the naturally occurring stereoisomers of tocopherols, (2R,4'R,8'R)-tocopherols, particularly (2R,4'R,8'R)-α-tocopherol, have the highest bioactivity (biopotency).

As natural sources of (2R,4'R,8'R)-tocopherols and (R,R)-phytol, however, are very limited, the market has a strong need for an effective synthesis of (2R,4'R,8'R)-tocopherols and (R,R)-isophytol and (6R,10R)-6,10,14-trimethylpentadecan-2-one, the starting material of these products, which is useful for industrial scale application.

As, furthermore, higher bioactivity (biopotency) has been shown, for example by H. Weiser et al. in *J. Nutr.* 1996, 126(10), 2539-49, to occur in general by tocopherols having the R-configuration at the chiral centre situated next to the ether oxygen atom in the ring of the molecule (i.e. 2R-configuration), as compared to the corresponding isomers having S-configuration, there is a strong need for an effective and industrial scale synthesis of (2R,4'R,8'R)-tocopherols, particularly (2R,4'R,8'R)-alpha-tocopherol.

SUMMARY OF THE INVENTION

Therefore, the problem to be solved by the present invention is to offer a process for the manufacturing (6R,10R)-6,10,14-trimethylpentadecan-2-one.

Surprisingly, it has been found that the process according to claim 1 is able to solve this problem. It has been shown that it is possible to obtain one specific isomer of interest from a mixture of isomers of starting material, i.e. a mixture of (E)-6,10-dimethylundec-5-en-2-one and (Z)-6,10-dimethylundec-5-en-2-one or a mixture of (E)-6,10-dimethylundeca-5,9-dien-2-one and (Z)-6,10-dimethylundeca-5,9-dien-2-one.

Preferred embodiments of the inventions allow making use of the non-desired isomers, by using a cis/trans-isomerization. The asymmetric hydrogenation, which is one of the key elements of this invention, can be improved in quality and speed by ketalization of the ketones to be asymmetrically hydrogenated as well as by the use of specific additives.

The process of the invention allows the production of the target molecules efficiently in a high quality from isomeric mixtures, allowing it to be used for industrial scale production. The process is very advantageous in that it forms the desired chiral product from a mixture of stereoisomers of the starting product in an efficient way.

Further aspects of the invention are subject of further independent claims. Particularly preferred embodiments are subject of dependent claims.

BRIEF DESCRIPTION OF THE DRAWINGS

FIG. 7 shows chromatograms for the (2-ambo)-α-tocopherol of experiment E7.

DETAILED DESCRIPTION OF THE INVENTION

Figure 1:
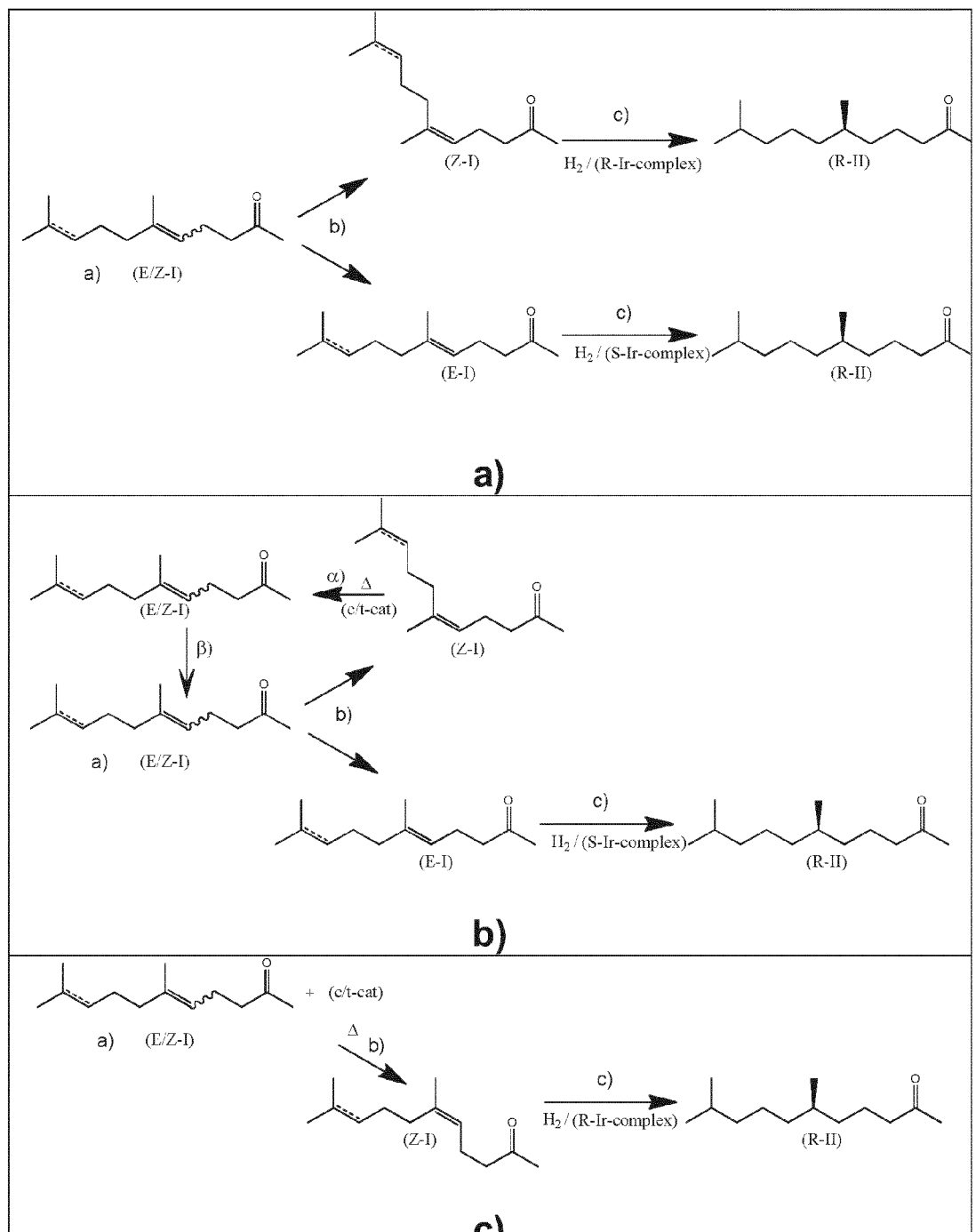
FIGS. 1 to 3 show subsequent steps from both 6,10-dimethylundec-5-en-2-one and 6,10-dimethylundeca-5,9-dien-2-one to (6R,10R)-6,10,14-trimethylpentadecan-2-one.

In a first aspect the present invention relates to a process of manufacturing (6R,10R)-6,10,14-trimethylpentadecan-2-one in a multistep synthesis from 6,10-dimethylundec-5-en-2-one or 6,10-dimethylundeca-5,9-dien-2-one comprising the steps a) providing a mixture of (E)-6,10-dimethylundec-5-en-2-one and (Z)-6,10-dimethylundec-5-en-2-one or a mixture of (E)-6,10-dimethylundeca-5,9-dien-2-one and (Z)-6,10-dimethylundeca-5,9-dien-2-one;

b) separating one isomer of 6,10-dimethylundec-5-en-2-one or of 6,10-dimethylundeca-5,9-dien-2-one from the mixture of step a)

c) asymmetric hydrogenation using molecular hydrogen in the presence of achiral iridium complex and yielding (R)-6,10-dimethylundecan-2-one;

d) chemically transforming (R)-6,10-dimethylundecan-2-one to a mixture of (R,E)-6,10,14-trimethylpentadec-5-en-2-one and (R,Z)-6,10,14-trimethylpentadec-5-en-2-one;

e) separating one isomer of (R)-6,10,14-trimethylpentadec-5-en-2-one from the mixture obtained in step d)

f) asymmetric hydrogenation using molecular hydrogen in the presence of a chiral iridium complex and yielding (6R,10R)-6,10,14-trimethylpentadecan-2-one;

wherein the steps a)-f) are in the order a, b, c, d, e, f.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

A "phenolic alcohol" means in this document an alcohol which has a hydroxyl group which is bound directly to an aromatic group.

The term "(R,R)-isophytol" used in this document means (3RS,7R,11R)-3,7,11,15-tetramethylhexadec-1-en-3-ol).

The term "(R,R)-phytol" used in this document means (2E,7R,11R)-3,7,11,15-tetramethyl-2-hexadecen-1-ol).

Substance names starting with "poly" such as polythiol as used in the present document refer to substances formally containing two or more of the corresponding functional groups per molecule.

The term "stereogenic centre" as used in this document is an atom, bearing groups such that interchanging of any two of the groups leads to a stereoisomer. Stereoisomers are isomeric molecules that have the same molecular formula and sequence of bonded atoms (constitution), but that differ in the three-dimensional orientations of their atoms in space.

The configuration at a stereogenic centre is defined to be either R or S. The R/S-concept and rules for the determination of the absolute configuration in stereochemistry is known to the person skilled in the art.

In the present document a carbon-carbon double bond is defined as being "prochiral" if addition of molecular hydrogen to said carbon-carbon double bond leads to the formation of a stereogenic carbon centre.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

A "cis/trans isomerization catalyst" is a catalyst which is able to isomerize a cis isomer (Z-isomer) to a cis/trans isomer mixture (E/Z isomer mixture) or to isomerize a trans isomer (E-isomer) to a cis/trans isomer (E/Z isomer mixture).

The terms "E/Z", "cis/trans" and "R/S" denote mixtures of E and Z, of cis and trans, and of R and S, respectively.

In case identical labels for symbols or groups are present in several formulae, in the present document, the definition of said group or symbol made in the context of one specific formula applies also to other formulae which comprises said same label.

In the present document any single dotted line represents the bond by which a substituent is bound to the rest of a molecule.

"Assay yield" of an asymmetric hydrogenation is in the present application the molar ratio of number of molecules of completely saturated ketones or aldehydes or ketals or acetals to the number of molecules of unsaturated ketones or aldehydes or ketals or acetals being submitted to the hydrogenation.

6,10-Dimethylundec-5-en-2-one is a known substance and can, for example, be synthesized from 3,7-dimethyloct-1-en-3-ol and 2-methoxyprop-1-ene as disclosed in DE 1193490. 3,7-Dimethyloct-1-en-3-ol can, for example, be synthesized according to the procedure disclosed in WO 2012/025559 A2. The entire content of DE 1193490 and WO 2012/025559 A2 is hereby incorporated by reference.

6,10-Dimethylundec-5-en-2-one is a mixture of (E)-6,10-dimethylundec-5-en-2-one and (Z)-6,10-dimethylundec-5-en-2-one.

6,10-Dimethylundeca-5,9-dien-2-one is commercially available and can be, for example, synthesized from linalool by the Carroll rearrangement, and is a mixture of (E)-6,10-dimethylundeca-5,9-dien-2-one and (Z)-6,10-dimethylundeca-5,9-dien-2-one.

In a first step (step a) of the process a mixture of (E)-6,10-dimethylundec-5-en-2-one and (Z)-6,10-dimethylundec-5-en-2-one or a mixture of (E)-6,10-dimethylundeca-5,9-dien-2-one and (Z)-6,10-dimethylundeca-5,9-dien-2-one is provided.

Separation

Steps b) and e) relate to the separation of one of the isomers of 6,10-dimethylundec-5-en-2-one or of 6,10-dimethylundeca-5,9-dien-2-one from the mixture of step a) and to the separation of one of the isomers of (R)-6,10,14-trimethylpentadec-5-en-2-one from the mixture obtained in step d), respectively.

This separation of isomers in step b) and/or e) can be done in different ways. A first possibility is the separation by means of chromatography. A further and preferred way of separation is that the separation of isomers in step b) and/or e) is done by distillation. The separation is possible by the fact that the isomers have different boiling points. In order to minimize thermal degradation of the isomers it is advisable to distil under reduced pressure and by means of a distillation column.

As the isomers to be separated have different boiling points (see table 1) the isomers can be separated by distillation. Using specific distillation techniques and equipment it is possible to separate the isomer having the higher or the lower boiling point.

TABLE 1

Boiling points of isomers.

| Substance | Boiling point |
| --- | --- |
| (E)-6,10-dimethylundec-5-en-2-one | 112° C. at 5 mbar |
| (Z)-6,10-dimethylundec-5-en-2-one | 109° C. at 5 mbar |
| (E)-6,10-dimethylundeca-5,9-dien-2-one | 78° C. at 0.5 mbar |
| (Z)-6,10-dimethylundeca-5,9-dien-2-one | 75° C. at 0.5 mbar |
| (R,E)-6,10,14-trimethylpentadec-5-en-2-one | 122° C. at 2 mbar |
| (R,Z)-6,10,14-trimethylpentadec-5-en-2-one | 119° C. at 2 mbar |

In a preferred embodiment the distillation is done in the presence of a cis/trans isomerization catalyst.

Cis/Trans Isomerization

Cis/trans isomerization catalysts are catalysts which isomerize the carbon-carbon double bonds. It has been found that for the purpose of this invention said cis/trans isomerization catalysing the cis/trans isomerization of the double bonds in the 5 and 9 positions is particularly nitrogen monoxide (NO) or an organic sulphur compound, particularly a polythiol.

Particularly suitable as cis/trans isomerization catalysts are polythiols of formula (X) or aromatic polythiols

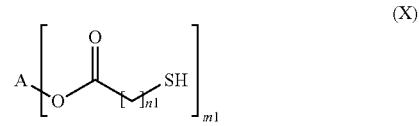

wherein n1 represents an integer from 1 to 4, particularly 2, and m1 represents an integer from 2 to 8, particularly 3 or 4, preferably 4;

and A represents an aliphatic m1-valent hydrocarbon group of the molecular weight of between 28 g/mol and 400 g/mol, particularly between 90 and 150 g/mol.

The polythiols pentaerythritol tetra(mercaptoacetate), trimethylolpropane tris(mercaptoacetate), glycol dimercaptoacetate, pentaerythritol tetra-(3-mercaptopropionate), trimethylolpropanetri-(3-mercaptopropionate)(=2-ethyl-2-(((3-mercaptopropanoyl)oxy)methyl)propane-1,3-diyl bis (3-mercaptopropanoate)) and glycol di-(3-mercaptopropionate) have been shown to be highly preferred polythiols of formula (X) and are the preferred polythiols of all the above mentioned polythiols.

Particularly preferred as aromatic polythiols are 4,4'-dimercaptobiphenyl or 4,4'-thiodibenzenethiol.

The use of polythiols of formula (X) as cis/trans isomerization catalysts is very advantageous in that polythiols have generally very low vapor pressures (i.e. high boiling points) allowing them to be used at elevated temperatures, e.g. while distilling the low boiling isomer. Furthermore, the polythiols bear a high density of thiol-functionalities per molecular weight, which is very advantageous, in that only little catalyst needs to be added.

The use of polythiol as cis/trans isomerization catalysts is very advantageous as they allow a very fast isomerization.

Nitrogen monoxide (NO) is a gas and can be introduced to the ketone or ketal to be isomerized as such or in the form of a gas mixture, particularly in combination with at least one inert gas, particularly with nitrogen. In the case a gas mixture is used the amount of nitrogen monoxide in the gas mixture is preferably in the range of 1-99%, particularly of 5-95%, by weight of the gas mixture. Particularly, in view of corrosion and toxicity, the amount of nitrogen monoxide in the gas mixture is preferably in the range of 10-60%) by weight of the gas mixture.

The use of nitrogen monoxide as cis/trans isomerization catalysts is very advantageous in that the isomerization catalyst can be removed very easily from the ketone or ketal to be isomerized.

Nitrogen monoxide is preferably introduced to the ketone or ketal at atmospheric pressure or up to 1 MPa over-pressure. The over-pressure preferably amounts to 10 to 300 kPa.

Nitrogen monoxide (NO) or a mixture of nitrogen monoxide (NO) with other gases is preferably introduced in a continuous way by means of a tube and bubbled through the ketone or ketal to be isomerized.

The use of cis/trans isomerization allows the transformation of a pure cis or trans isomer or any mixtures of the isomers to yield a thermodynamically equilibrated mixture of the cis and trans isomer. Overall, this enables the separation of the desired isomer by distillation and transformation (isomerization) of the non-preferred isomer (residual isomer) into the desired isomer.

The distillation can be performed in the presence of the cis/trans isomerization catalyst (one-pot isomerization or in-situ isomerization), so that the desired isomer is re-formed continuously and can be separated by distillation.

Furthermore, the cis/trans isomerization can occur in a separate vessel in which the cis/trans isomerization catalyst is added to the remainder of the distillation. Hence, the residual isomer is isomerized by means of a cis/trans isomerization catalyst and subsequently added to the corresponding mixture of isomers provided in steps a) and d), respectively.

The use of the cis/trans isomerization in step b) and/or e) allows a high yield in the desired isomer. In preferred cases, it can be achieved that essentially all of the undesired isomer is overall isomerized to the desired isomer.

Preferably, particularly in the case where the isomerization catalyst is not nitrogen monoxide, more preferably in the case of polythiols as isomerization catalysts, the isomerization is undertaken at temperatures higher than 20° C., particularly at a temperature of between 20° C. and the boiling point of the desired isomer, particularly between 50° C. and the boiling point of the desired isomer. The isomerization can occur at ambient pressure or at reduced pressure. In case of the one-pot isomerization the isomerization is preferably undertaken under reduced pressure.

Particularly for the case of nitrogen monoxide being cis/trans isomerization catalyst the isomerization is undertaken at ambient or over pressure.

It further has been observed that in the isomerization with polythiols addition of polar solvents such as amides, pyrrolidones, sulfones, sulfoxides, ionic liquids, particularly N,N-dimethylformide (DMF) or N-methyl-2-pyrrolidone (NMP), sulfolane, dimethylsulfoxide (DMSO) and 1-butyl-3-methylimidazolium bromide has an accelerating effect on the isomerization.

Therefore, it is preferred that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP), sulfolane and dimethylsulfoxide (DMSO).

More preferred it is that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP) and dimethylsulfoxide (DMSO).

The amount of cis/trans isomerization catalyst is preferably between 1 and 20% by weight in relation to the amount of the isomers of 6,10-dimethylundec-5-en-2-one or of 6,10-dimethylundeca-5,9-dien-2-one, respectively to (R)-6,10,14-trimethylpentadec-5-en-2-one.

Ketal Formation

In a further embodiment before the step c) a step $c_o$) takes place $c_o$) forming a ketal of the isomer of 6,10-dimethylundec-5-en-2-one or of 6,10-dimethylundeca-5,9-dien-2-one separated in step b).

Hence, in step c) the ketal of 6,10-dimethylundec-5-en-2-one or of 6,10-dimethylundeca-5,9-dien-2-one is asymmetrically hydrogenated and after the asymmetric hydrogenation the hydrogenated ketal is hydrolysed to the ketone and yielding (R)-6,10-dimethylundecan-2-one.

In a further embodiment before the step f) a step $f_o$) takes place $f_o$) forming a ketal of the isomer of (R)-6,10,14-trimethylpentadec-5-en-2-one separated in step e)

Hence, in step f) the ketal of (R)-6,10,14-trimethylpentadec-5-en-2-one is asymmetrically hydrogenated and after the asymmetric hydrogenation the hydrogenated ketal is hydrolysed to the ketone and yielding (6R,10R)-6,10,14-trimethylpentadecan-2-one.

The formation of a ketal from a ketone, per se, is known to the person skilled in the art.

The ketal of an unsaturated ketone can be preferably formed from the above mentioned unsaturated ketone and an alcohol.

It is known to the person skilled in the art that there are alternative routes of synthesis for ketals. In principle, the ketal can also be formed by treating a ketone with ortho-esters or by trans-ketalization such as disclosed for example in Pério et al., *Tetrahedron Letters* 1997, 38 (45), 7867-7870, or in Lorette and Howard, *J. Org. Chem.* 1960, 521-525, the entire content of both is hereby incorporated by reference.

Preferably the ketal is formed from the above mentioned unsaturated ketone and an alcohol.

The alcohol can comprise one or more hydroxyl groups. The alcohol may be a phenolic alcohol or an aliphatic or cycloaliphatic alcohol. Preferably the alcohol has one or two hydroxyl groups.

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated $C_1$-$C_8$-alkyl alcohols, particularly 2,2,2-trifluoroethanol. Particularly suitable are primary or secondary alcohols. Preferably primary alcohols are used as alcohols with one hydroxyl group. Particularly methanol, ethanol, 1-propanol, 2-propanol, 1-butanol, 2-butanol or 2,2,2-trifluoroethanol, preferably methanol, ethanol, 1-propanol, 1-butanol or 2,2,2-trifluoroethanol, are used as alcohols with one hydroxyl group.

In another embodiment the alcohol is a diol, hence has two hydroxyl groups. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2,2-dimethylpropane-1,3-diol, 1,2-dimethylpropane-1,3-diol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl group are in one embodiment bound to two adjacent carbon atoms, hence these dials are vicinal dials. Vicinal dials form a 5 membered ring in a ketal.

Particularly suitable are vicinal dials which are selected from the group consisting of ethane-1,2-diol, propane-1,2-diol, butane-1,2-diol, butane-2,3-diol, 2-methylpropane-1,2-diol, benzene-1,2-dial and syn-cyclohexane-1,2-diol, particularly ethane-1,2-diol.

Other particularly suitable are dials, in which the hydroxyl groups are separated by 3 carbon atoms, and, hence, form a very stable 6 membered ring in a ketal. Particularly suitable dials of this type are propane-1,3-diol, butane-1,3-diol, 2-methylpropane-1,3-diol, 2-methylbutane-1,3-diol, 2,2-dimethylpropane-1,3-diol, 1,2-dimethylpropane-1,3-diol, 3-methylpentane-2,4-dial and 2-(hydroxymethyl)-cyclohexanol.

Preferably primary alcohols are used as dials.

The reaction conditions and stoichiometry used for the ketal formation are known to the person skilled in the art.

The preferred ketals have the formula (XI) or (XII)

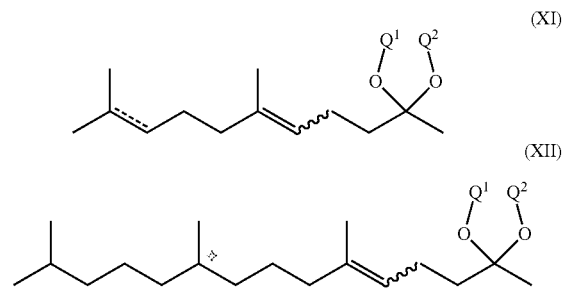

wherein a wavy line represents a carbon-carbon bond which is linked to the adjacent carbon-carbon double bond so as to have said carbon-carbon double bond either in the Z or in the E-configuration;
and wherein the double bond having dotted lines ( ═══ ) in formula represent either a single carbon-carbon bond or a double carbon-carbon bond;
and wherein ✧ represents a stereogenic centre;
and wherein
$Q^1$ and $Q^2$
stand either individually or both for a $C_1$-$C_{10}$ alkyl group or a halogenated $C_1$-$C_{10}$ alkyl group;
or form together a $C_2$-$C_6$ alkylene group or a $C_6$-$C_8$ cycloalkylene group.
$Q^1$ and $Q^2$ stand particularly for
either a linear $C_1$-$C_{10}$ alkyl group or fluorinated linear $C_1$-$C_{10}$ alkyl group, preferably a linear $C_1$-$C_4$ alkyl group or a —$CH_2CF_3$ group
or a group of formula

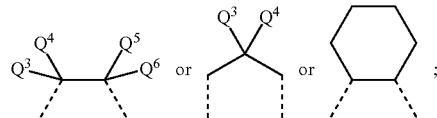

in which $Q^3$, $Q^4$, $Q^5$ and $Q^6$ are independently from each other hydrogen atoms or methyl or ethyl groups.

Particularly $Q^1$ and $Q^2$ stand both for a fluorinated linear $C_1$-$C_{10}$ alkyl group, preferably a linear $C_1$-$C_4$ alkyl group or a —$CH_2CF_3$ group or form together the alkylene group $CH_2$—$C(CH_3)_2$—$CH_2$.

Hence the preferred ketals to be asymmetrically hydrogenated are selected from the group consisting of (E)-2-(4,8-dimethylnona-3,7-dien-1-yl)-2,5,5-trimethyl-1,3-dioxane, (E)-2-(4,8-dimethylnon-3-en-1-yl)-2,5,5-trimethyl-1,3-dioxane, (E)-2,6-dimethyl-10,10-bis(2,2,2-trifluoroethoxy)undeca-2,6-diene, (E)-6,10-dimethyl-2,2-bis(2,2,2-trifluoroethoxy)undec-5-ene, (Z)-2-(4,8-dimethylnona-3,7-dien-1-yl)-2,5,5-trimethyl-1,3-dioxane, (Z)-2-(4,8-dimethylnon-3-en-1-yl)-2,5,5-trimethyl-1,3-dioxane, (Z)-2,6-dimethyl-10,10-bis(2,2,2-trifluoroethoxy)undeca-2,6-diene, (Z)-6,10-dimethyl-2,2-bis(2,2,2-trifluoroethoxy)undec-5-ene; (E)-2,5,5-trimethyl-2-(4,8,12-trimethyltridec-3-en-1-yl)-1,3-dioxane, (E)-6,10,14-trimethyl-2,2-bis(2,2,2-trifluoroethoxy)pentadec-5-ene, (Z)-2,5,5-trimethyl-2-(4,8,12-trimethyltridec-3-en-1-yl)-1,3-dioxane, and (Z)-6,10,14-trimethyl-2,2-bis(2,2,2-trifluoroethoxy)pentadec-5-ene; (R,E)-2,5,5-trimethyl-2-(4,8,12-trimethyltridec-3-en-1-yl)-1,3-dioxane, (R,E)-6,10,14-trimethyl-2,2-bis(2,2,2-trifluoroethoxy)pentadec-5-ene; (R,Z)-2,5,5-trimethyl-2-(4,8,12- trimethyltridec-3-en-1-yl)-1,3-dioxane and (R,Z)-6,10,14-trimethyl-2,2-bis(2,2,2-trifluoroethoxy)pentadec-5-ene.

The hydrolysis of the hydrogenated ketal to the corresponding ketone is known to the person skilled in the art. Particularly suitable is the hydrolysis by means of an acid and isolation of the ketone formed, particularly by means of extraction.

Asymmetric Hydrogenation

Steps c) and f) involve asymmetric hydrogenations by molecular hydrogen in the presence of a chiral iridium complex.

Chiral iridium complexes are compounds having organic ligands being coordinated to a central iridium atom. The chirality of chiral iridium complexes is due to either the chirality of the ligands or the spacial arrangements of the ligands. This concept of chirality is well known from complex chemistry. Ligands can be monodentate or polydentate. Preferably, the ligands bound to the iridium central atom are chelating ligands. For the present invention, it has been shown that particularly chiral iridium complexes having an organic ligand bearing a stereogenic centre are very suitable.

It is preferred that the chiral iridium complex is bound to a chelating organic ligand having N and P as coordinating atoms and to either two olefins or to a diene having two carbon-carbon double bonds, and that, hence, the chiral iridium complex has preferably the following formula (III-0)

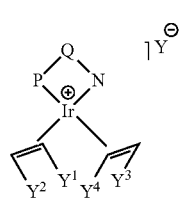
(III-0)

wherein

P-Q-N stands for a chelating organic ligand comprising a stereogenic centre or has planar or axial chirality and has a nitrogen and phosphorous atom as binding site to the iridium centre of the complex;

$Y^1$, $Y^2$, $Y^3$ and $Y^4$ are independently from each other hydrogen atoms, $C_{1-12}$-alkyl, $C_{5-10}$-cycloalkyl, or aromatic group; or at least two of them form together at least a two-valent bridged group of at least 2 carbon atoms; with the proviso that $Y^1$, $Y^2$, $Y^3$ and $Y^4$ are not all hydrogen atoms; and $Y^\ominus$ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C-SO_3^-$ or $F_9C_4-SO_3^-$; $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$.

The nitrogen and the phosphorous atom are preferably separated by 2 to 5, preferably 3, atoms in the chemical formula of the ligand P-Q-N.

The chelating organic ligand P-Q-N is preferably selected from the formulae (III-N1), (III-N2), (III-N3), (III-N4), (III-N5), (III-N6), (III-N7), (III-N8) and (III-N9)

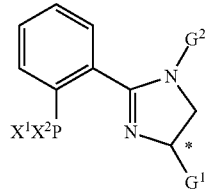
(III-N1)

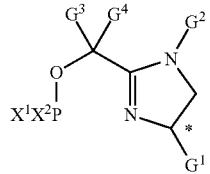
(III-N2)

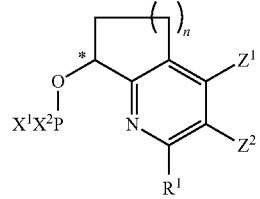
(III-N3)

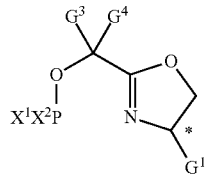
(III-N4)

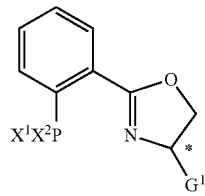
(III-N5)

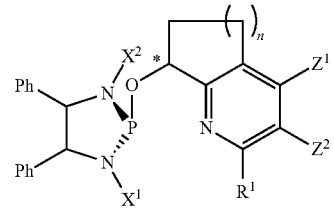
(III-N6)

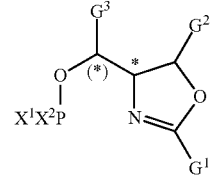
(III-N7)

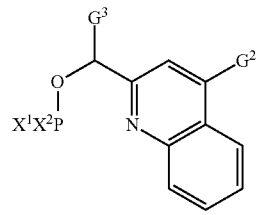
(III-N8)

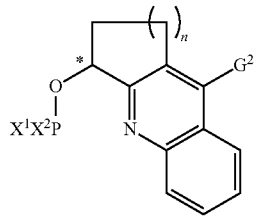

(III-N9)

wherein G¹ represents either a $C_1$-$C_4$-alkyl, $C_{5\text{-}7}$-cycloalkyl, adamantyl, phenyl (optionally substituted with one to three $C_{1\text{-}5}$-alkyl, $C_{1\text{-}4}$-alkoxy, $C_{1\text{-}4}$-perfluoroalkyl groups and/or one to five halogen atoms)), benzyl, 1-naphthyl, 2-naphthyl, 2-furyl group;

G², G³ and G⁴ represent independently from each other hydrogen atoms or a $C_1$-$C_4$-alkyl, $C_{5\text{-}7}$-cycloalkyl, adamantyl, phenyl (optionally substituted with one to three $C_{1\text{-}5}$-, $C_{1\text{-}4}$-alkoxy, $C_{1\text{-}4}$-perfluoroalkyl groups and/or one to five halogen atoms)), benzyl, 1-naphthyl, 2-naphthyl, 2-furyl group;

X¹ and X² are independently from each other hydrogen atoms, $C_{1\text{-}4}$-alkyl, $C_{5\text{-}7}$-cycloalkyl, adamantyl, phenyl (optionally substituted with one to three $C_{1\text{-}5}$-alkyl, $C_{1\text{-}4}$-alkoxy, $C_{1\text{-}4}$-perfluoroalkyl groups and/or one to five halogen atoms)), benzyl, 1-naphthyl, 2-naphthyl, 2-furyl or ferrocenyl;

Ph stands for phenyl;

n is 1 or 2 or 3, preferred 1 or 2;

and R¹, Z¹ and Z² are as defined later for formula (III)

In case Y¹ and Y² and/or Y³ and Y⁴ form an olefin of the formula Y¹-=-Y² and/or of the Formula Y³-=-Y⁴, this olefin is or these olefins are preferably selected from the group consisting of ethene, prop-1-ene, 2-methylprop-1-ene, 2-methyl-but-2-ene, 2,3-dimethylbut-2-ene, (Z)-cyclooctene, cyclohexene, cycloheptene, cyclopentene and norbornene.

In case Y¹, Y², Y³ and Y⁴ are forming a diene, it is either cyclic (double bond in a cycle) or acyclic (double bond not in a cycle).

The two carbon-carbon double bonds of the diene are preferably linked by two carbon bonds, i.e. the dienes preferably comprise the substructure C=C—C—C—C=C.

Examples of preferred acylic dienes are hexa-1,5-diene, hepta-1,5-diene, octa-1,5-diene, octa-2,6-diene, 2,4-dialkyl-2,7-octadiene, 3,6-dialkylocta-2,6-diene, 1,2-divinylcyclohexane and 1,3-butadiene.

Examples for cyclic dienes are cycloocta-1,5-diene, cyclohexa-1,4-diene, cyclohexa-1,3-diene, 3,4,7,8-tetraalkylcycloocta-1,5-diene, 3,4,7-trialkylcycloocta-1,5-diene, 3,4-di-alkylcycloocta-1,5-diene, 3,7-di-alkylcycloocta-1,5-diene, 3,8-di-alkylcycloocta-1,5-diene, 3-alkylcycloocta-1,5-diene; norbornadiene, 1-alkylnorbornadiene, 2-alkylnorbornadiene, 7-alkylnorbornadiene, dicyclopentadiene, cyclopentadiene and (1s,4s)-bicyclo[2.2.2]octa-2,5-diene.

Preferred diene is cycloocta-1,5-diene.

A highly preferred class of chiral iridium complexes are chiral iridium complexes of formula (III)

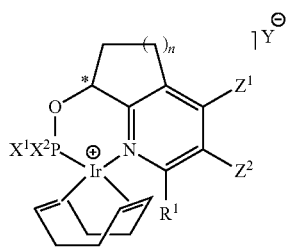

(III)

wherein n is 1 or 2 or 3, preferred 1 or 2;

X¹ and X² are independently from each other hydrogen atoms, $C_{1\text{-}4}$-alkyl, $C_{5\text{-}7}$-cycloalkyl, adamantyl, phenyl (optionally substituted with one to three $C_{1\text{-}5}$-, $C_{1\text{-}4}$-alkoxy, $C_{1\text{-}4}$-perfluoroalkyl groups and/or one to five halogen atoms)), benzyl, 1-naphthyl, 2-naphthyl, 2-furyl or ferrocenyl;

Z¹ and Z² are independently from each other hydrogen atoms, $C_{1\text{-}5}$-alkyl or $C_{1\text{-}5}$-alkoxy groups;

or Z¹ and Z² stand together for a bridging group forming a 5 to 6 membered ring;

Y⁻ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C$—$SO_3^-$ or $F_9C_4$—$SO_3^-$; $ClO_4^-$, $Al(OC_6F_5)_4^-$, $Al(OC(CF_3)_3)_4^-$, $N(SO_2CF_3)_2^-$ $N(SO_2C_4F_9)_2^-$ and $B(C_6F_5)_4^-$;

R¹ represents either phenyl or o-tolyl or m-tolyl or p-tolyl or a group of formula (IVa) or (IVb) or (IVc)

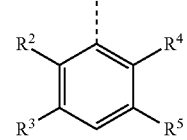

(IVa)

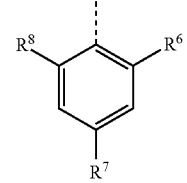

(IVb)

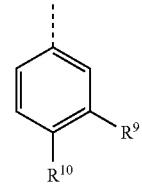

(IVc)

wherein R² and R³ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogen atoms or by $C_1$-$C_4$-alkyl groups or by $C_1$-$C_4$-alkoxy groups R⁴ and R⁵ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogen atoms or by $C_1$-$C_4$-alkyl groups or by $C_1$-$C_4$-alkoxy groups;

R⁶ and R⁷ and R⁸ represent each a $C_1$-$C_4$-alkyl group or a halogenated $C_1$-$C_4$-alkyl group;

R⁹ and R¹⁹ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogen atoms or by $C_1$-$C_4$-alkyl groups or by $C_1$-$C_4$-alkoxy groups;

and wherein * represents a stereogenic centre of the complex of formula (III).

The complex of formula (III) is neutral, i.e. the complex consists of a complex cation of formula (III') and anion Y as defined before.

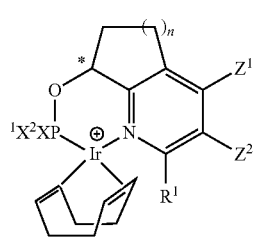

(III')

The person skilled in the art knows that anions and cations may be dissociated.

X¹ and/or X² represent preferably hydrogen atoms, methyl, ethyl, n-propyl, iso-propyl, n-butyl, iso-butyl, tert-butyl, n-pentyl, iso-pentyl, neopentyl, cyclopentyl, cyclohexyl, cycloheptyl, adamantly, phenyl, benzyl, o-tolyl, m-tolyl, p-tolyl, 4-methoxyphenyl, 4-trifluoromethylphenyl, 3,5-di-tert-butylphenyl, 3,5-dimethoxyphenyl, 1-naphthyl, naphthyl, 2-furyl, ferrocenyl or a phenyl group which is substituted with one to five halogen atoms.

In case of X¹ and/or X² representing phenyl groups which are substituted with one to five halogen atoms, the phenyl groups substituted by fluorine atoms are particularly useful, i.e. $C_6H_4F$, $C_6H_3F_2$, $C_6H_2F_3$, $C_6HF_4$ or $C_6F_5$.

In case of X¹ and/or X² representing phenyl groups which are substituted with one to three $C_{1-4}$-alkyl, the phenyl groups substituted by methyl group(s) are particularly useful, particularly ortho-tolyl and para-tolyl.

Preferably both X¹ and X² represent the same substituent.

Most preferred both X¹ and X² are phenyl or ortho-tolyl groups.

It is preferred that the $C_1$-$C_4$-alkyl or alkoxy groups used in the definition of R², R³, R⁴, R⁵ R⁶, R⁷, R⁸, R⁹ and R¹⁹ above are primary or secondary, preferably primary, alkyl or alkoxy groups.

A particularly suited substituent R¹ of formula (IVa) is the 9-anthryl or 1-naphthyl group.

A further particularly suited substituent R¹ of formula (IVb) is the mesityl group.

A further particularly suited substituent R¹ of formula (IVc) is the 2-naphthyl group.

Preferably R¹ is represented by phenyl (abbreviated as "Ph") or formula (IV-1) or (IV-2) or (IV-3), particularly (IV-1) or (IV-3).

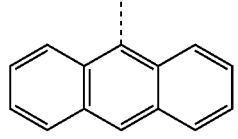

abbreviated as "Anth"

(IV-1)

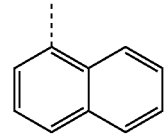

abbreviated as "1-Naphth"

(IV-2)

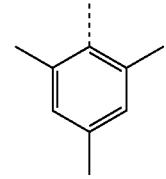

abbreviated as "Mes"

(IV-3)

It has been found that the most preferred substituent R¹ is either 9-anthryl or phenyl.

The preferred chiral iridium complexes of formula (III) are the complexes of formulae (III-A), (III-B), (III-C), (III-D), (III-E) and (III-F).

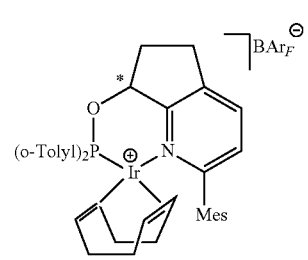

(III-A)

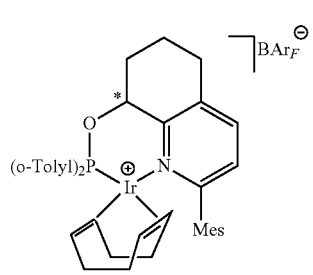

(III-B)

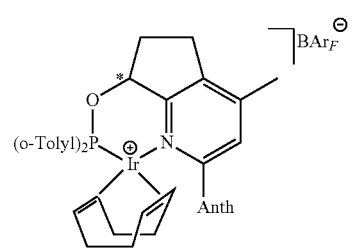

(III-C)

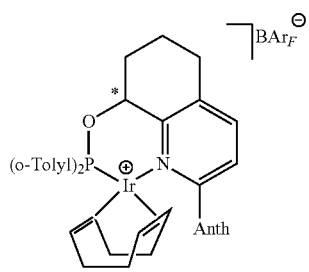
(III-D)

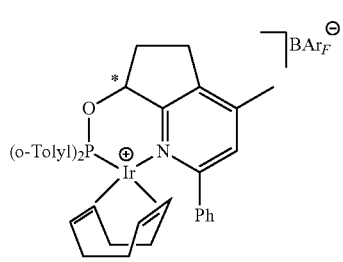
(III-E)

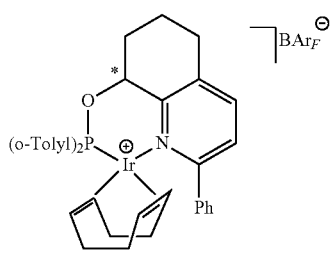
(III-F)

Most preferred as chiral iridium complexes of formula (III) are the complexes of formulae (III-C) and (III-D) and (III-F), particularly the one of formula (III-C) or (III-F).

The chiral iridium complexes of formula (III) can be synthesized accordingly as described in detail in *Chem. Sci.*, 2010, 1, 72-78 whose entire content is hereby incorporated by reference.

The iridium complex of formula (III) is chiral. The chirality at said chiral centre marked by the asterisk is either S or R. i.e. there exist two enantiomers (IIIa) and (IIIb) of the chiral complex of formula (III):

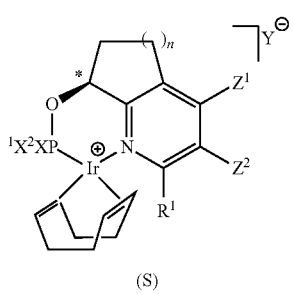
(IIIa)

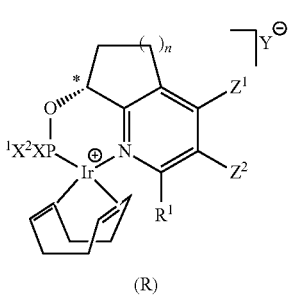
(IIIb)

The individual enantiomers of the complex of formula (III) could be principally separated after the complexation step from a racemic mixture. However, as *Chem. Sci.*, 2010, 1, 72-78 discloses, the synthesis of the complex of formula (III) comprises a reaction involving a non-racemic chiral alcohol. As it is known that the further reaction steps do not modify the chirality of the complex its isomeric purity (S:R-ratio) is governed therefore by the enantiomeric purity of said alcohol. As said corresponding alcohol can be obtained in a R/S ratio of more than 99% resp. lower than 1%, the complex of formula (III) can be obtained in extremely high enantiomeric purities, particularly in a R/S ratio of more than 99% resp. lower than 1%.

The chiral iridium complex is preferably used in an excess of one enantiomer.

Particularly, it is preferred that the ratio of the molar amounts of the individual enantiomers R:S of the chiral iridium complex of formula (III) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

In one embodiment the stereogenic centre indicated by * has the R-configuration.

In another embodiment the stereogenic centre indicated by * has the S-configuration.

The hydrogenating agent is molecular hydrogen ($H_2$).

The amount of chiral iridium complex is preferably from about 0.0001 to about 5 mol %, preferably from about 0.001 to about 2 mol %, more preferably from about 0.01 to about 1 mol %, based on the amount of the ketone resp. ketal.

The hydrogenation can be carried out in substance or in an inert carrier, particularly in an inert solvent, or a mixture of inert solvents. The hydrogenation is preferred carried out in substance (neat).

Preferred suitable solvents are halogenated hydrocarbons, hydrocarbons, carbonates, ethers and halogenated alcohols.

Particularly preferred solvents are hydrocarbons, fluorinated alcohols and halogenated hydrocarbons, particularly halogenated aliphatic hydrocarbons.

Preferred examples of hydrocarbons are hexane, heptane, toluene, xylene and benzene, particularly toluene and heptane.

Preferred ethers are dialkylethers. Particularly useful ethers are dialklyethers with less than 8 carbon atoms. Most preferred ether is methyl tert.-butyl ether ($CH_3$—O—C($CH_3$)$_3$).

Preferred halogenated alcohols are fluorinated alcohols. A particularly preferred fluorinated alcohol is 2,2,2-trifluoroethanol.

One preferred group of halogenated hydrocarbon are halogenated aromatic compounds, particularly chlorobenzene.

Preferred examples of halogenated aliphatic hydrocarbons are mono- or polyhalogenated linear or branched or cyclic $C_1$- to $C_{15}$-alkanes. Especially preferred examples are mono- or polychlorinated or -brominated linear or branched or cyclic $C_1$- to $C_{15}$-alkanes. More preferred are mono- or polychlorinated linear or branched or cyclic $C_1$- to $C_{15}$-alkanes. Most preferred are dichloromethane, 1,2-dichloroethane, 1,1,1-trichloroethane, chloroform, and methylene bromide.

The most preferred solvent for the hydrogenation is dichloromethane.

The amount of solvent used is not very critical. However, it has been shown that the concentration of the ketone or ketal to be hydrogenated is preferably between 0.05 and 1 M, particularly between 0.2 and 0.7 M.

The hydrogenation reaction is conveniently carried out at an absolute pressure of molecular hydrogen from about 1 to about 100 bar, preferably at an absolute pressure of molecular hydrogen from about 20 to about 75 bar. The reaction temperature is conveniently between about 0 to about 100° C., preferably between about 10 to about 60° C.

The sequence of addition of the reactants and solvent is not critical.

The technique and apparatus suitable for the hydrogenation is principally known to the person skilled in the art.

By the asymmetric hydrogenation a prochiral carbon-carbon double bond is hydrogenated to form a chiral stereogenic centre at one or both of the carbon atoms.

In step c) either 6,10-dimethylundec-5-en-2-one or 6,10-dimethylundeca-5,9-dien-2-one, or a ketal of 6,10-dimethylundec-5-en-2-one or a ketal of 6,10-dimethylundeca-5,9-dien-2-one is asymmetrically hydrogenated.

In step f) either 6,10,14-trimethylpentadec-5-en-2-one or a ketal of 6,10,14-trimethylpentadec-5-en-2-one is hydrogenated.

In case a ketal is asymmetrically hydrogenated, after the asymmetric hydrogenation the asymmetrically hydrogenated ketal has preferably the formula (XV) or (XVI).

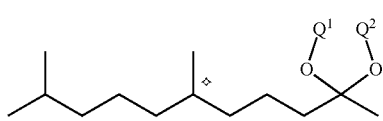
(XV)

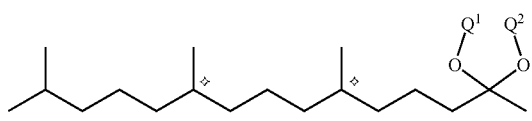
(XVI)

wherein ✧ represents a stereogenic centre;
and wherein $Q^1$ and $Q^2$ are as defined for formula (XI) and (XII).

Hence the preferred ketals which have been asymmetrically hydrogenated are preferably selected from the group consisting of 2-(4,8-dimethylnonyl)-2,5,5-trimethyl-1,3-dioxane, 6,10-dimethyl-2,2-bis(2,2,2-trifluoroethoxy)undecane, 2,5,5-trimethyl-2-(4,8,12-trimethyltridecyl)-1,3-dioxane, 6,10,14-trimethyl-2,2-bis(2,2,2-trifluoroethoxy) pentadecane;

(R)-2-(4,8-dimethylnonyl)-2,5,5-trimethyl-1,3-dioxane, (R)-6,10-dimethyl-2,2-bis(2,2,2-trifluoroethoxy)undecane, 2,5,5-trimethyl-2-((4R,8R)-4,8,12-trimethyltridecyl)-1,3-dioxane and (6R,10R)-6,10,14-trimethyl-2,2-bis(2,2,2-trifluoroethoxy)-pentadecane.

When these ketals are hydrolysed into the corresponding ketone, they yield 6,10-dimethylundecan-2-one or 6,10,14-trimethylpentadecan-2-one, or (R)-6,10-dimethylundecan-2-one or (6R,10R)-6,10,14-trimethylpentadecan-2-one, respectively.

Despite the fact that the asymmetric hydrogenation of 6,10-dimethylundec-5-en-2-one, 6,10-dimethylundeca-5,9-dien-2-one and (R)-6,10,14-trimethylpentadec-5-en-2-one by means of molecular hydrogen in the presence of a chiral iridium complex, particularly those of formula (III), is already rather fast and efficient and shows high conversion rates as well as excellent selectivities, it has been observed that the asymmetric hydrogenation can even be improved when ketals of the corresponding ketones are asymmetrically hydrogenated.

It has been observed that the chiral iridium complex of a specific chirality (R or S) converts the starting material into a product bearing a specific stereogenic centre, which is formed as a result of the asymmetric hydrogenation.

As is in the present invention it is desired to produce products bearing a stereocentre with R-configuration by asymmetric hydrogenation i.e. (R)-6,10-dimethylundecan-2-one in step c), and (6R,10R)-6,10,14-trimethylpentadecan-2-one in step f), respectively, the chirality of the chiral iridium complex needs to be selected depending on whether the olefin isomers being separated in step c) and step e), respectively, have the Z- or E-configuration.

It has been shown that when chiral iridium complexes of formula (III) having the S-configuration at the stereogenic centre indicated by * are used for the hydrogenation of E-isomers, i.e. (E)-6,10-dimethylundec-5-en-2-one and (R,E)-6,10,14-trimethylpentadec-5-en-2-one, respectively, the corresponding products, i.e. (R)-6,10-dimethylundecan-2-one in step c), and (6R,10R)-6,10,14-trimethylpentadecan-2-one in step f), are obtained bearing the R-configuration at the newly formed stereogenic centre. Correspondingly, the hydrogenation of Z-isomers, i.e. (Z)-6,10-dimethylundec-5-en-2-one and (R,Z)-6,10,14-trimethylpentadec-5-en-2-one, respectively, in the presence of the chiral iridium complex of formula (III) having the R-configuration at the stereogenic centre indicated by * furnishes the same products, i.e. (R)-6,10-dimethylundecan-2-one in step c), and (6R,10R)-6,10,14-trimethylpentadecan-2-one in step f), are obtained bearing the R-configuration at the newly formed stereogenic centre Surprisingly, it has been found that this finding is independent from whether a ketone or a ketal is used in step c) or f).

Therefore, the chiral iridium complex of formula (III) used in step c) and/or f) for the asymmetric hydrogenation preferably has the S-configuration at the stereogenic centre indicated by * in case (E)-6,10-dimethylundec-5-en-2-one, (E)-6,10-dimethylundeca-5,9-dien-2-one, or ketals thereof, or (R,E)-6,10,14-trimethylpentadec-5-en-2-one, or a ketal thereof, are to be hydrogenated;

or has the

R-configuration at the stereogenic centre indicated by * in case (Z)-6,10-dimethylundec-5-en-2-one, (Z)-6,10-dimethylundeca-5,9-dien-2-one, or ketals thereof, or (R,Z)-6,10,14-trimethylpentadec-5-en-2-one, or a ketal thereof, are to be hydrogenated.

Additives

In a preferred embodiment of the invention the asymmetric hydrogenation in step c) and/or step f) takes place in the presence of an additive which is selected from the group consisting of organic sulfonic acids, transition metal salts of organic sulfonic acids, metal alkoxides, aluminoxanes, alkyl aluminoxanes and B(R)$_{(3-v)}$(OZ)$_v$; wherein v stands for 0, 1, 2 or 3 and R stands for F, a C$_{1-6}$-alkyl, a halogenated C$_{1-6}$-alkyl, an aryl or halogenated aryl group; and Z stands a C$_{1-6}$-alkyl, a halogenated C$_{1-6}$-alkyl, an aryl or halogenated aryl group.

Particularly suitable additives are selected from the group consisting of triflic acid, alkyl aluminoxanes, particularly methyl aluminoxane, ethyl aluminoxane, tetra alkoxy titanates. B(R)$_{(3-v)}$(OZ)$_v$; particularly tri-isopropylborate and triethylborane and BF$_3$, preferably in the form of a BF$_3$ etherate.

Particularly useful as the transition metal salts of organic sulfonic acids are scandium, indium, yttrium and zirconium salts of organic sulfonic acids.

Metal alkoxides are known to the person skilled in the art. This term particularly relates to the alkoxides of the elements of the group 4 and 13 of the periodic system. It is also known to the person skilled in the art that the metal alkoxides often do not form well-defined structures. Characteristically, metal alkoxides have hydrocarbyl group bound by an oxygen atom to a metal centre. A metal alkoxide may also have different metal centres which are bridged by oxygen or oxygen containing groups, such as for example (polynuclear) aluminium oxoalkoxides.

Particularly useful as metal alkoxides are titanium alkoxides (also being called alkoxy titanates) zirconium alkoxides (also being called alkoxy zirconates) or aluminium alkoxides.

A particularly preferred class of metal alkoxide is of the type of polynuclear aluminium oxoalkoxides such as disclosed in *J. Chem. Soc., Dalton Trans.*, 2002, 259-266 or in *Organometallics* 1993, 12, 2429-2431.

Alkyl aluminoxanes, are known products which are particularly useful as co-catalysts for olefin polymerizations of the Ziegler-Natta type. They are prepared by controlled hydrolysis of trialkylaluminium compound, particularly trimethylaluminium or triethylaluminium. The hydrolysis can be achieved for example by hydrated metal salts (metal salts containing crystal water).

Preferably the additive is selected from the group consisting of triflic acid, alkyl aluminoxanes, particularly methyl aluminoxane, ethyl aluminoxane, tetra alkoxy titanates. B(R)$_{(3-v)}$(OZ)$_v$; particularly tri-isopropylborate and triethylborane and BF$_3$, preferably in the form of a BF$_3$ etherate.

More preferred are triflic acid, alkyl aluminoxanes, particularly methyl aluminoxane, ethyl aluminoxane, tetra alkoxy titanates, B(R)$_{(3-v)}$(OZ)$_v$; particularly tri-isopropylborate and triethylborane.

Especially good results have been obtained by an additive with has been obtained from trimethylaluminoxane and 2,2,2-trifluoroethanol or from trialkylaluminium and 2,2,2-trifluoroethanol.

It has been found that the quality and speed of the asymmetric hydrogenation using molecular hydrogen in the presence of a chiral iridium complex is enhanced significantly when the above mentioned additives are used.

It has been further observed that, most significantly, the efficiency of the asymmetric hydrogenation is maximized when the above mentioned additives are used with the corresponding ketal of the ketones to be asymmetrically hydrogenated, i.e. ketals of 6,10-dimethylundec-5-en-2-one, 6,10-dimethylundeca-5,9-dien-2-one and (R)-6,10,14-trimethylpentadec-5-en-2-one.

The increased efficiency has the effect that the amount of chiral iridium complex can be remarkably lowered by using an ketal of 6,10-dimethylundec-5-en-2-one, 6,10-dimethylundeca-5,9-dien-2-one or (R)-6,10,14-trimethylpentadec-5-en-2-one. and/or addition of the mentioned additive(s), particularly in the combination with fluorinated alcohols, particularly 2,2,2-trifluoroethanol, to achieve a given yield and stereospecific hydrogenation in the asymmetric hydrogenation as compared to the corresponding asymmetric hydrogenation of 6,10-dimethylundec-5-en-2-one, 6,10-dimethylundeca-5,9-dien-2-one and (R)-6,10,14-trimethylpentadec-5-en-2-one as such.

When the process comprises steps of cis/trans isomerization, as discussed above in detail, the process of invention is extremely interesting because for an optimal use of all starting material, it is not necessary to set up two parallel product lines for the separate asymmetric hydrogenation of each isomer using hydrogenation complexes of opposite chirality. Therefore, the in-situ isomerization, as discussed above, is much preferred.

Chemical Transformation

In step d) (R)-6,10-dimethylundecan-2-one is chemically transformed to a mixture of (R,E)-6,10,14-trimethylpentadec-5-en-2-one and (R,Z)-6,10,14-trimethylpentadec-5-en-2-one;

This chemical transformation can be done in different ways.

In a preferred method the chemical transformation of (R)-6,10-dimethylundecan-2-one to a mixture of (R,E)-6,10,14-trimethylpentadec-5-en-2-one and (R,Z)-6,10,14-trimethylpentadec-5-en-2-one in step d) is done by the steps
either
d1) ethynylation of (R)-6,10-dimethylundecan-2-one using ethyne in the presence of a basic substance to yield (7R)-3,7,11-trimethyldodec-1-yn-3-ol;
d2) hydrogenation of (7R)-3,7,11-trimethyldodec-1-yn-3-ol with molecular hydrogen in the presence of a Lindlar catalyst to yield (7R)-3,7,11-trimethyldodec-1-en-3-ol;
or
d1') vinylation of (R)-6,10-dimethylundecan-2-one by addition of a vinyl Grignard reagent to yield (7R)-3,7,11-trimethyldodec-1-en-3-ol;
followed by
either
d3) reacting (7R)-3,7,11-trimethyldodec-1-en-3-ol with 2-methoxyprop-1-ene to yield a mixture of (R,E)-6,10,14-trimethylpentadec-5-en-2-one and (R,Z)-6,10,14-trimethylpentadec-5-en-2-one;
or
d3') reacting (7R)-3,7,11-trimethyldodec-1-en-3-ol with an alkyl acetoacetate or diketene in the presence of a base and/or an acid to yield a mixture of (R,E)-6,10,14-trimethylpentadec-5-en-2-one and (R,Z)-6,10,14-trimethylpentadec-5-en-2-one.

Details for the reaction type and conditions of the variant using steps d1) is disclosed in EP 1 532 092 B1, particularly in example 2, or WO 2003/029175 A1 (using a basic anion exchange resin), the entire content of which is hereby incorporated by reference. The hydrogenation with molecular hydrogen in the presence of a Lindlar catalyst in step d2) is known to the person skilled in the art. For example A. Ofner et al, *Helv. Chin. Acta* 1959, 42, 2577-2584 disclose the combination of steps d1) and d2) the entire content of which is hereby incorporated by reference.

U.S. Pat. No. 4,028,385 for example discloses details for the reaction type and conditions of the variant using step d1')

as well as also for steps d1) and d2), the entire content of which is hereby incorporated by reference.

Details for the reaction type and conditions of the variant using step d3), which is a Saucy-Marbet reaction, are disclosed for example in DE 1193490 and DE 196 49 564 A1, the entire content of both documents is hereby incorporated by reference.

Details for the reaction type and conditions of the first variant in step d3'), which is a Carroll rearrangement, are disclosed for example in chapter 8 "The Carroll Rearrangement" in Hatcher et al., *The Claisen Rearrangement*; Hiersemann, M.; Nubbemeyer, U., Eds.; Wiley-VCH Verlag GmbH & Co. KGaA, 2007; 397-430, the entire content of both documents is hereby incorporated by reference. In the Carroll rearrangement the reaction occurs with an alkyl acetoacetate, preferably methyl acetoacetate or ethyl acetoacetate, in the presence of a base, preferably an alkali acetate such as sodium acetate.

The reaction type and conditions of the second variant in step d3') are disclosed for example in U.S. Pat. No. 2,795,617 or in W. Kimel et al., *J. Org. Chem.* 1957, 22, 1611-1618, the entire content of both documents is hereby incorporated by reference. The reaction preferably occurs with diketene in the presence of preferably pyridine and acetic acid resp. in the presence of an alkoxide.

As mentioned earlier, (6R,10R)-6,10,14-trimethylpentadecan-2-one is an important intermediate and is particularly useful for the synthesis of (R,R)-isophytol, (2-ambo)-α-tocopherol or of (2R,4'R,8'R)-α-tocopherol.

Therefore, in a further aspect the invention relates to a process of manufacturing (R,R)-isophytol ((3RS,7R,11R)-3,7,11,15-tetramethylhexadec-1-en-3-ol) which comprises the process of manufacturing (6R,10R)-6,10,14-trimethylpentadecan-2-one as described above in detail;
followed by the steps
either
g) ethynylation of (6R,10R)-6,10,14-trimethylpentadecan-2-one using ethyne in the presence of a base to yield (7R,11R)-3,7,11,15-tetramethylhexadec-1-yn-3-ol;
h) hydrogenation of (7R,11R)-3,7,11,15-tetramethylhexadec-1-yn-3-ol with molecular hydrogen in the presence of a Lindlar catalyst to yield (R,R)-isophytol;
or
h') vinylation of (6R,10R)-6,10,14-trimethylpentadecan-2-one by addition of a vinyl Grignard reagent to yield (R,R)-isophytol.

The conditions for steps g) and h) and h') correspond to the ones described for the analogous steps d1) and d2) and d1') in step d).

In a further aspect the invention relates to a process of manufacturing compound of formula (V) comprising the process of manufacturing (6R,10R)-6,10,14-trimethylpentadecan-2-one as described above in detail;
followed by the steps
either
g) ethynylation of (6R,10R)-6,10,14-trimethylpentadecan-2-one using ethyne in the presence of a basic substance to yield (7R,11R)-3,7,11,15-tetramethylhexadec-1-yn-3-ol;
h) hydrogenation of (7R,11R)-3,7,11,15-tetramethylhexadec-1-yn-3-ol with molecular hydrogen in the presence of a Lindlar catalyst to yield (R,R)-isophytol;
or
h') vinylation of (6R,10R)-6,10,14-trimethylpentadecan-2-one by addition of a vinyl Grignard reagent to yield (R,R)-isophytol;

followed by the steps
m) condensing (R,R)-isophytol with compound of formula (VI) to yield compound of formula (V) being an isomeric mixture in view of the chirality at the centre indicated by #;

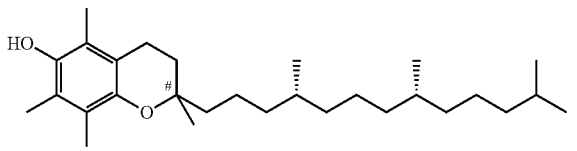

(V)

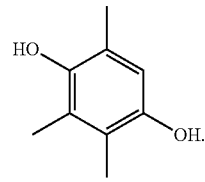

(VI)

wherein # represents a stereogenic centre

The conditions for steps g) and h) and h') correspond to the ones described for the analogous steps d1) and d2) and d1') in step d).

The condensation reaction of (R,R)-isophytol and compound of formula (VI), described as step m), is known by the person skilled in the art. For this condensation a series of catalysts may be used such as $ZnCl_2$/mineral acid, $BF_3$/$AlCl_3$, Fe/HCl, trifluoroacetic acid or boric acid/carboxylic acid as well as indium(III) or scandium(III) salts as disclosed in WO 2005/121115 A1. Furthermore, suitable catalysts are heteropoly acids, particularly 12-tungstophosphoric acid or 12-tungstosilicic acid such as disclosed in EP 0 970 953 A1.

The compounds of formula (V) represent (2-ambo)-α-tocopherol, i.e. a mixture of the corresponding (2R,4'R,8'R)-α-tocopherol and (2S,4'R,8'R)-α-tocopherol).

In a further aspect the invention relates to a process of manufacturing compound of formula (V-A) comprising the process of manufacturing (6R,10R)-6,10,14-trimethylpentadecan-2-one as described above in detail;
followed by the steps
either
g) ethynylation of (6R,10R)-6,10,14-trimethylpentadecan-2-one using ethyne in the presence of a basic substance to yield (7R,11R)-3,7,11,15-tetramethylhexadec-1-yn-3-ol;
h) hydrogenation of (7R,11R)-3,7,11,15-tetramethylhexadec-1-yn-3-ol with molecular hydrogen in the presence of a Lindlar catalyst to yield (R,R)-isophytol;
or
h') vinylation of (6R,10R)-6,10,14-trimethylpentadecan-2-one by addition of a vinyl Grignard reagent to yield (R,R)-isophytol;
followed by the steps
m) condensing (R,R)-isophytol with compound of formula (VI) to yield compound of formula (V) being an isomeric mixture in view of the chirality at the centre indicated by #;

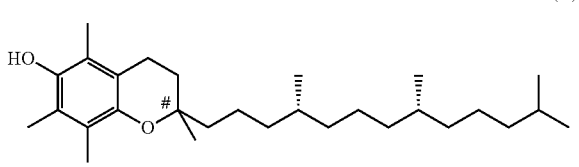
(V)

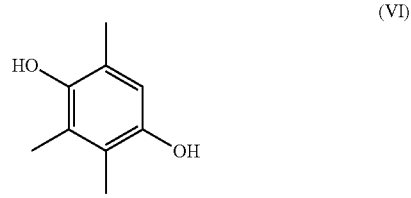
(VI)

wherein # represents a stereogenic centre; and n) isolating compound of formula (V-A) from the isomeric mixture of formula (V)

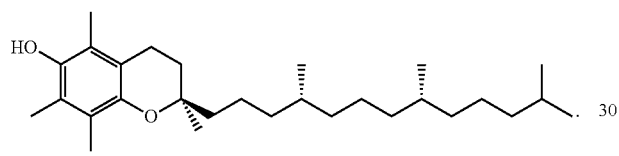
(V-A)

This process of manufacturing compound of formula (V-A) is the same as the process of manufacturing compound of formula (V) except for an additional step n).

The isolation of a (2R,4'R,8'R)-α-tocopherol from the corresponding (2-ambo)-α-tocopherol can be achieved by chromatographic separation by means of a chiral phase, particularly as described in WO2012/152779 A1. It is also preferred to enhance the yield in (2R,4'R,8'R)-α-tocopherol by means of epimerization of fractions enriched in (2S,4'R,8'R)-α-tocopherol as disclosed as step c) in WO2012/152779 A1. The entire content of WO2012/152779 A1 is hereby included by reference.

The substances selected from the group (E)-6,10-dimethylundec-5-en-2-one, (Z)-6,10-dimethylundec-5-en-2-one, (E)-6,10-dimethylundeca-5,9-dien-2-one, (Z)-6,10-dimethylundeca-5,9-dien-2-one, (R)-6,10-dimethylundecan-2-one; ketals of (E)-6,10-dimethylundec-5-en-2-one, ketals of (Z)-6,10-dimethylundec-5-en-2-one, ketals of (E)-6,10-dimethylundeca-5,9-dien-2-one, ketals of (Z)-6,10-dimethylundeca-5,9-dien-2-one; (R,E)-6,10,14-trimethylpentadec-5-en-2-one, (R,Z)-6,10,14-trimethylpentadec-5-en-2-one, ketals of (R,E)-6,10,14-trimethylpentadec-5-en-2-one, ketals of (R,Z)-6,10,14-trimethylpentadec-5-en-2-one, (6R,10R)-6,10,14-trimethylpentadecan-2-one, ketals of (6R,10R)-6,10,14-trimethylpentadecan-2-one, (7R)-3,7,11-trimethyldodec-1-yn-3-ol, (7R)-3,7,11-trimethyldodec-1-en-3-ol and (R,R)-isophytol are important intermediates for the synthesis of tocopherols, vitamin K1, as well as for flavours and fragrances or for pharmaceutical products. The majority of them have a typical odour which makes them very attractive to be used as ingredients in products of the industry of flavours and fragrances such as in perfumes.

In a further aspect, the invention relates to a composition comprising
at least one ketal of formula (XI) or (XII) and
at least one chiral iridium complex.

The ketal of formula (XI) or (XII) and the chiral iridium complex, their ratios and as well their preferred embodiments, properties and effects have been discussed in this documents already in great detail.

In a final aspect, the invention relates to ketals of formula (XX-A) or (XX-B) or (XX-C) or (XX-D)

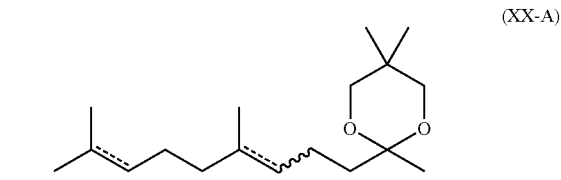
(XX-A)

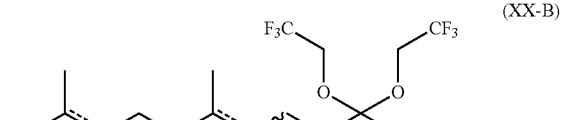
(XX-B)

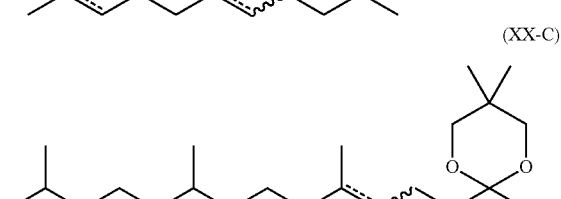
(XX-C)

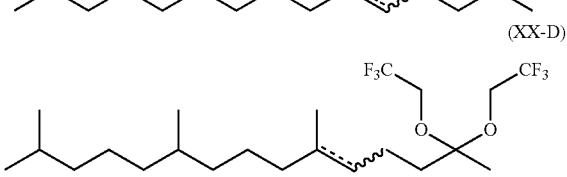
(XX-D)

wherein the double bond having dotted lines (═══) n the above formulae represents either a single carbon-carbon bond or a double carbon-carbon bond; and
wherein a wavy line represents a carbon-carbon bond which is linked to an adjacent single carbon bond (═══ representing —) or to an adjacent carbon-carbon double bond (═══ representing ═) so as to have said carbon-carbon double bond either in the Z or in the E-configuration.

Most preferred are the ketals of formulae (XX-B) and (XX-D).

The preferred ketals are being selected from the group consisting of (E)-2-(4,8-dimethylnona-3,7-dien-1-yl)-2,5,5-trimethyl-1,3-dioxane, (E)-2-(4,8-dimethylnon-3-en-1-yl)-2,5,5-trimethyl-1,3-dioxane, (E)-2,6-dimethyl-10,10-bis(2,2,2-tri-fluoroethoxy)undeca-2,6-diene, (E)-6,10-dimethyl-2,2-bis(2,2,2-trifluoroethoxy)undec-5-ene, (Z)-2-(4,8-dimethylnona-3,7-dien-1-yl)-2,5,5-trimethyl-1,3-dioxane, (Z)-2-(4,8-dimethylnon-3-en-1-yl)-2,5,5-trimethyl-1,3-dioxane, (Z)-2,6-dimethyl-10,10-bis(2,2,2-trifluoroethoxy)undeca-2,6-diene, (Z)-6,10-dimethyl-2,2-bis(2,2,2-tri-fluoroethoxy)undec-5-ene; (E)-2,5,5-trimethyl-2-(4,8,12-trimethyltridec-3-en-1-yl)-1,3-dioxane, (E)-6,10,14-trimethyl-2,2-bis(2,2,2-trifluoroethoxy)pentadec-5-ene, (Z)-2,5,5-trimethyl-2-(4,8,12-trimethyltridec-3-en-1-yl)-1,3-dioxane, and (Z)-6,10,14-trimethyl-2,2-bis(2,2,2-trifluoroethoxy)pentadec-5-ene; (R,E)-2,5,5-trimethyl-2-(4,8,12-trimethyltridec-3-en-1-yl)-1,3-dioxane, (R,E)-6,10,14- trimethyl-2,2-bis(2,2,2-trifluoroethoxy)pentadec-5-ene; (R,Z)-2,5,5-trimethyl-2-(4,8,12-trimethyltridec-3-en-1-yl)-1,3-dioxane and (R,Z)-6,10,14-trimethyl-2,2-bis(2,2,2-trifluoroethoxy)pentadec-5-ene; or selected from the group consisting of 2-(4,8-dimethylnonyl)-2,5-dimethyl-1,3-dioxane, 6,10-dimethyl-2,2-bis(2,2,2-trifluoroethoxy)undecane, 2,5,5-trimethyl-2-(4,8,12-trimethyltridecyl)-1,3-dioxane, 6,10,14-trimethyl-2,2-bis(2,2,2-trifluoroethoxy)pentadecane; (R)-2-(4,8-dimethylnonyl)-2,5-dimethyl-1,3-dioxane, (R)-6,10-dimethyl-2,2-bis(2,2,2-trifluoroethoxy)undecane, 2,5,5-trimethyl-2-((4R,8R)-4,8,12-trimethyltridecyl)-1,3-dioxane and (6R,10R)-6,10,14-trimethyl-2,2-bis(2,2,2-trifluoroethoxy)pentadecane.

All these ketals are particularly suited for the asymmetric hydrogenation as described above in detail or are the product of said asymmetric hydrogenation. As mentioned also before the ketals of unsaturated ketones behave extremely advantageously as compared to the corresponding ketones.

In the following paragraphs some preferred embodiments of the inventions are further discussed by means of schematic FIGS. 1 to 6. This, however, is not to be understood as limiting the invention to the embodiments described here in the figures.

Figure 2:
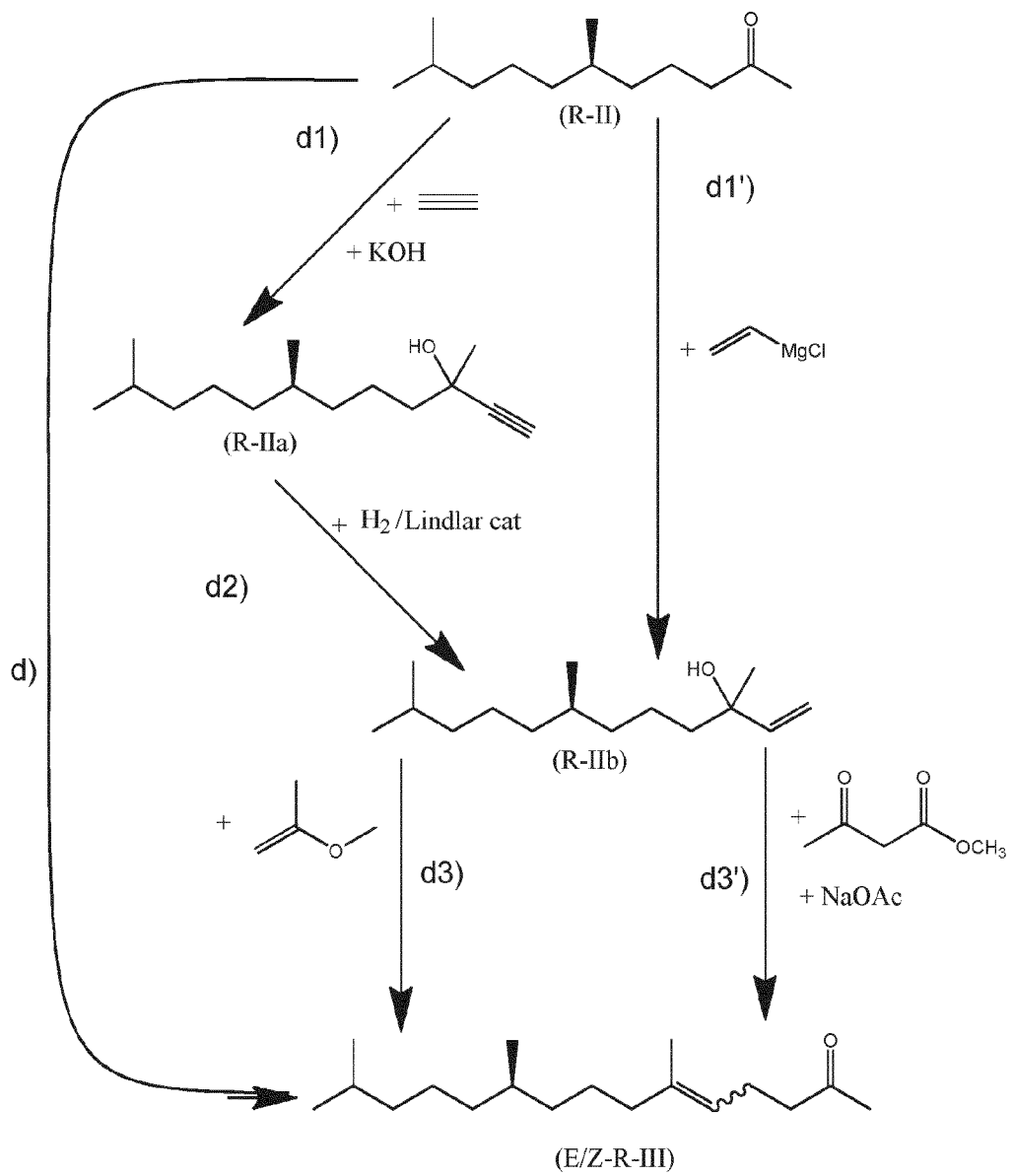
Figure 3:
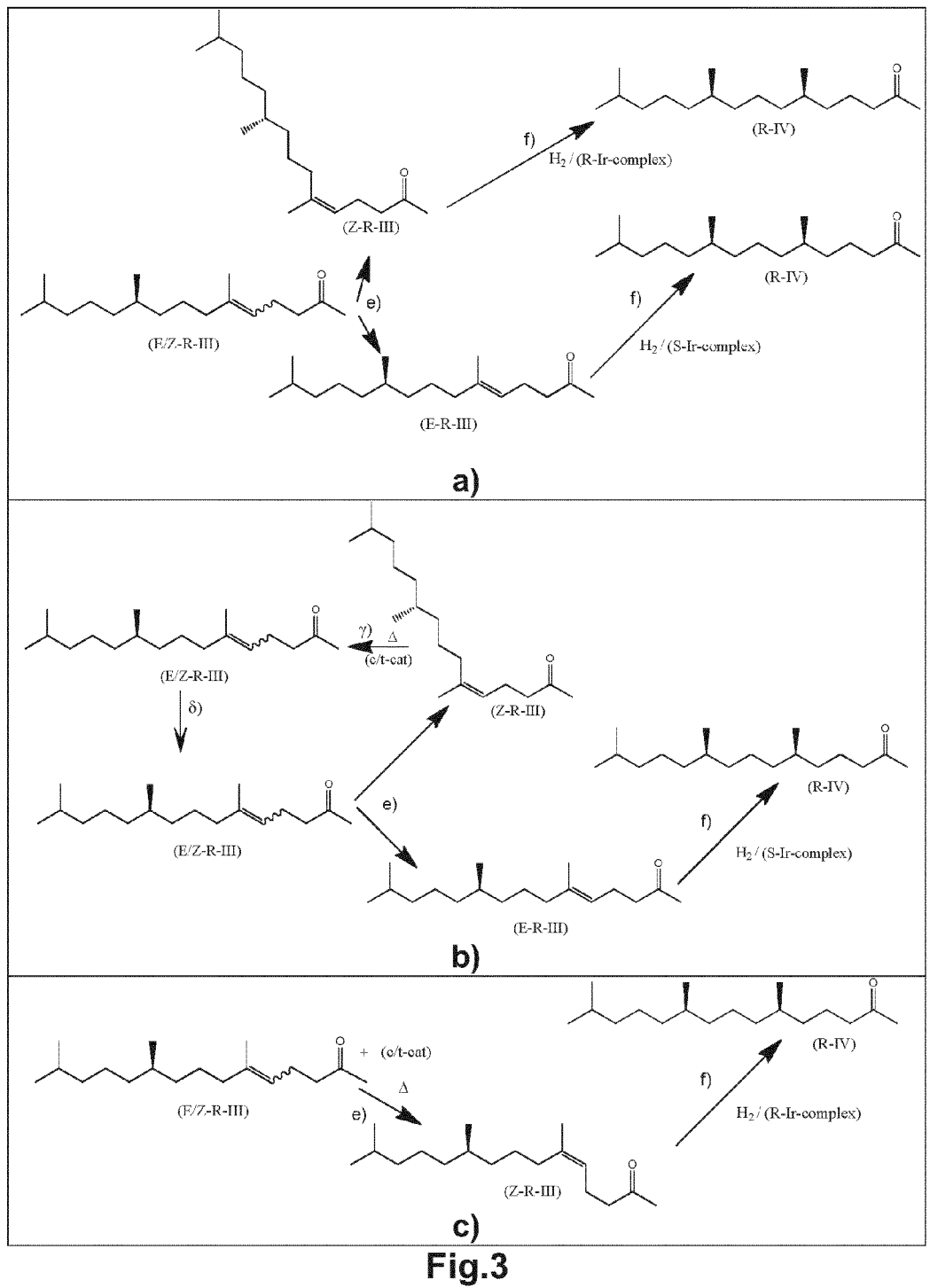
Figure 4:
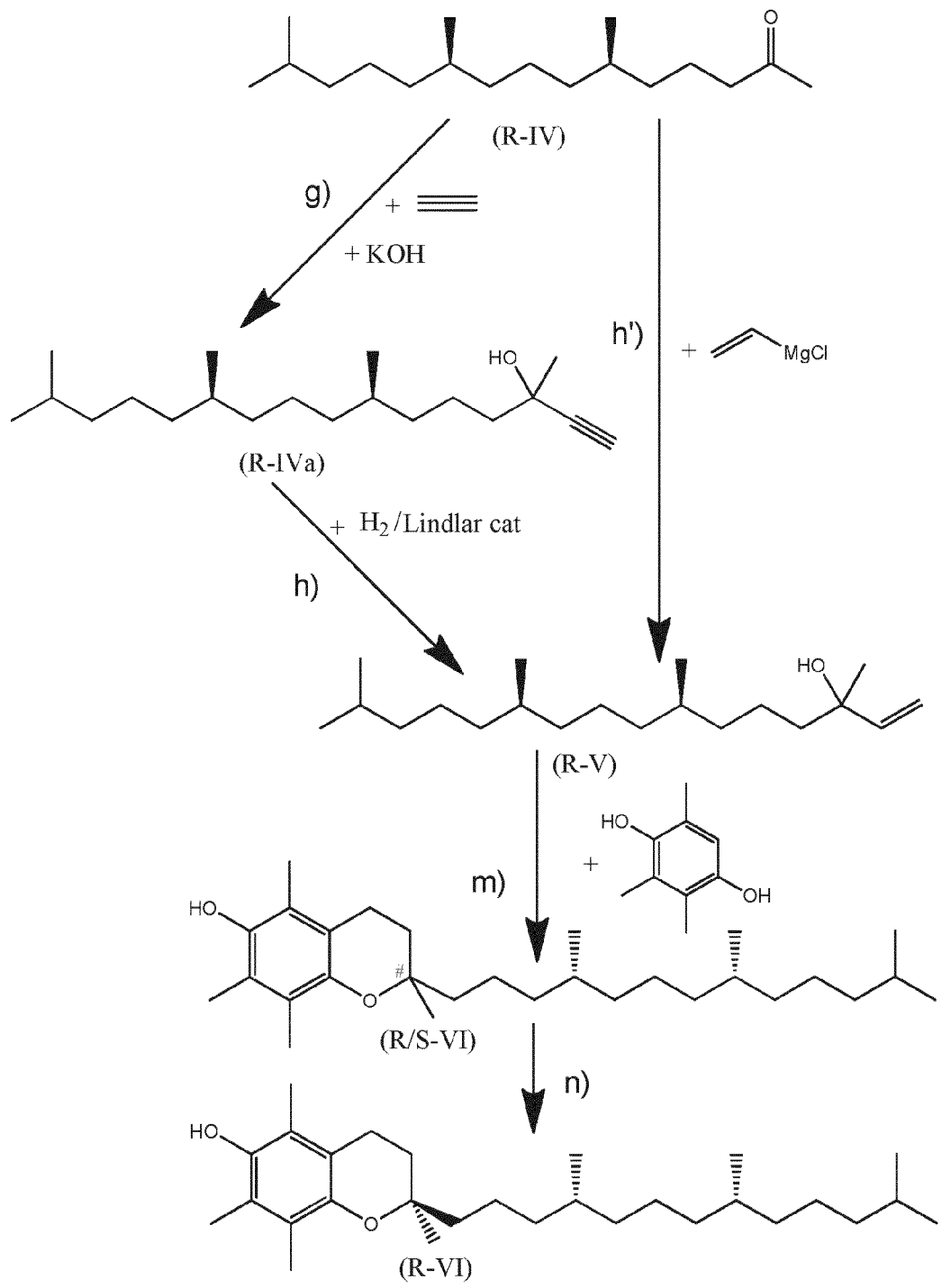
FIG. 4 shows the subsequent steps from (6R,10R)-6,10,14-trimethylpentadecan-2-one to (R,R)-isophytol, (2-ambo)-α-tocopherol and (2R,4'R,8'R)-α-tocopherol, respectively.

The FIGS. 1 to 3 show the subsequent steps from both 6,10-dimethylundec-5-en-2-one and 6,10-dimethylundeca-5,9-dien-2-one to (6R,10R)-6,10,14-trimethylpentadecan-2-one with FIG. 4 showing the subsequent steps from (6R,10R)-6,10,14-trimethylpentadecan-2-one to (R,R)-isophytol, (2-ambo)-α-tocopherol and (2R,4'R,8'R)-α-tocopherol, respectively.

The reference signs in parentheses in the figures, such as (R-II) are used for identification purposes as described below and are not to be confused with the indication of formula such as (II) used in the rest of this document.

In FIG. 1, three different possibilities for the synthesis of (R)-6,10-dimethylundecan-2-one (R-II) are schematically shown (FIG. 1a), 1b), 1c)). As a first step a) for all possibilities shown in FIG. 1, a mixture of (E)-6,10-dimethylundec-5-en-2-one and (Z)-6,10-dimethylundec-5-en-2-one or a mixture of (E)-6,10-dimethylundeca-5,9-dien-2-one and (Z)-6,10-dimethylundeca-5,9-dien-2-one (E/Z-I) is provided. In FIG. 1a) the E-isomer (E-I) (i.e. (E)-6,10-dimethylundec-5-en-2-one or (E)-6,10-dimethylundeca-5,9-dien-2-one, respectively) and the corresponding Z-isomer (Z-I) (i.e (Z)-6,10-dimethylundec-5-en-2-one or (Z)-6,10-dimethylundeca-5,9-dien-2-one, respectively) are separated in step b) from the mixture provided in step a). The separation in step b) is preferably done by distillation over a column. In step c) the Z-isomer is asymmetrically hydrogenated with a specific chiral iridium complex, whereas the E-isomer is asymmetrically hydrogenated with the corresponding enantiomeric chiral iridium complex. A preferred chiral iridium complex is the one of formula (III). The E-isomer (E-I) is asymmetrically hydrogenated using molecular hydrogen in the presence of the chiral iridium complex of formula (IIIa) (S-Ir-complex) having the S-configuration at the stereogenic centre indicated by * in formula (III). The Z-isomer (Z-I), on the other hand, is asymmetrically hydrogenated using molecular hydrogen in the presence of the chiral iridium complex of formula (IIIb) (R-Ir-complex) having the R-configuration at the stereogenic centre indicated by * in formula (III). Both asymmetric hydrogenation routes furnish the same product, i.e. (R)-6,10-dimethylundecan-2-one (R-II). The double bond at position 9 of 6,10-dimethylundeca-5,9-dien-2-one is also hydrogenated during the asymmetric hydrogenation. However, as this double bond is not prochiral, no chiral centre is formed at this position during the hydrogenation.

In FIG. 1b) only one of the isomers (E-isomer (E-I)) (desired isomer) is asymmetrically hydrogenated as described above for FIG. 1a). The other isomer (Z-isomer (Z-I)) (undesired isomer) is subjected to cis/trans isomerization in step α) by addition of a cis/trans isomerization catalyst (c/t-cat) and heating. The cis/trans isomerization catalyst preferably used is a polythiol, particularly of formula (X). By the action of the cis/trans isomerization catalyst the (Z-isomer (Z-I)) is isomerized to a mixture of the E-isomer and the Z-isomer (E/Z-I) which can be added in step p) to the mixture provided in step a). FIG. 1b) shows the process in case the E-isomer is the desired isomer, i.e. the one which is asymmetrically hydrogenated. It is obvious that in case the Z-isomer is the desired isomer, i.e. the one which is asymmetrically hydrogenated, the isomerization process would apply in an analogous way to that of the E-isomer.

In FIG. 1c) only one of the isomers (Z-isomer (Z-I)) (desired isomer) is asymmetrically hydrogenated as described above for FIG. 1a). A cis/trans isomerization catalyst (c/t-cat) is added to the mixture of the E-isomer and the Z-isomer (E/Z-I) provided in step a). In step b) the separation of the (desired) isomer (Z-isomer (Z-I)) is done by distillation in the presence of the cis/trans isomerization catalyst in a (one-pot isomerization or in-situ isomerization). As the desired isomer is separated by distillation, the remainder, enriched in the higher boiling isomer, is isomerized so that in the distillation vessel a thermodynamic equilibrium between the Z- and E-isomers is formed continuously. This procedure may allow all of the undesired isomer being present in the isomer mixture at the beginning provided in step a) to be converted to the desired isomer. As mentioned, FIG. 1c) shows the Z-isomer to be the desired isomer (i.e. separated and asymmetrically hydrogenated), however, it is obvious that the discussion above applies also analogously to the case where the E-isomer would be the desired isomer.

FIG. 2 shows the subsequent step d). In step d) (R)-6,10-dimethylundecan-2-one (R-II) is chemically transformed to a mixture of (R,E)-6,10,14-trimethylpentadec-5-en-2-one and (R,Z)-6,10,14-trimethylpentadec-5-en-2-one (E/Z-R-III). FIG. 2 also shows the preferred variants of such chemical transformations.

In one of the variants shown in FIG. 2, (7R)-3,7,11-trimethyldodec-1-en-3-ol (R-IIb) is formed from (R)-6,10-dimethylundecan-2-one (R-II) by reacting in a first step, i.e. step d1), (R)-6,10-dimethylundecan-2-one (R-II) with ethyne (acetylene) in the presence of a base (shown is KOH) to yield the intermediate (7R)-3,7,11-trimethyldodec-1-yn-3-ol (R-IIa) and then in second step, i.e. in step d2), reacting with molecular hydrogen in the presence of a Lindlar catalyst.

In another variant (7R)-3,7,11-trimethyldodec-1-en-3-ol (R-IIb) is formed directly by means of reaction with a Grignard reagent. In FIG. 2 vinylmagnesium chloride is shown as Grignard reagent.

Subsequently, two variants for the conversion of (7R)-3,7,11-trimethyldodec-1-en-3-ol (R-IIb) to the mixture of (R,E)-6,10,14-trimethylpentadec-5-en-2-one and (R,Z)-6,10,14-trimethylpentadec-5-en-2-one (E/Z-R-III) are shown in FIG. 2. In the first variant, (7R)-3,7,11-trimethyldodec-1-en-3-ol (R-IIb) is reacted in a Saucy-Marbet reaction (step d3)) with 2-methoxyprop-1-ene to yield a mixture of (R,E)-6,10,14-trimethylpentadec-5-en-2-one and (R,Z)-6,10,14-trimethylpentadec-5-en-2-one (E/Z-R-III). In the second variant, (7R)-3,7,11-trimethyldodec-1-en-3-ol (R-IIb) is reacted with alkyl acetoacetate, preferably methyl acetoacetate, in the presence of a base, preferably sodium acetate, to a mixture of (R,E)-6,10,14-trimethylpentadec-5-en-2-one and (R,Z)-6,10,14-trimethylpentadec-5-en-2-one (E/Z-R-III) (Carroll rearrangement).

FIG. 3 shows the subsequent steps e) and f). FIG. 3 corresponds to the FIG. 1 except that the individual substances are extended by a C5 unit. In analogy, at least one isomer of the mixture of (R,E)-6,10,14-trimethylpentadec-5-en-2-one and (R,Z)-6,10,14-trimethylpentadec-5-en-2-one (E/Z-R-III) is separated in step e) and asymmetrically hydrogenated to (6R,10R)-6,10,14-trimethylpentadecan-2-one (R-IV) in step f).

FIG. 4 shows the subsequent steps from (6R,10R)-6,10,14-trimethylpentadecan-2-one to (R,R)-isophytol, (2-ambo)-α-tocopherol, and (2R,4'R,8'R)-α-tocopherol, respectively.

FIG. 4 shows two variants for the conversion of (6R,10R)-6,10,14-trimethylpentadecan-2-one to (R,R)-isophytol. In the first variant, (R,R)-isophytol (R-V) is formed from (6R,10R)-6,10,14-trimethylpentadecan-2-one (R-IV) by reacting in a first step, i.e. step g), (6R,10R)-6,10,14-trimethylpentadecan-2-one (R-IV) with ethyne (acetylene) in the presence of a base (shown is KOH) to yield the intermediate (7R,11R)-3,7,11,15-tetramethylhexadec-1-yn-3-ol (R-IVa) and then in second step, i.e. in step h), reacting with molecular hydrogen in the presence of a Lindlar catalyst.

In the other variant shown, (R,R)-isophytol (R-V) is formed from (6R,10R)-6,10,14-trimethylpentadecan-2-one (R-IV) by means of reaction with a Grignard reagent. In FIG. 4 vinylmagnesium chloride is shown as Grignard reagent.

(R,R)-isophytol (R-V) can further be condensed in step m) with 2,3,5-trimethylbenzene-1,4-diol to yield (2-ambo)-α-tocopherol (R/S-VI)).

In a further step n) (2R,4'R,8'R)-α-tocopherol (R-VI)) is isolated from the corresponding (2-ambo)-α-tocopherol (R/S-VI). The isolation is preferably done by chromatographic separation by means of a chiral phase.

Figure 5:
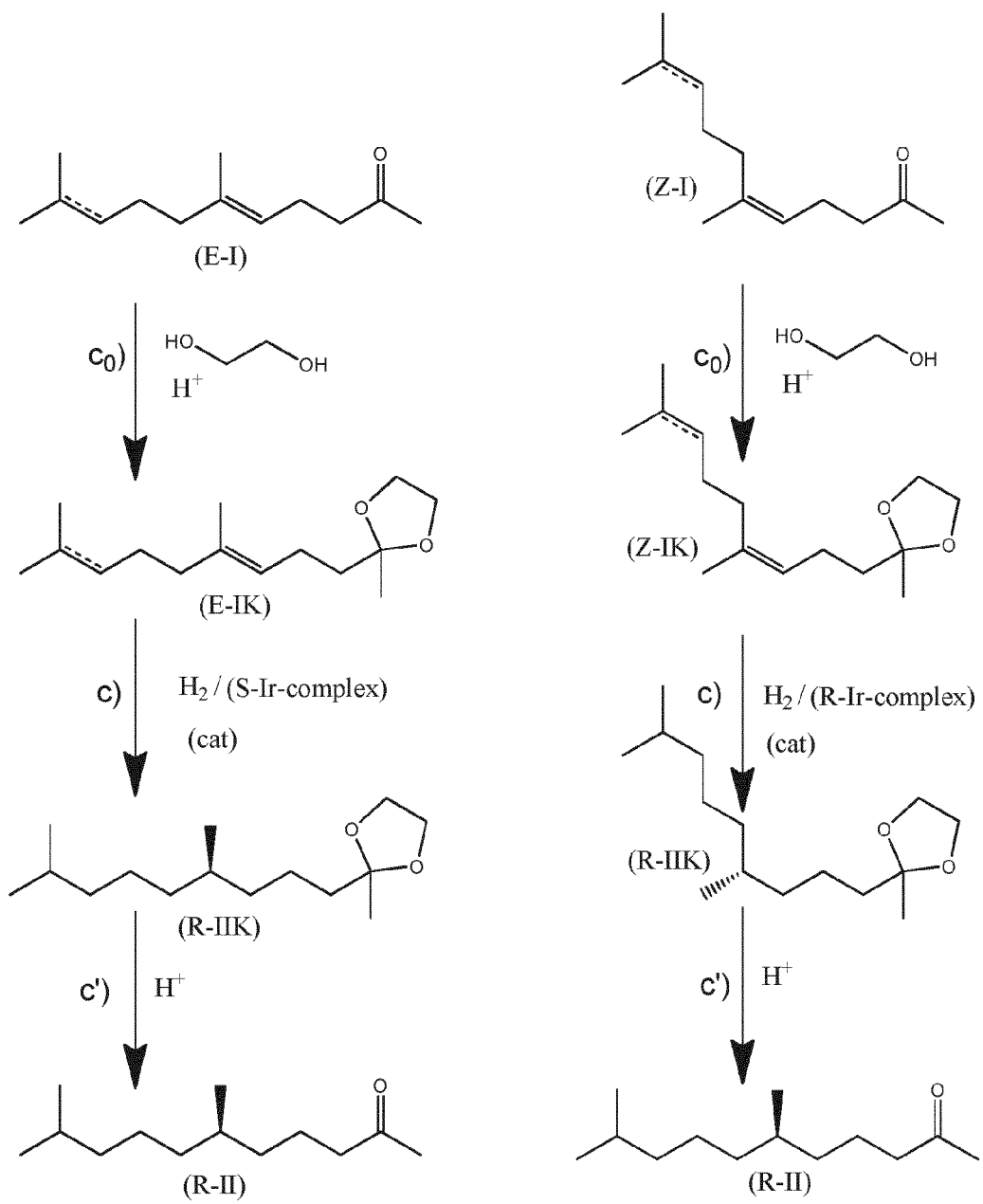
FIGS. 5 and 6 show embodiments of asymmetric hydrogenations relating to the process steps shown in FIGS. 1 and 3, respectively.
Figure 6:
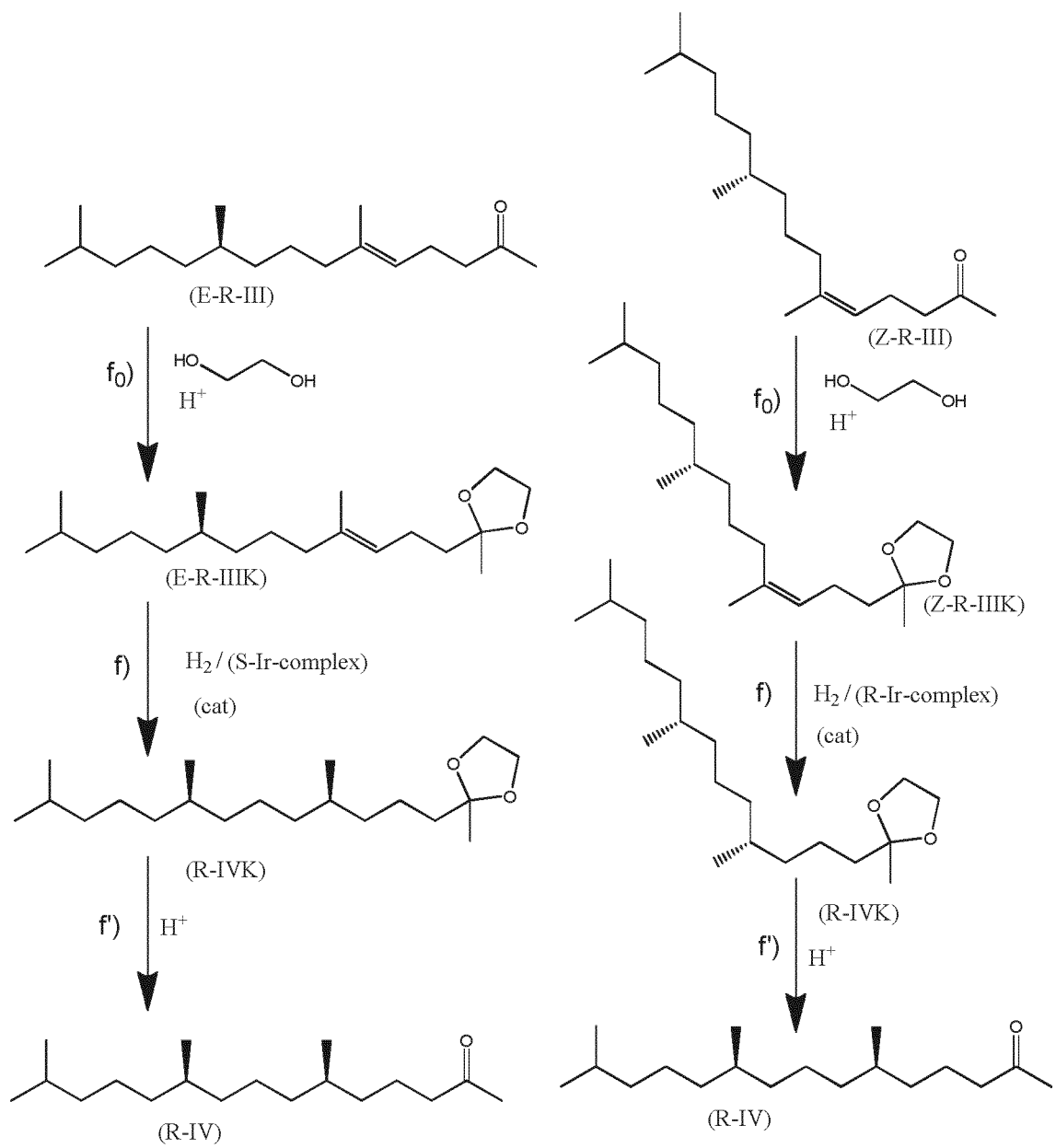

In FIGS. 5 and 6 preferred embodiments of asymmetric hydrogenations are shown. FIG. 5 refers to the process steps in FIG. 1 and FIG. 6 to the process steps of FIG. 3.

The left side of FIG. 5 shows in step $c_0$) the formation of ketals (E-IK) of (E)-6,10-dimethylundec-5-en-2-one or (E)-6,10-dimethylundeca-5,9-dien-2-one (E-I), respectively (which are obtained after separation of the corresponding isomer mixture in step b)) using an alcohol (in FIG. 5 ethylene glycol is shown) in the presence of an acid. The ketal (E-IK), preferably (E)-2-(4,8-dimethylnon-3-en-1-yl)-2-methyl-1,3-dioxolane or (E)-2-(4,8-dimethylnona-3,7-dien-1-yl)-2-methyl-1,3-dioxolane, respectively, is then asymmetrically hydrogenated in step c) as discussed in FIG. 1. The direct product of this asymmetric hydrogenation is an asymmetrically hydrogenated ketal, i.e. preferably (R)-2-(4,8-dimethylnonyl)-2-methyl-1,3-dioxolane (R-IIK), which after acidic hydrolysis in step c') yields (R)-6,10-dimethylundecan-2-one (R-II). On the right side of FIG. 5 the corresponding reaction scheme is shown for the Z-isomer, i.e. (Z)-6,10-dimethylundec-5-en-2-one or (Z)-6,10-dimethylundeca-5,9-dien-2-one (Z-I), respectively, furnishing via the corresponding ketal intermediate, preferably (Z)-2-(4,8-dimethylnon-3-en-1-yl)-2-methyl-1,3-dioxolane or (Z)-2-(4,8-dimethylnona-3,7-dien-1-yl)-2-methyl-1,3-dioxolane (Z-IK), respectively, the same compound (R)-6,10-dimethylundecan-2-one (R-II).

The left side of FIG. 6 shows in step $f_o$) the formation of ketals (E-R-IIK) of (R,E)-6,10,14-trimethylpentadec-5-en-2-one (E-R-III) obtained after isomer separation in step e) using an alcohol (in FIG. 6 ethylene glycol is shown) in the presence of an acid. The ketal (E-R-IIIK), preferably (R,E)-2-methyl-2-(4,8,12-trimethyltridec-3-en-1-yl)-1,3-dioxolane, is then asymmetrically hydrogenated in step f) as discussed in FIG. 3. The direct product of this asymmetric hydrogenation is an asymmetrically hydrogenated ketal, i.e. 2-methyl-2-((4R,8R)-4,8,12-trimethyltridecyl)-1,3-dioxolane (R-IVK), which after acidic hydrolysis in step f') yields (6R,10R)-6,10,14-trimethylpentadecan-2-one (R-IV). On the right side of FIG. 6 the corresponding reaction scheme is shown for the Z-isomer, i.e. (R,Z)-6,10,14-trimethylpentadec-5-en-2-one (Z-R-III), furnishing via the ketal intermediate, preferably (Z,E)-2-methyl-2-(4,8,12-trimethyltridec-3-en-1-yl)-1,3-dioxolane (Z-R-IIIK), the same compound (6R,10R)-6,10,14-triniethylpentadecan-2-one (R-IV).

EXAMPLES

The present invention is further illustrated by the following experiments.

Analytical Methods

GC Determination of E/Z-Ratio and/or Purity of 6,10-dimethylundec-5-en-2-one (DHGA), (R)-6,10-dimethylundecan-2-one (THGA) and (R)-6,10,14-trimethylpentadec-5-en-2-one (R-THFA):

Agilent 6850, column DB-5HT (30 m, 0.25 mm diameter, 0.10 μm film thickness), 107 kPa helium carrier gas). The samples were injected as solutions in hexane, split ratio 300:1, injector temperature 200° C., detector temperature 350° C. Oven temperature program: 100° C. (8 min), 10° C./min to 200° C. (1 min), 20° C./min to 220° C. (4 min), runtime 24 min.

GC Determination of Purity of (6R,10R)-6,10,14-trimethylpentadecan-2-one

Agilent 6850, column DB-5HT (30 m, 0.25 mm diameter, 0.10 μm film thickness), 115 kPa helium carrier gas). The samples were injected as solutions in hexane, split ratio 300:1, injector temperature 200° C., detector temperature 350° C. Oven temperature program: 120° C. (5 min), 14° C./min to 260° C. (2 min), 20° C./min to 280° C. (4 min), runtime 22 min.

GC Determination of Purity of (3RS,7R,11R)-3,7,11,15-tetramethylhexadec-1-en-3-ol ((R,R)-Isophytol)

Agilent 6850 instrument equipped with FID. Agilent DB-5 column (30 m, 0.32 mm diameter, 0.25 μm film thickness) with 25 psi molecular hydrogen carrier gas. The samples were injected as solutions in acetonitrile with a split ratio of 50:1. Injector temperature: 250° C., detector temperature: 350° C. Oven temperature program: 100° C., 4° C./min to 250° C.

GC Determination of E/Z-Ratio and/or Purity of 6,10-dimethylundeca-5,9-dien-2-one and Ketals:

Agilent 6850 instrument, column Agilent DB-5 (123-5032E, 30 m×0.32 mm, film 0.25 μm), the samples were injected as solutions in acetonitrile, split ratio 50:1, injector 250° C., detector 350° C. Oven temperature program: 100° C., 4° C./min until 250° C., 37.5 min total runtime.

| Retention times ($t_R$): | min. |
|---|---|
| (E)-6,10-dimethylundeca-5,9-dien-2-one (E-GA) | 11.0 |
| E-GA-DM | 14.8 |
| E-GA-neo | 20.5 |
| E-GA-tfe | 13.2, pc[1] |
| (Z)-6,10-dimethylundeca-5,9-dien-2-one (Z-GA) | 10.6 |

-continued

| Retention times ($t_R$): | min. |
|---|---|
| Z-GA-DM | 14.0, pc[1] |
| Z-GA-neo | 19.5 |
| E-DHGA-DM | 14.1, pc[1] |
| E-DHGA-neo | 19.6, pc[1] |
| E-DHGA-tfe | 12.5 |
| Z-DHGA-DM | 13.0, pc[1] |
| Z-DHGA-neo | 18.5, pc[1] |
| R,E-THFA-DM | 24.2, pc[1] |
| R,E-THFA-neo | 29.1 |
| R,Z-THFA-DM | 23.1, pc[1] |
| R,Z-THFA-neo | 27.9 |
| R-THGA-DM | 13.1 |
| R-THGA-neo | 18.9 |
| R-THGA-tfe | 11.8 |
| RR-C18-DM | decomp.[2] |
| RR-C18-neo | 28.5 |
| RR-C18-tfe | 21.4 |

[1] pc = partial decomposition
[2] decomp. = decomposition during GC analysis

Analysis of the Asymmetrically Hydrogenated Reaction Products

The corresponding dimethyl, ethylene glycol, neopentyl and bis(trifluoroethyl) ketals were hydrolyzed to the ketones in the presence of aqueous acid and analyzed for conversion and their stereoisomer ratio using the following methods for ketones.

The conversion of the hydrogenation reaction was determined by gas chromatography using an achiral column.

Method for Conversion:

Agilent 7890A GC equipped with FID. Agilent HP-5 column (30 m, 0.32 mm diameter, 0.25 µm film thickness) with 25 psi molecular hydrogen carrier gas. The samples were injected as solutions in dichloromethane with a split ratio of 10:1. Injector temperature: 250° C., detector temperature: 300° C. Oven temperature program: 50° C. (2 min) then 15° C./min to 300° C., hold 5 min.

For the determination of the isomer ratio, the hydrogenated ketones can be reacted with either (+)-diisopropyl-O,O'-bis(trimethylsilyl)-L-tartrate or (−)-diisopropyl-O,O'-bis(trimethylsilyl)-D-tartrate in the presence of trimethylsilyl triflate [$Si(CH_3)_3(OSO_2CF_3)$] to form the diastereomeric ketals as described in A. Knierzinger, W. Walther, B. Weber, R. K. Müller, T. Netscher, *Helv. Chin. Acta* 1990, 73, 1087-1107. The ketals can be analysed by gas chromatography using an achiral column to determine the isomer ratios. For the hydrogenated ketone 6,10-dimethylundecan-2-one, either D-(−)- or L-(+)-diisopropyltartrate can be used. For 6,10,14-trimethylpentadecan-2-one, L-(+)-diisopropyltartrate can be used to measure the quantity of the (6R,10R)-isomer that was present. D-(−)-diisopropyltartrate can be used to determine the amount of the (6S,10S)-isomer. Thus the selectivity of the stereoselective hydrogenation can be determined indirectly.

Method for Determination of Isomers:

Agilent 6890N GC with FID. Agilent CP-Sil88 for FAME column (60 m, 0.25 mm diameter, 0.20 µm film thickness) with 16 psi molecular hydrogen carrier gas. The samples were injected as solutions in ethyl acetate with a split ratio of 5:1. Injector temperature: 250° C., FID detector temperature: 250° C. Oven temperature program: 165° C. (isothermal, 240 min)

The Ir complexes indicated in the following experiments are prepared according to the disclosure in *Chem. Sci.*, 2010, 1, 72-78.

Experiment E1

Separation of E/Z Isomer Mixtures of 6,10-dimethylundec-5-en-2-one (Step b)

7.02 kg of 6,10-dimethylundec-5-en-2-one was prepared according to example 10 of DE 1 193 490 and was analysed by the GC method given above to be a 57%/43% mixture of (E)-6,10-dimethylundec-5-en-2-one and (Z)-6,10-dimethylundec-5-en-2-one (99% purity).

The mixture was distilled using separation equipment consisting of a still (volume: 9 liter) with a falling film evaporator, a rectifying column (70 mm inner diameter, height 5 m). The column was equipped with a very efficient structured packing (Sulzer). The mixture was rectified at a top pressure of approx. 5 mbar and at a column top temperature in the range from 105 to 112° C. and a bottom temperature in the still of about 125° C. The reflux ratio was adjusted to 20.

Fractions containing (Z)-6,10-dimethylundec-5-en-2-one (content of Z-isomer=99%, E-isomer<1%) as well as fractions containing (E)-6,10-dimethylundec-5-en-2-one (content of E-isomer 97%, Z-isomer<3%) were collected. At the end (E)-6,10-dimethylundec-5-en-2-one (content of E-isomer=99.5%, Z-isomer=0.5%) was found left in the still.

Experiment E2

Asymmetric Hydrogenations of 6,10-dimethylundec-5-en-2-one or 6,10-dimethylundeca-5,9-dien-2-one (Step c)

Both isomers (E)-6,10-dimethylundec-5-en-2-one (E-DHGA) (E/Z=99.5/0.5) and (Z)-6,10-dimethylundec-5-en-2-one (Z-DHGA) (Z/E=99/1) were hydrogenated asymmetrically, separate from each other in the following manner:

A 2 L autoclave was charged with 70 g (0.353 mol) of the specific isomer, 700 mL of 2,2,2-trifluoroethanol and a solution of the chiral iridium complex of formula (III-F) having the chirality given in table 2 at the centre indicated by * in said formula (570 mg, 0.356 mmol, 0.1 mol %) in anhydrous dichloromethane (10 g). The autoclave was closed and a pressure of 50 bar of molecular hydrogen was applied. The reaction mixture was heated to 30° C. whilst stirring for 2 hours. Afterwards the pressure was released and the solvent was removed. The product formed is (R)-6,10-dimethylundecan-2-one. The conversion as well as the amount of isomers formed is determined as indicated above and the results are given in table 2. The products of the two separate asymmetric hydrogenations have been combined.

TABLE 2

Asymmetric hydrogenation of E-DHGA and Z-DHGA.

|  | E-DHGA | Z-DHGA |
|---|---|---|
| Formula of Ir complex | III-F | III-F |
| Configuration of chiral Ir complex at * | S | R |
| Amount of chiral Ir complex [mol-%] | 0.1 | 0.1 |
| Conversion [%] | >99 | >99 |
| (R)-6,10-dimethylundecan-2-one [%] | 95.8 | 93.3 |
| (S)-6,10-dimethylundecan-2-one [%] | 4.2 | 6.7 |

In a further experiment 0.25 mmol of (E)-6,10-dimethylundeca-5,9-dien-2-one (E-GA) or (E)-6,10-dimethylundec-5-en-2-one (E-DHGA) and 0.5 mol-%, respectively 1 mol- %, of the Ir complex of the formula given in table 2a and 1.25 ml of absolute (dry) dichloromethane were put in an autoclave. The autoclave was closed and a pressure of 50 bar of molecular hydrogen was applied. Under stirring the reaction solution was kept at room temperature for 14 hours. Afterwards the pressure was released and the solvent removed. For determining the conversion the crude product was analysed by achiral gas chromatography without any further purification. The amount for the isomers has been determined using the above method.

TABLE 2a

Asymmetric hydrogenation of E-GA or E-DHGA.

|  | 1 E-GA | 2 E-GA | 3 E-DHGA | 4 E-DHGA |
|---|---|---|---|---|
| Formula of Ir complex | III-F | III-C | III-D | III-C |
| Configuration of chiral Ir complex at * | S | S | S | S |
| Amount of chiral Ir complex [mol-%] | 0.5 | 0.5 | 1 | 1 |
| Conversion [%] | 100 | 100 | 100 | 100 |
| Isomer-Distribution |  |  |  |  |
| (6R)-6,10-dimethyl-undecan-2-one [%] | 96.5 | >98 | 98.6 | 98.9 |
| (6S)-6,10-dimethyl-undecan-2-one [%] | 3.5 | <2 | 1.4 | 1.1 |

In two further experiments in an autoclave 0.25 mmol of (E)-6,10-dimethylundec-5-en-2-one (E-DHGA) or (Z)-6,10-dimethylundec-5-en-2-one (Z-DHGA) and 1 mol-% of the Ir complex of the formula given in table 2b or 2c or 2d and 1.25 ml of absolute (dry) solvent as indicated in table 2b or 2c were put. The autoclave was closed and a pressure of 50 bar of molecular hydrogen was applied. Under stirring the reaction solution was kept at room temperature for 16 hours. Afterwards the pressure was released and the solvent removed. For determining the conversion the crude product was analyzed by achiral gas chromatography without any further purification. The amount for the isomers has been determined using the above method.

TABLE 2b

Asymmetric hydrogenation of E-DHGA with different Ir complexes.

|  | 5 E-DHGA | 6 E-DHGA | 7 E-DHGA | 8 E-DHGA |
|---|---|---|---|---|
| Formula of Ir complex | III-D | III-C | III-D | III-A'[2] |
| Configuration of chiral Ir complex at * | R | S | R | S |
| Amount of chiral Ir complex [mol-%] | 1 | 1 | 1 | 1 |
| Solvent[1] | TFE | DCM | DCM | DCM |
| Conversion [%] | >99 | >99 | >99 | >99 |
| Isomer-Distribution |  |  |  |  |
| (6R)-6,10-dimethylundecan-2-one [%] | 0.7 | 98.9 | 1.4 | 89.1 |
| (6S)-6,10-dimethylundecan-2-one [%] | 99.3 | 1.1 | 98.6 | 10.9 |

[1]TFE = 2,2,2-trifluoroethanol; DCM = dichloromethane
[2]chiral Ir complex of formula (III-A'):

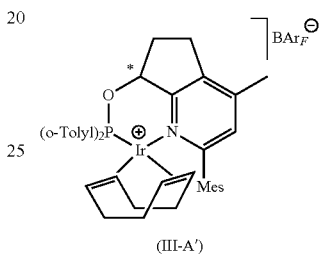

(III-A')

TABLE 2c

Asymmetric hydrogenation of E-DHGA with different Ir complexes.

|  | 9 E-DHGA | 10 E-DHGA | 11 E-DHGA |
|---|---|---|---|
| $X^1=X^2$ in formula of Ir complex[1] | ![F-phenyl] | ![naphthyl] | ![OMe-phenyl] |
| Configuration of chiral Ir complex at * | (S) | (S) | (S) |
| Amount of chiral Ir complex [mol-%] | 1 | 1 | 1 |
| Solvent[1] | DCM | DCM | DCM |
| Conversion [%] | >99 | >99 | >99 |
| Isomer-Distribution |  |  |  |
| (6R)-6,10-dimethyl-undecan-2-one [%] | 94.5 | 94.2 | 90.6 |
| (6S)-6,10-dimethyl-undecan-2-one [%] | 5.5 | 5.8 | 9.4 |

[1]chiral Ir complex of formula

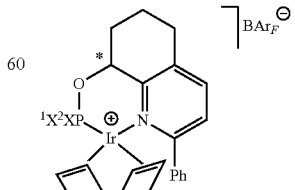

[2]TFE = 2,2,2-trifluoroethanol; DCM = dichloromethane

TABLE 2d

Asymmetric hydrogenation of Z-DHGA with different Ir complexes.

|  | 12 Z-DHGA | 13 Z-DHGA | 14 Z-DHGA | 15 Z-DHGA |
|---|---|---|---|---|
| Formula of Ir complex | III-D | III-D | III-C | III-A'[2] |
| Configuration of chiral Ir complex at * | R | S | S | S |
| Amount of chiral Ir complex [mol-%] | 1 | 1 | 1 | 1 |
| Solvent[1] | TFE | DCM | DCM | DCM |
| Conversion [%] | >99 | >99 | >99 | >99 |
| Isomer-Distribution |  |  |  |  |
| (6R)-6,10-dimethylundecan-2-one [%] | 99.3 | 1.7 | 2.1 | 11.1 |
| (6S)-6,10-dimethylundecan-2-one [%] | 0.7 | 98.3 | 97.9 | 88.9 |

[1] TFE = 2,2,2-trifluoroethanol; DCM = dichloromethane
[2] chiral Ir complex of formula (III-A'):

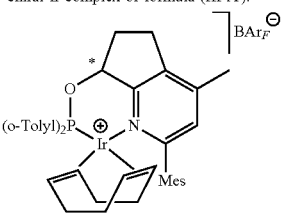

Experiment E2a

Preparation of Ketals of 6,10-dimethylundec-5-en-2-one or 6,10-dimethylundeca-5,9-dien-2-one (Step $c_o$)

a) Preparation of Dimethyl Ketals 6,10-dimethylundec-5-en-2-one or 6,10-dimethylundeca-5,9-dien-2-one (170.5 mmol) was added to trimethyl orthoformate (50.8 mL, 49.2 g, 451 mmol, 2.65 eq.) and cooled to 5° C. Sulfuric acid (96%, 32.3 mg, 0.29 mmol, 0.2 mol %) in MeOH (16 mL) was added within 5 min. Subsequently, the reaction was heated to reflux (65° C. IT) for 3 h. After cooling, thin layer chromatography (TLC) analysis indicated full conversion. NaOMe (0.24 mL of a 25% solution in MeOH) was added to neutralize the acid. The mixture was concentrated in vacuo and subsequently diluted with hexane (50 mL). The developed precipitate was filtered off and the filtrate was concentrated. The crude product was purified by distillation, furnishing the desired dimethyl ketal.

The characterization of the ketal is given in detail hereafter.

TABLE 2 d(i)

Preparation of dimethyl ketals.

|  | E-GA-DM | Z-GA-DM | E-DHGA-DM | Z-DHGA-DM |
|---|---|---|---|---|
| Ketone | (E)-6,10-dimethyl-undeca-5,9-dien-2-one | (Z)-6,10-dimethyl-undeca-5,9-dien-2-one | (E)-6,10-dimethyl-undec-5-en-2-one | (Z)-6,10-dimethyl-undec-5-en-2-one |
| Ketal | (E)-10,10-dimethoxy-2,6-dimethylundeca-2,6-diene | (Z)-10,10-dimethoxy-2,6-dimethylundeca-2,6-diene | (E)-2,2-dimethoxy-6,10-dimethylundec-5-ene | (Z)-2,2-dimethoxy-6,10-dimethylundec-5-ene |
| Yield [%] | 87 | 73 | 91 | 98 |
| E/Z | 99.4/0.6 | 1.6/98.4 | 95.4/4.6 | 0.4/99.6 |

Characterization Data (E)-10,10-dimethoxy-2,6-dimethylundeca-2,6-diene (E-GA-DM)

$^1$H NMR (300 MHz, CDCl$_3$): δ 1.26 (s, 3H), 1.58 (s, 3H), 1.60 (s, 3H), superimposed by 1.60-1.65 (m, 2H), 1.66 (br s, 3H), 1.92-2.09 (m, 6H), 3.17 (s, 6H), 5.02-5.14 (m, 2H) ppm.
$^{13}$C NMR (75 MHz, CDCl$_3$): δ 15.9 (1C), 17.6 (1C), 20.8 (1C), 22.8 (1C), 25.6 (1C), 26.6 (1C) 36.4 (1C), 39.6 (1C), 47.9 (2C), 101.4 (1C), 123.8 (1C), 124.2 (1C), 131.2 (1C), 135.1 (1C) ppm.
MS (EI, m/z): 240 (M$^+$, <1), 225.3 [(M-CH$_3$)$^+$, 1], 209.3 [(M-CH$_3$O)$^+$, 20], 193.3 (8), 176.2 (18), 161.2 (16), 139.2 (20), 123.2 (14), 107.2 (75), 89.2 (100), 69.2 (65), 41.1 (56).
IR (cm$^{-1}$): 2928 (m), 2857 (w), 2828 (w), 1670 (w), 1452 (m), 1376 (s), 1345 (w), 1302 (w), 1262 (w), 1222 (w), 1196 (m), 1172 (m), 1123 (s), 1102 (s), 1053 (s), 985 (w), 929 (w), 854 (s), 744 (w), 619 (w).

(Z)-10,10-dimethoxy-2,6-dimethylundeca-2,6-diene (Z-GA-DM)

$^1$H NMR (300 MHz, CDCl3): δ 1.27 (s, 3H), 1.56-1.65 (m, 5H), 1.68 (br. s, 6H), 1.96-2.09 (m, 6H), 3.17 (s, 6H), 5.11 (t, J=7.2 Hz, 2H) ppm.
$^{13}$C NMR (75 MHz, CDCl$_3$): δ 17.6 (1C), 20.9 (1C), 22.7 (1C), 23.3 (1C), 25.7 (1C), 26.6 (1C), 31.9 (1C), 36.7 (1C), 48.0 (2C), 101.4 (1C), 124.2 (1C) 124.6 (1C), 131.5 (1C), 135.4 (1C) ppm.
MS (EI, m/z): No GC-MS was obtained due to decomposition on the column.
IR (cm$^{-1}$): 2943 (m), 2858 (w), 2828 (w), 1451 (m), 1376 (m), 1348 (w), 1301 (w), 1261 (w), 1197 (m), 1172 (m), 1153 (w), 1120 (s), 1098 (m), 1053 (s), 929 (w), 854 (m), 833 (m), 745 (w), 622 (w).

(E)-2,2-dimethoxy-6,10-dimethylundec-5-ene (E-DHGA-DM)

$^1$H NMR (300 MHz, CDCl$_3$): δ 0.83 (d, J=6.6 Hz, 6H), 1.02-1.13 (m, 2H), 1.24 (s, 3H), 1.27-1.39 (m, 2H), 1.49 (tqq, J=6.4, 6.4, 6.4 Hz, 1H), superimposed by 1.53-1.63 (m, 2H), superimposed by 1.56 (s, 3H), 1.87-2.03 (m, 4H), 3.13 (s, 6H), 5.07 (tq, J=7.0, 1.4 Hz, 1H) ppm.
$^{13}$C NMR (75 MHz, CDCl$_3$): δ 16.1 (1C), 21.2 (1C), 23.0 (2C), 23.2 (1C), 26.0 (1C), 28.2 (1C), 36.9 (1C), 39.0 (1C), 40.2 (1C), 48.3 (2C), 101.8 (1C), 124.0 (1C), 135.9 (1C) ppm.
MS (EI, m/z): No GC-MS was obtained due to decomposition on the column.
IR (cm$^{-1}$): 2953 (s), 2931 (s), 2870 (m), 2828 (m), 2108 (w), 1668 (w), 1460 (m), 1377 (s), 1367 (w), 1345 (w), 1301 (w), 1262 (m), 1221 (m), 1198 (m), 1172 (s), 1119 (s), 1100 (s), 1077 (s), 1053 (s), 967 (w), 927 (w), 854 (w), 796 (w), 739 (w), 620 (w).

6Z)-2,2-di meth oxy-6,10-di methylundec-5-ene (Z-DHGA-DM)

$^1$H NMR (300 MHz, CDCl$_3$): δ 0.88 (d, J=6.6 Hz, 6H), 1.12-1.21 (m, 2H), 1.28 (s, 3H), 1.32-1.43 (m, 2H), 1.53 (dspt, J=6.6, 6.6 Hz, 1H), 1.57-1.66 (m, 2H), 1.68 (q, J=1.1 Hz, 3H), 1.94-2.06 (m, 4H), 3.18 (s, 6H), 5.10 (t, J=6.8 Hz, 1H) ppm.

$^{13}$C NMR (75 MHz, CDCl$_3$): δ 20.9 (1C), 22.6 (2C), 22.7 (1C), 23.3 (1C), 25.8 (1C), 27.9 (1C), 31.9 (1C), 36.8 (1C), 38.9 (1C), 48.0 (2C), 101.5 (1C), 124.3 (1C), 135.9 (1C) ppm.

MS (EI, m/z): No GC-MS was obtained due to decomposition on the column.

IR (cm$^{-1}$): 2953 (s), 2870 (w), 2828 (w), 1461 (w), 1376 (m), 1301 (w), 1261 (w), 1205 (m), 1172 (m), 1119 (m), 1097 (m), 1074 (m), 1053 (s), 1022 (w), 927 (w), 854 (m), 738 (w), 621 (w).

b) Preparation of Ethylene Glycol Ketals

Under nitrogen, a reaction vessel was charged with glycol (112 mL, 125 g, 2.1 mol), p-toluenesulfonic acid monohydrate (0.150 g, 0.5774 mmol) and 0.5 mol either of (E)-6,10-dimethylundec-5-en-2-one or (Z)-6,10-dimethylundec-5-en-2-one. The mixture was allowed to stir at ambient temperature for 5 hours at reduced pressure (0.39 mbar). While maintaining the low pressure, the temperature was slowly increased to 40° C. At conversion of larger than 95% of the ketone, the temperature was further increased allowing a gentle distillation of glycol and continued until a conversion of more than 99% was achieved.

At room temperature, the product was extracted by a solution of triethylamine in heptane (2 mL triethylamine/L heptane). The glycol phase was separated and the heptane layer was washed with a NaHCO$_3$ solution in water. Separation of the heptane phase, drying over anhydrous Na$_2$SO$_4$, filtration and removal of the solvent in vacuo gave the crude ketal. The ketal was further purified by means of distillation. The corresponding ketal was identified by $^1$H-NMR.

TABLE 2 d(ii)

| Preparation of ethylene glycol ketals. | | |
|---|---|---|
| | E-DHGA-en | Z-DHGA-en |
| Ketone | (E)-6,10-dimethylundec-5-en-2-one | (Z)-6,10-dimethylundec-5-en-2-one |
| Ketal | (E)-2-(4,8-dimethylnon-3-en-1-yl)-2-methyl-1,3-dioxolane | (Z)-2-(4,8-dimethylnon-3-en-1-yl)-2-methyl-1,3-dioxolane |
| Yield [%] | 88 | 87 |

Characterization Data (E)-2-(4,8-dimethylnon-3-en-1-yl)-2-methyl-1,3-dioxolane (E-DHGA-en)

$^1$H NMR (300 MHz, CDCl$_3$) δ 5.12 (t, 1H), 3.95 (m, 4H), 2.2-2 (m, 2H), 1.94 (t, 2H), 1.8-1.3 (m, 11H), 1.2-1.0 (m, 2H), 0.87 (d, 6H) ppm.

(Z)-2-(4,8-dimethylnon-3-en-1-yl)-2-methyl-1,3-dioxolane (Z-DHGA-en)

$^1$H NMR (300 MHz, CDCl$_3$) δ 5.12 (t, 1H), 3.94 (m, 4H), 2.15-1.9 (m, 4H), 1.7-1.45 (m, 6H), 1.44-1.27 (m, 5H), 1.23-1.08 (m, 2H), 0.88 (d, 6H) ppm.

c) Preparation of Neopentyl Glycol Ketals

The ketone (90.7 mmol) indicated in table 2 d(iii), 2,2-dimethyl-1,3-propanediol (neopentylglycol, 32.4 g, 283 mmol, 3.4 eq.) and p-toluene sulfonic acid monohydrate (60 mg, 0.31 mmol, 0.3 mol %) were suspended in toluene (300 mL). The reaction was heated to 90° C. upon which a homogeneous solution formed. Subsequently, at 75° C., vacuum was applied cautiously (first 63 mbar, then 24 mbar) in order to slowly distill toluene off (approx. 100 mL over 4 h). After 4 h, thin layer chromatography (TLC) analysis indicated full conversion of the ketone. The reaction was allowed to cool to room temperature and diluted with heptane (300 mL) upon which excess neopentylglycol precipitated. The precipitate was filtered off (17.4 g wet). The filtrate was treated with Et$_3$N (1 mL), subsequently washed with aqueous NaHCO$_3$ solution (2.4% w/w, 2×300 mL), dried over MgSO$_4$ and concentrated in vacuo. The crude product was purified by distillation, furnishing the desired neopentyl ketal. The characterization of the ketal is given in detail hereafter.

TABLE 2 d(iii)

| Preparation of neopentyl glycol ketals. | | | | |
|---|---|---|---|---|
| | E-GA-neo | Z-GA-neo | E-DHGA-neo | Z-DHGA-neo |
| Ketone | (E)-6,10-dimethyl-undeca-5,9-dien-2-one | (Z)-6,10-dimethyl-undeca-5,9-dien-2-one | (E)-6,10-dimethyl-undec-5-en-2-one | (Z)-6,10-dimethyl-undec-5-en-2-one |
| Ketal | (E)-2-(4,8-dimethyl-nona-3,7-dien-1-yl)-2,5,5-trimethyl-1,3-dioxane | (Z)-2-(4,8-dimethyl-nona-3,7-dien-1-yl)-2,5,5-trimethyl-1,3-dioxane | (E)-2-(4,8-dimethyl-non-3-en-1-yl)-2,5,5-trimethyl-1,3-dioxane | (Z)-2-(4,8-dimethyl-non-3-en-1-yl)-2,5,5-trimethyl-1,3-dioxane |
| Yield [%] | 78 | 87 | 89 | 84 |
| E/Z | 99.4/0.6 | 1.7/98.3 | 95.3/4.7 | 1.6/98.4 |

Characterization Data (E)-2-(4,8-dimethylnona-3,7-dien-1-yl)-2,5,5-trimethyl-1,3-dioxane (E-GA-neo)

$^1$H NMR (300 MHz, CDCl$_3$): δ 0.92 (s, 3H), 0.99 (s, 3H), 1.37 (s, 3H), 1.59 (s, 3H), 1.61 (s, 3H), 1.67 (s, 3H), 1.68-1.75 (m, 2H), 1.94-2.15 (m, 6H), AB signal (δ$_A$=3.46, δ$_B$=3.52, J$_{AB}$=11.3 Hz, 4H), 5.05-5.17 (m, 2H) ppm.

$^{13}$C NMR (75 MHz, CDCl$_3$): δ 15.9 (1C), 17.6 (1C), 20.8 (1C), 22.0 (1C), 22.6 (1C), 22.7 (1C), 25.6 (1C), 26.7 (1C), 29.9 (1C), 37.3 (1C), 39.6 (1C), 70.3 (2C), 98.8 (1C), 124.1 (1C), 124.3 (1C), 131.2 (1C), 135.1 (1C) ppm.

MS (EI, m/z): 280 (M$^+$, 3), 265 [(M-CH$_3$)$^+$, 14], 176 (21), 129 [(C$_7$H$_{13}$O$_2$)$^+$, 100], 69 (63), 43 (43).

IR (cm$^{-1}$): 2954 (m), 2925 (m), 2858 (m), 2731 (w), 1720 (w), 1669 (w), 1473 (w), 1450 (m), 1394 (m), 1372 (m), 1349 (w), 1306 (w), 1271 (w), 1249 (m), 1211 (m), 1186 (m), 1123 (s), 1088 (s), 1043 (m), 1021 (m), 984 (w), 950 (w), 925 (w), 907 (w), 862 (m), 837 (m), 792 (w), 742 (w), 677 (w), 667 (w).

(Z)-2-(4,8-dimethylnona-3,7-dien-1-yl)-2,5,5-trimethyl-1,3-dioxane (Z-GA-neo)

$^1$H NMR (300 MHz, CDCl$_3$): δ 0.91 (s, 3H), 0.97 (s, 3H), 1.35 (s, 3H), 1.60 (s, 3H), 1.64-1.74 (m, 5H) superimposed by 1.67 (br s, 3H), 1.99-2.18 (m, 6H), AB signal ($\delta_A$=3.44, $\delta_B$=3.51, $J_{AB}$=11.3 Hz, 4H), 5.07-5.16 (m, 2H) ppm.

$^{13}$C NMR (75 MHz, CDCl$_3$): δ 17.5 (1C), 20.9 (1C), 21.3 (1C), 21.9 (1C), 22.5 (1C), 22.6 (1C), 23.3 (1C), 25.7 (1C), 26.6 (1C), 29.9 (1C), 31.8 (1C), 37.5 (1C), 70.3 (1C), 98.7 (1C), 124.3 (1C), 124.9 (1C), 131.4 (1C), 135.2 (1C) ppm.

MS (EI, m/z): 280 (M$^+$, 3), 265 [(M-CH$_3$)$^+$, 13], 176 (19), 129 [(C$_7$H$_{13}$O$_2$)$^+$, 100], 107 (15), 69 (62), 43 (39).

IR (cm$^{-1}$): 2954 (m), 2927 (m), 2858 (m), 2729 (w), 1721 (w), 1671 (w), 1473 (m), 1450 (m), 1394 (m), 1374 (m), 1349 (w), 1315 (w), 1271 (m), 1249 (m), 1211 (m), 1187 (m), 1149 (w), 1120 (s), 1086 (s), 1043 (m), 1021 (m), 985 (w), 951 (m), 925 (w), 907 (m), 857 (m), 833 (m), 792 (w), 743 (w), 677 (w), 667 (w).

(E)-2-(4,8-dimethylnon-3-en-1-yl)-2,5,5-trimethyl-1,3-dioxane (E-DHGA-neo)

$^1$H NMR (300 MHz, CDCl$_3$): δ 0.87 (d, J=6.6 Hz, 6H), 0.93 (s, 3H), 1.00 (s, 3H), 1.06-1.22 (m, 2H), 1.31-1.43 (m, 2H) superimposed by 1.38 (s, 3H), 1.53 (tqq, J=6.6, 6.6, 6.6 Hz, 1H), 1.61 (br s, 3H), 1.65-1.77 (m, 2H), 1.94 (t, J=7.5 Hz, 2H), 2.05-2.17 (m, 2H), AB signal ($\delta_A$=3.46, $\delta_B$=3.54, $J_{AB}$=11.4 Hz, 4H), 5.13 (tq, J=7.1, 1.1 Hz, 1H) ppm.

$^{13}$C NMR (75 MHz, CDCl$_3$): δ 15.8 (1C), 20.9 (1C), 22.0 (1C), 22.59 (1C), 22.63 (2C), 22.7 (1C), 25.7 (1C), 27.9 (1C), 29.9 (1C), 37.3 (1C), 38.6 (1C), 39.9 (1C), 70.3 (2C), 98.8 (1C), 123.8 (1C), 135.6 (1C) ppm.

MS (EI, m/z): 282 (M$^+$, 5), 267 [(M-CH$_3$)$^+$, 10), 129 (100), 95 (14), 69 (36), 43 (32).

IR (cm$^{-1}$): 2953 (s), 2929 (m), 2868 (m), 1720 (w), 1468 (m), 1394 (m), 1381 (m), 1368 (m), 1349 (w), 1306 (w), 1270 (w), 1250 (m), 1211 (m), 1187 (m), 1118 (s), 1087 (s), 1066 (m), 1044 (m), 1022 (m), 950 (m), 925 (w), 907 (m), 862 (m), 791 (w), 739 (w), 677 (w), 666 (w).

(Z)-2-(4,8-dimethylnon-3-en-1-yl)-2,5,5-trimethyl-1,3-dioxane (Z-DHGA-neo)

$^1$H NMR (300 MHz, CDCl$_3$): δ 0.87 (d, J=6.6 Hz, 6H), 0.93 (s, 3H), 0.97 (s, 3H), 1.10-1.20 (m, 2H), 1.34-1.41 (m, 3H) superimposed by 1.36 (s, 3H), 1.53 (tqq, J=6.6, 6.6, 6.6 Hz, 1H), 1.64-1.75 (m, 2H) superimposed by 1.67 (q, J=1.5 Hz, 3H), 1.95-2.15 (m, 4H), AB signal ($\delta_A$=3.46, $\delta_B$=3.51, $J_{AB}$=11.1 Hz, 4H), 5.12 (br t, J=7.2 Hz, 1H) ppm.

$^{13}$C NMR (75 MHz, CDCl$_3$): δ 21.1 (1C), 22.0 (1C), 22.61 (3C), 22.65 (1C), 23.4 (1C), 25.7 (1C), 27.9 (1C), 29.9 (1C), 31.9 (1C), 37.2 (1C), 38.8 (1C), 70.3 (2C), 98.8 (1C), 124.6 (1C), 135.8 (1C) ppm.

MS (EI, m/z): 282 (M$^+$, 6), 267 [(M-CH$_3$)$^+$, 11], 129 (100), 95 (14), 69 (35), 43 (32).

IR (cm$^{-1}$): 2953 (s), 2867 (m), 1722 (w), 1468 (m), 1394 (m), 1368 (m), 1349 (w), 1306 (w), 1270 (m), 1250 (m), 1211 (m), 1189 (w), 1116 (s), 1086 (s), 1043 (m), 1022 (m), 951 (m), 925 (w), 907 (m), 856 (m), 792 (w), 739 (w), 677 (w), 667 (w).

d) Preparation of bis(trifluoroethyl) Ketals

A 250 mL three-necked flask with stir bar was dried under high vacuum (heat gun at 250° C.), then allowed to cool, flushed with argon and charged with 1,1,1 trifluoroethanol (TFE) (40 mL) under argon. The flask was cooled with an ice-bath while trimethylaluminum (2 M in heptane, 20.0 mL, 40.0 mmol, 1.95 eq.) was added dropwise within 60 min, keeping the temperature below 22° C. The two-phase (TFE/heptane) mixture became clear again after a few minutes and was allowed to stir for an additional 20 min at room temperature. 20.7 mmol of (E)-10,10-dimethoxy-2,6-dimethylundeca-2,6-diene (E-GA-DM) or (E)-2,2-dimethoxy-6,10-dimethylundec-5-ene (E-DHGA-DM), prepared as shown above, was added dropwise within 5 min at room temperature. After 1.5 h, GC analysis indicated full conversion of starting material. The reaction was quenched with a half-saturated solution of potassium sodium tartrate in water (100 mL), stirred for 2 h at room temperature and finally diluted with n-hexane (200 mL). The organic phase was separated, extracted with n-hexane (2×100 mL), dried over MgSO$_4$ and concentrated. The crude product was purified by column chromatography (neutral aluminium oxide, eluent: n-hexane). The characterization of the ketal is given in detail hereafter.

TABLE 2 d(iv)

| Preparation of bis(trifluoroethyl) ketals. | | |
|---|---|---|
| | E-GA-tfe | E-DHGA-tfe |
| Dimethylketal (reactant) | E-GA-DM | E-DHGA-DM |
| Ketal | (E)-2,6-dimethyl-10,10-bis(2,2,2-trifluoroethoxy)undeca-2,6-diene | (E)-6,10-dimethyl-2,2-bis(2,2,2-trifluoroethoxy)undec-5-ene |
| Yield [%] | 85 | 74 |
| E/Z | 99.4/0.6 | 95.0/5.0 |

Characterization Data (E)-2,6-dimethyl-10,10-bis(2,2,2-trifluoroethoxy)undeca-2,6-diene (E-GA-tfe)

$^1$H NMR (300 MHz, CDCl$_3$): δ 1.41 (s, 3H), 1.62 (br s, 6H), 1.67-1.76 (m, 2H), superimposed by 1.69 (q, J=0.9 Hz, 3H), 1.93-2.15 (m, 6H), 3.73-3.97 (m, 4H), 5.02-5.18 (m, 2H) ppm.

$^{13}$C NMR (150 MHz, CDCl$_3$): δ 15.9 (1C), 17.6 (1C), 21.3 (1C), 22.6 (1C), 25.7 (1C), 26.6 (1C), 36.9 (1C), 39.6 (1C), 59.3 (q, $J_{C,F}$=35.0 Hz, 2C), 103.4 (1C), 124.0 (q, $J_{C,F}$=275.0 Hz, 2C), 122.7 (1C), 124.1 (1C), 131.5 (1C), 136.2 (1C) ppm.

MS (EI, m/z): 361 [(M-CH$_3$)$^+$, 1], 276 [(M-TFE)$^+$, 15], 225 [(CF$_3$CH$_2$O)$_2$C—CH$_3$)$^+$, 86], 207 (20), 153 (18), 136 (58), 107 (80), 69 (100), 41 (40).

IR (cm$^{-1}$): 2927 (w), 2859 (w), 1459 (w), 1419 (w), 1385 (w), 1281 (s), 1223 (w), 1156 (s), 1133 (s), 1081 (s), 971 (s), 889 (m), 860 (w), 845 (w), 678 (w), 663 (w).

(E)-6,10-dimethyl-2,2-bis(2,2,2-trifluoroethoxy)undec-5-ene (E-DHGA-tfe)

$^1$H NMR (600 MHz, CDCl$_3$): δ 0.88 (d, J=6.8 Hz, 6H), 1.11-1.17 (m, 2H), 1.35-1.40 (m, 2H), 1.41 (s, 3H), 1.54 (qqt, J=6.7, 6.7, 6.7 Hz, 1H), 1.61 (br s, 3H), 1.69-1.73 (m, 2H), 1.95 (t, J=7.7 Hz, 2H), 2.03-2.09 (m, 2H), 3.78-3.91 (m, 4H), 5.09 (tq, J=7.1, 1.3 Hz, 1H) ppm.

$^{13}$C NMR (151 MHz, CDCl$_3$): δ 14.1 (1C), 15.8 (1C), 21.3 (1C), 22.56 (1C), 22.61 (1C), 25.6 (1C), 27.9 (1C), 37.0 (1C), 38.6 (1C), 39.8 (1C), 59.2 (q, $J_{C,F}$=35.0 Hz, 2C), 103.4 (1C), 124.0 (q, $J_{C,F}$=277.0 Hz, 2C), 122.4 (1C), 136.7 (1C) ppm.

MS (EI, m/z): 363 [(M-CH$_3$)$^+$, 1], 278 [(M-TFE)$^+$, 22], 225 [(CF$_3$CH$_2$O)$_2$C—CH$_3$)$^+$, 60], 193 (100), 153 (13), 127 (11), 83 (CF$_3$CH$_2^+$, 25), 69 (13), 43 (17).

IR (cm$^{-1}$): 2956 (w), 2933 (w), 2872 (w), 1462 (w), 1419 (w), 1385 (w), 1368 (w), 1281 (s), 1223 (w), 1156 (s), 1134 (s), 1081 (s), 971 (s), 889 (m), 860 (w), 845 (w), 679 (w), 663 (m).

Experiment E2b

Asymmetric Hydrogenations of Ketals of 6,10-dimethylundec-5-en-2-one or 6,10-dimethylundeca-5,9-dien-2-one An autoclave was charged with 0.5 mmol of ketals of 6,10-dimethylundeca-5,9-dien-2-one or 6,10-dimethylundec-5-en-2-one as indicated in tables 2e to 2h, and with 4 g of the solvent as indicated in tables 2e to 2h and a solution of the chiral iridium complex of formula (III-F) having the chirality given in tables 2e to 2h at the centre indicated by * in said formula in the amount indicated in tables 2e to 2h. The autoclave was closed and a pressure of 30 bar of molecular hydrogen was applied. The reaction mixture was stirred for 16 hours at room temperature. Afterwards the pressure was released and the solvent was removed.

The characterization of the hydrogenated ketals is given hereafter.

TABLE 2e

Asymmetric hydrogenation of different ketals of E-6,10-dimethyl-undeca-5,9-dien-2-one (E-GA).

|  | 16 | 17 | 18 | 19 |
|---|---|---|---|---|
| Ketal/ketone | E-GA | E-GA-DM | E-GA-neo | E-GA-neo |
| Formula of Ir complex | III-F | III-F | III-F | III-F |
| Configuration of chiral Ir complex at * | (S) | (S) | (S) | (S) |
| Amount of chiral Ir complex [mol-%] | 0.5 | 0.5 | 0.5 | 0.5 |
| Solvent[1] | DCM | TFE | DCM | TFE |
| Hydrogenated ketal/ketone | R-THGA | R-THGA-DM | R-THGA-neo | R-THGA-neo |
| Conversion [%] | 100 | >99 | >99 | >99 |
| Isomer-Distribution[2,3] | | | | |
| (R) [%] | 96.5 | 95.3 | 97.5 | 98.4 |
| (S) [%] | 3.5 | 4.7 | 2.5 | 1.6 |

Conditions: 0.5 mmol ketal, 4 g solvent, pressure p(H$_2$) = 30 bar, 16 h stirring at room temperature.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal TABLE 2f Asymmetric hydrogenation of different ketals of Z-6,10-dimethyl-undeca-5,9-dien-2-one (Z-GA).

|  | 20 | 21 | 22 | 23 |
|---|---|---|---|---|
| Ketal | Z-GA-DM | Z-GA-DM | Z-GA-neo | Z-GA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.25 | 0.25 | 0.25 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 98.2 | 98.5 | 97.9 | 98.6 |
| (S) [%] | 1.8 | 1.5 | 2.1 | 1.4 |

Conditions: 0.5 mmol ketal, 4 g solvent, pressure p(H$_2$) = 30 bar, 16 h stirring at room temperature.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal TABLE 2g Asymmetric hydrogenation of different ketals of E-DHGA.

|  | 24 | 25 | 26 | 27 |
|---|---|---|---|---|
| Ketal | E-DHGA-DM | E-DHGA-DM | E-DHGA-neo | E-DHGA-tfe |
| Formula of Ir complex | III-F | III-F | III-F | III-F |
| Configuration of chiral Ir complex at * | (S) | (S) | (S) | (S) |
| Amount of chiral Ir complex [mol-%] | 0.25 | 0.5 | 0.25 | 0.5 |
| Solvent[1] | DCM | TFE | DCM | TFE |
| Hydrogenated ketal | R-THGA-DM | R-THGA-DM | R-THGA-neo | R-THGA-tfe |
| Conversion [%] | >99 | >99 | >99 | >99 |
| Isomer-Distribution[2,3] | | | | |
| (R) [%] | 93.8 | 94.3 | 94.7 | 94.8 |
| (S) [%] | 6.2 | 5.7 | 5.3 | 5.2 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal TABLE 2h Asymmetric hydrogenation of different ketals of Z-DHGA.

|  | 28 | 29 | 30 | 31 |
|---|---|---|---|---|
| Ketal | Z-DHGA-DM | Z-DHGA-DM | Z-DHGA-neo | Z-DHGA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.25 | 0.5 | 0.5 | 0.5 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 99.2 | 99.4 | 97.8 | 98.0 |
| (S) [%] | 0.8 | 0.6 | 2.2 | 2.0 |

[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal Characterization Data (R)-2,2-dimethoxy-6,10-dimethylundecane
(R-THGA-DM)

$^1$H NMR (300 MHz, CDCl$_3$): δ 0.848 (d, J=6.6 Hz, 3H) superimposed by 0.852 (d, J=6.6 Hz, 6H), 1.01-1.41 (m, 11H) superimposed by 1.25 (s, 3H), 1.44-1.61 (m, 3H), 3.16 (s, 6H) ppm.

$^{13}$C NMR (75 MHz, CDCl$_3$): δ 14.1 (1C), 19.6 (1C), 20.9 (1C), 21.7 (1C), 22.6 (1C), 22.7 (1C), 24.8 (1C), 27.9 (1C), 32.7 (1C), 36.8 (1C), 37.2 (1C), 37.4 (1C), 39.3 (1C), 47.9 (1C), 101.7 (1C) ppm.

MS (EI, m/z): No GC-MS was obtained due to decomposition on the column.

IR (cm$^{-1}$): 2951 (s), 2927 (m), 2870 (m), 2828 (m), 1723 (w), 1462 (m), 1377 (m), 1309 (w), 1256 (m), 1215 (m), 1194 (m), 1172 (m), 1111 (m), 1089 (m), 1053 (s), 972 (w), 934 (w), 920 (w), 855 (m), 815 (m), 736 (w), 618 (w).

(R)-2-(4,8-dimethylnonyl)-2,5,5-trimethyl-1,3-dioxane (R-THGA-neo)

$^1$H NMR (300 MHz, CDCl$_3$): δ 0.87 (d, J=6.6 Hz, 9H) 0.91 (s, 3H), 1.01 (s, 3H), 1.04-1.61 (m, 12H) superimposed by 1.36 (s, 3H), 1.61-1.74 (m, 2H), AB signal (δA=3.44, δB=3.54, JAB=11.7 Hz, 4H) ppm.

$^{13}$C NMR (75 MHz, CDCl$_3$): δ 19.7 (1C), 20.4 (1C), 21.0 (1C), 22.56 (1C), 22.61 (1C), 22.71 (1C), 22.77 (1C), 24.8 (1C), 28.0 (1C), 30.0 (1C), 32.8 (1C), 37.3 (1C), 37.4 (1C), 38.2 (1C), 39.3 (1C), 70.3 (2C), 99.1 (1C) ppm.

MS (EI, m/z): 269 [(M-CH$_3$)$^+$, 65), 199 (8), 129 (100), 109 (8), 69 (32), 55 (10), 43 (25).

IR (cm$^{-1}$): 2953 (s), 2925 (s), 2868 (m), 1722 (w), 1464 (m), 1394 (m), 1371 (m), 1316 (w), 1258 (m), 1212 (m), 1161 (m), 1141 (m), 1111 (s), 1095 (s), 1043 (m), 1020 (m), 951 (m), 925 (m), 907 (m) 870 (m), 855 (m), 801 (m), 792 (m), 737 (m), 677 (w), 667 (w).

(R)-6,10-dimethyl-2,2-bis(2,2,2-trifluoroethoxy)
undecane (R-THGA-tfe)

$^1$H NMR (300 MHz, CDCl$_3$): δ 0.88 (d, J=6.6 Hz, 6H), 0.87 (d, J=6.4 Hz, 3H), 1.03-1.23 (m, 5H), 1.39 (s, 3H), 1.38-1.40 (m, 6H), 1.46-1.71 (m, 3H), 3.73-3.94 (m, 4H).

$^{13}$C NMR (75 MHz, CDCl$_3$): δ 19.5 (1C), 21.39 (1C), 21.47 (1C), 22.58 (1C), 22.68 (1C), 24.7 (1C), 28.0 (1C), 32.6 (1C), 37.0 (1C), 37.19 (1C), 37.23 (1C), 39.3 (1C), 59.2 (q, $^2J_{C,F}$=32.5 Hz, 2C), 103.6 (1C), 124.1 (q, $^1J_{C,F}$=279.0 Hz, 2C).

MS (EI, m/z): 365 [(M-CH$_3$)$^+$, 1], 281 (2), 225 [(CF$_3$CH$_2$O)$_2$C—CH$_3$)$^+$, 100], 153 (8), 140 (6), 83 (CF$_3$CH$_2$$^+$, 6), 43 (7).

IR (cm$^{-1}$): 2955 (w), 2929 (w), 2872 (w), 1463 (w), 1419 (w), 1385 (w), 1281 (s), 1216 (w), 1156 (s), 1122 (m), 1082 (s), 972 (m), 892 (m), 861 (w), 737 (w), 679 (w), 663 (m).

Experiment E2c

Hydrolysis of Hydrogenated Ketals of
6,10-dimethylundec-5-en-2-one or
6,10-dimethylundeca-5,9-dien-2-one After the asymmetric hydrogenation of ketals of (6R, 10R)-6,10,14-trimethylpentadecan-2-one, the hydrogenated ketals obtained were hydrolysed to the ketone and yielded (R)-6,10-dimethylundecan-2-one or (S)-6,10-dimethylundecan-2-one, respectively.

Method 1—Neopentyl Ketals, Dimethyl Ketals from Asymmetric Hydrogenation Reactions in Dichloromethane A sample of the reaction mixture from the asymmetric hydrogenation reaction (1-2 ml) was stirred with an equal volume of 1M aqueous solution of hydrochloric acid at room temperature for 1 hour. Dichloromethane (2 ml) was added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.

Method 2—Ethylene Glycol Ketals, Bis(Trifluoroethanol) Ketals and Dimethyl Ketals from Asymmetric Hydrogenation Reactions in Trifluoroethanol A sample of the reaction mixture from the asymmetric hydrogenation reaction (1-2 ml) was stirred with 0.5 ml of a solution of 9:1:0.2 (by volume) methanol:water:trifluoroacetic acid at 40° C. for 1 hour. Dichloromethane (2 ml) and water (2 ml) were added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.

Experiment E2d

Asymmetric Hydrogenations of Ketones and Ketals
of 6,10-dimethylundec-5-en-2-one or
6,10-dimethylundeca-5,9-dien-2-one An autoclave vessel was charged under nitrogen with chiral iridium complex of formula (III-F) of the R configuration at the chiral centre marked by *, the ketone or ketal (conc.) as indicated in table 2h or 2i, solvent as indicated in table 2h or 2i). The reaction vessel was closed and pressurized with molecular hydrogen to the pressure (pH$_2$) indicated in table 2h or 2i. The reaction mixture was stirred at room temperature for the time (t) as indicated in table 2h or 2i under hydrogen. Then the pressure was released and the assay yield and the stereoisomer distribution of the fully hydrogenated product was determined. In case of ketals the assay yield and the stereoisomer distribution have been determined after the hydrolysis of the ketal by acid as indicated in experiment E2c. The catalyst loading (S/C) is defined as mmol ketone or ketal ("substrate")/mmol chiral iridium complex.

TABLE 2h

| Hydrogenation of E-DHGA and of E-DHGA-en. The effect of ketalization. | | |
|---|---|---|
| | 32 | 33 |
| Ketone to be hydrogenated | E-DHGA | |
| Ketal to be hydrogenated | | E-DHGA-en |
| conc.$^1$ [mol/L] | 1.0 | 0.9 |
| pH$_2$ [bar] | 50 | 50 |
| t [h] | 20 | 20 |
| S/C | 10'000 | 10'000 |
| Solvent | TFE | TFE |
| Assay yield [area-%] | 1 | 97 |

TABLE 2h-continued

Hydrogenation of E-DHGA and of E-DHGA-en. The effect of ketalization.

|  | 32 | 33 |
|---|---|---|
| Isomer-Distribution[3,4] | | |
| (R) [%] | n.d.[2] | 2.2 |
| (S) [%] | n.d.[2] | 97.8 |

[1]conc. = mol ketone or ketal/L solvent
[2]n.d. = not determined (due to low assay yield)
[3](R) stands for the R-isomer, (S) stands for the S-isomer of the ethylene glycol ketal of 6,10-dimethylundecan-2-one
[4]is determined as ketone after hydrolysis of the ketal

TABLE 2i

Hydrogenation of Z-DHGA and of Z-DHGA-en and of Z-DHGA-neo. The effect of ketalization.

|  | 34 | 35 | 36 | 37 |
|---|---|---|---|---|
| Ketone to be hydrogenated | Z-DHGA | | | |
| Ketal to be hydrogenated | | Z-DHGA-en | Z-DHGA-en | Z-DHGA-neo |
| conc.[1] [mol/L] | 1.0 | 0.2 | 0.2 | 0.2 |
| pH$_2$ [bar] | 50 | 25 | 25 | 25 |
| t [h] | 20 | 15 | 15 | 24 |
| S/C | 5'000 | 5'000 | 10'000 | 10'000 |
| Solvent | DCM | DCM | DCM | DCM |
| Assay yield [area-%] | 1 | 84 | 39 | 22 |
| Isomer-Distribution[3,4] | | | | |
| (R) [%] | n.d.[2] | 98.6 | 98.4 | 95 |
| (S) [%] | n.d.[2] | 1.4 | 1.6 | 5 |

[1]conc. = mol ketone or ketal/L solvent (DCM = dichloromethane)
[2]n.d. = not determined (due to low assay yield)
[3](R) stands for the R-isomer, (S) stands for the S-isomer of the ethylene glycol ketal of 6,10-dimethylundecan-2-one
[4]is determined as ketone after hydrolysis of the ketal

Experiment E2e

Asymmetric Hydrogenations of 6,10-dimethylundec-5-en-2-one or 6,10-dimethylundeca-5,9-dien-2-one or the Ketals Thereof in the Presence of Additives The asymmetric hydrogenation was performed as in experiment E2d with the difference that additives are used for the hydrogenation. The additive and the amounts used are indicated in table 2j, 2k for the hydrogenation of ketals and in table 2l and 2m for the hydrogenation of ketones.

Preparation of Additives

MAO/TFE: A 1.6 M MAO (MAO: methylaluminoxane solution in toluene (0.64 mL) was quenched with 2,2,2-trifluoroethanol (TFE) (3.1 mmol), leading to small excess of free TFE.

EAO/TFE: A 10 wt % EAO (EAO: ethylaluminoxane solution in toluene (1 mmol) was quenched with TFE (3.2 mmol), leading to small excess of free TFE.

TMA/TFE: A 2 M TMA (TMA: trimethylaluminum (Al(CH$_3$)$_3$)) solution in heptane (1 mmol) was quenched with TFE (3.1 mmol), leading to small excess of free TFE.

TEA/TFE: A 2 M TEA (TEA: triethylaluminum (Al(CH$_2$CH$_3$)$_3$)) solution in heptane (1 mmol) was quenched with TFE (3.1 mmol), leading to small excess of free TFE.

TMA/BHT/TFE: A 2 M TMA solution in heptane (1 mmol) was quenched with 2,6-di-tert-butyl-4-methylphenol (BHT) (2 mmol) and subsequently with TFE (3.1 mmol), leading to small excess of free TFE.

Ti(OCH$_2$CF$_3$)$_4$: Tetraisopropyl orthotitanate (8.1 mmol) was dissolved in 2,2,2-trifluoroethanol at 50° C. Removal of the solvent gave Ti(OCH$_2$CF$_3$)$_4$ as a white residue which was isolated and identified to be Ti(OCH$_2$CF$_3$)$_4$.

These additives were freshly prepared and used either as a heterogeneous mixture at room temperature or homogeneous by heating to a temperature between 50° and 70° C.

The additives tetraisopropyl orthotitanate (Ti(OiPr)$_4$), triisopropylborate (B(OiPr)$_3$), sodium tetrakis[3,5-bis(trifluoromethyl)phenyl]borate (NaBAr$_F$) and triethyl borane (TEB) (1 M solution in hexane) are commercially available and were used as received.

TABLE 2j

Hydrogenation of E-DHGA-en at pressure of molecular hydrogen (pH$_2$) of 50 bar and stirring at room temperature during 20 hours. The effect of the additives.

|  | 38 | 39 | 40 | 41 | 42 |
|---|---|---|---|---|---|
| Ketal to be hydrogenated | E-DHGA-en | E-DHGA-en | E-DHGA-en | E-DHGA-en | E-DHGA-en |
| conc.[1] [mol/L] | 0.2 | 0.7 | 0.2 | 2.3 | Neat |
| S/C | 10'000 | 30'000 | 20'000 | 20'000 | 20'000 |
| Solvent | DCM | DCM | DCM | hexane | — |
| Additive | — | MAO/TFE | TMA/TFE | TEB | B(OiPr)$_3$ |
| Additive concentration [mol-%][2] | — | 10 | 2 | 5 | 10 |
| Assay yield [area-%] | 68 | 99 | 99 | 83 | 97 |
| Isomer-Distribution[3,4] | | | | | |
| (R) [%] | 5 | 3 | 2 | 3.4 | 2.6 |
| (S) [%] | 95 | 97 | 98 | 96.6 | 97.4 |

[1]conc. = mol ketal/L solvent
[2]relative to the molar amount of E-DHGA-en
[3](R) stands for the R-isomer, (S) stands for the S-isomer of the ethylene glycol ketal of 6,10-dimethylundecan-2-one
[4]is determined as ketone after hydrolysis of the ketal.

TABLE 2k

Hydrogenation of different ketals of Z-DHGA at pressure of molecular hydrogen (pH$_2$) of 50 bar and stirring at room temperature during 20 hours. The effect of the additives.

|  | 43 | 44 | 45 | 46 | 47 | 48 |
|---|---|---|---|---|---|---|
| Ketal to be hydrogenated | Z-DHGA-en | Z-DHGA-en | Z-DHGA-en | Z-DHGA-en | Z-DHGA-neo | Z-DHGA-neo |
| conc.[1] [mol/L] | 0.2 | 0.2 | 0.2 | 0.2 | 0.2 | 0.2 |
| S/C | 5'000 | 10'000 | 10'000 | 52'000 | 20'000 | 20'000 |
| Solvent[3] | DCM | DCM | TFE | TFE | TFE | TFE |
| Additive | — | — | NaBAr$_F$ | TMA[4] | — | TMA[4] |
| Additive concentration [mol-%][2] | — | — | 0.014 | 100 | — | 10 |

TABLE 2k-continued

Hydrogenation of different ketals of Z-DHGA at pressure of molecular hydrogen (pH$_2$) of 50 bar and stirring at room temperature during 20 hours. The effect of the additives.

| | 43 | 44 | 45 | 46 | 47 | 48 |
|---|---|---|---|---|---|---|
| Assay yield [area-%] | 84 | 39 | 46 | 93 | 4 | 63 |
| Isomer-Distribution[5,6] | | | | | | |
| (R) [%] | 98.6 | 98.4 | 97.5 | 98.1 | n.d.[5] | 98.8 |
| (S) [%] | 1.4 | 1.6 | 2.5 | 1.9 | n.d.[5] | 1.2 |

[1]conc. = mol ketal/L solvent
[2]relative to the molar amount of ketal of Z-DHGA
[3]TFE = 2,2,2-trifluoroethanol; DCM = dichloromethane
[4]TMA is quenched by adding into the solvent TFE
[5](R) stands for the R-isomer, (S) stands for the S-isomer of the corresponding ketal of 6,10-dimethylundecan-2-one
[6]is determined as ketone after hydrolysis of the ketal.

TABLE 2l

Hydrogenation of E-DHGA at pressure of molecular hydrogen (pH$_2$) of 50 bar and stirring at room temperature during 20 hours. The effect of the additives.

| | 49 | 50 | 51 | 52 | 53 |
|---|---|---|---|---|---|
| Ketone to be hydrogenated | E-DHGA | E-DHGA | E-DHGA | E-DHGA | E-DHGA |
| conc.[1] [mol/L] | 1.0 | 0.8 | 0.2 | 0.2 | 0.9 |
| S/C | 10'000 | 10'000 | 10'000 | 10'000 | 10'000 |
| Solvent | TFE | TFE | TFE | TFE | TFE |
| Additive | — | TMA/TFE | TMA/TFE | MAO/TFE | Ti(OiPr)$_4$ |
| Additive concentration [mol-%][2] | — | 5 | 5 | 10 | 10 |
| Assay yield [area-%] | 1 | 73 | 78 | 53 | 90 |
| Isomer-Distribution[5, 6] | | | | | |
| (R) [%] | n.d.[3] | 2.8 | 2.3 | 4.2 | 2.2 |
| (S) [%] | n.d.[3] | 97.2 | 97.7 | 95.8 | 97.8 |

[1]conc. = mol ketone/L solvent
[2]relative to the molar amount of E-DHGA.
[3]n.d. = not determined (due to low assay yield).

TABLE 2m

Hydrogenation of Z-DHGA at pressure of molecular hydrogen (pH$_2$) of 50 bar and stirring at room temperature during 20 hours. The effect of the additives.

| | 54 | 55 |
|---|---|---|
| Ketone to be hydrogenated | Z-DHGA | Z-DHGA |
| conc.[1] [mol/L] | 1.0 | 0.8 |
| S/C | 5'000 | 5'000 |
| Solvent | DCM | DCM |
| Additive | — | TMA/TFE |
| Additive concentration [mol-%][2] | — | 5 |
| Assay yield [area-%] | 1 | 40 |
| (R)-6,10-dimethylundecan-2-one [%] | n.d.[3] | 98.3 |
| (S)-6,10-dimethylundecan-2-one [%] | n.d.[3] | 1.7 |

[1]conc. = mol ketone/L solvent
[2]relative to the molar amount of Z-DHGA
[3] n.d. = not determined (due to low assay yield)..

Chemical Transformation Steps (Step d)

Experiment E38

Vinylation of (R)-6,10-dimethylundecan-2-one (Step d1')

A dried 100 mL four-necked flask equipped with overhead stirrer, thermometer, condenser and argon inlet was evacuated and purged with argon. Vinylmagnesium chloride (23.63 mL of a 1.6 M solution in THF, 37.8 mmol, 1.56 eq.) was added at room temperature. A solution (R)-6,10-dimethylundecan-2-one (5.01 g, 24.24 mmol, 96.0%, 1.0 eq.) in dry THF (20 mL) was added slowly within 20 min. The exothermic reaction was maintained between 25 and 30° C. internal temperature by cooling with an ice bath. After complete addition the reaction was allowed to stir at room temperature for 1 h. Saturated NH$_4$Cl solution (10 mL) was added carefully to quench excess Grignard reagent. Pentane (150 mL), water (150 mL) and brine (150 mL) was added. The organic phase was extracted with brine (2×150 mL) and the aqueous phase was back-extracted with pentane (2×150 mL). The combined organic phases were dried (MgSO$_4$) and concentrated in vacuo, resulting in a colorless oil (5.42 g). The crude product was purified by vacuum distillation in a Kugelrohr apparatus. The main fraction distilled at 143° C./3.8$^{-2}$ mbar, furnishing (7R)-3,7,11-trimethyldodec-1-en-3-ol as colorless oil with a purity of 94.0% (5.15 g, 21.38 mmol, 88% yield).

Experiment E3b

Ethynylation of (R)-6,10-dimethylundecan-2-one (Step d1)

(R)-6,10-dimethylundecan-2-one (340 g, 1.70 mol, 1.0 eq., 99.0%) was added to an autoclave equipped with thermostat, dosing pump, acetylene inlet and ammonia inlet. The reactor was sealed, evacuated and flushed with nitrogen and cooled to 15° C. Ammonia (632 g, 37.2 mol, 22.0 eq., 99.8%) was condensed into the reactor and cooled to 15° C., resulting in a pressure of 8-9 bar. Acetylene was introduced until 12 bar pressure was reached, followed by a dosed addition of KOH (45 wt.-% in water, 6.6 g, 52.9 mmol, 3.1 mol %) at 15° C. The reaction progress was monitored by GC. After 90 min the reaction mixture was neutralized with acetic acid, and the reactor was subsequently vented at 25° C. The reaction mixture was washed and concentrated in vacuo and purified by distillation in vacuo furnishing 325 g of (7R)-3,7,11-trimethyldodec-1-yn-3-ol with a purity of 95% (81% yield).

Experiment E3c

Hydrogenation of (7R)-3,7,11-trimethyldodec-1-yn-3-ol (Step d2)

(7R)-3,7,11-trimethyldodec-1-yn-3-ol (910 g, 4.06 mol, 1.0 eq., 95%). Lindlar catalyst catalyst (850 mg) were placed into an autoclave. The reactor was sealed, evacuated, flushed with nitrogen and subsequently heated to 45° C. The reactor was evacuated once more and flushed with hydrogen, pressurized to 2 bar. The reaction was stirred for approx. 2-3 hours at 45° C. until the calculated amount of molecular hydrogen had been consumed. After filtration 884 g of (7R)-3,7,11-trimethyldodec-1-en-3-ol was obtained with a purity of 91.5% (88% yield).

Experiment E4

Reaction of (7R)-3,7,11-trimethyldodec-1-en-3-ol with 2-methoxyprop-1-ene (Step d3)

(7R)-3,7,11-trimethyldodec-1-en-3-ol (640 g, 2.59 mol, 1.0 eq., 91.5%), $H_3PO_4$ (20 wt % in water, 4.5 g, 8.2 mmol, 0.32 mol %) and isopropenyl methyl ether (600 g, 8.17 mol, 3.2 eq., 98.0%) were placed into a 2 L autoclave equipped with thermostat, overhead stirrer and 1.1 m distillation column (Sulzer packing). The reactor was sealed, evacuated and flushed with nitrogen and subsequently heated to 80° C. The pressure that built up was slowly vented. The inner temperature was then gradually raised to 160° C. within 1 h. The reaction was stirred for 3 h at 160° C. The reaction mixture was cooled to 30° C., concentrated in vacuo and washed with water and $NaHCO_3$ solution. Then low boilers were removed by distillation (jacket temperature 150° C., 1 mbar), furnishing 690 g of a mixture of (R,E)-6,10,14-trimethylpentadec-5-en-2-one and (R,Z)-6,10,14-trimethylpentadec-5-en-2-one as residue with a purity of 85% (85% yield). The mixture was analyzed by GC to be a mixture of 49% E-isomer and 36% Z-isomer.

Experiment E5

Separation of E/Z Isomer Mixtures of (R,Z)-6,10,14-trimethylpentadec-5-en-2-one (Step e)

The mixture of (R,E)-6,10,14-trimethylpentadec-5-en-2-one and (R,Z)-6,10,14-trimethylpentadec-5-en-2-one 1.94 kg, 36% (R,Z)-6,10,14-trimethylpentadec-5-en-2-one and 49% (R,E)-6,10,14-trimethylpentadec-5-en-2-one was fractionated using the separation equipment consisting of a still (volume: 9 liter) with a falling film evaporator, a rectifying column (70 mm inner diameter, height 5 m). The column was equipped with a very efficient structured packing (Sulzer). The rectification process was operated at a top pressure of approx. 2 mbar and at a column top temperature varied in the range from 95 to 122° C. and the bottom temperature in the still was 165° C. The reflux ratio was adjusted to 20. Fractionation of the distillate stream furnished fractions containing (R,Z)-6,10,14-trimethylpentadec-5-en-2-one (content of Z-isomer=97%). At the end (R,E)-6,10,14-trimethylpentadec-5-en-2-one was found left in the still (content of E-isomer=94%). Both isomers were further purified by fractionation and furnished fractions of both E-isomer and Z-isomer each with a purity of 99.5%)

Experiment E6

Asymmetric Hydrogenations of (R,E)-6,10,14-trimethylpentadec-5-en-2-one and (R,Z)-6,10,14-trimethylpentadec-5-en-2-one (Step f)

Both isomers (R,E)-6,10,14-tri methyl pentadec-5-en-2-one) (R,E-THFA) (E/Z=99.5/0.5, R/S=92/8) and (R,Z)-6,10,14-trimethylpentadec-5-en-2-one (R,Z-THFA) (Z/E=99.5/0.5, R/S=92/8) were hydrogenated asymmetrically, separate from each other in the following manner:

A 125 mL autoclave was charged with 7.0 g (26 mmol) of the specific isomer, 50 mL of 2,2,2-trifluoroethanol and a solution of the chiral iridium complex of formula (III-F) having the chirality given in table 3 at the centre indicated by * in said formula (42 mg, 0.026 mmol, 0.1 mol %) in anhydrous dichloromethane (4 g). The autoclave was closed and a pressure of 50 bar of molecular hydrogen was applied. The reaction mixture was heated to 30° C. whilst stirring for 16 hours. Afterwards the pressure was released and the solvent removed. The product formed is (6R,10R)-6,10,14-trimethylpentadecan-2-one. The conversion as well as the amount of isomers formed is given in table 3.

The products of the two separate asymmetric hydrogenations have been combined.

In a further experiment in an autoclave 0.25 mmol of (R,E)-6,10,14-trimethylpentadec-5-en-2-one) (R,E-THFA) and 1 mol-%, of the Ir complex of the formula (III-D) and 1.25 ml of absolute (dry) dichloromethane were put. The autoclave was closed and a pressure of 50 bar of molecular hydrogen was applied. Under stirring the reaction solution was kept at room temperature for 14 hours. Afterwards the pressure was released and the solvent removed. For determining the conversion the crude product was analysed by achiral gas chromatography without any further purification. The amount for the isomers has been determined using the above method and given in table 3.

In a further experiment in an autoclave 0.5 mmol of (R,E)-6,10,14-trimethylpentadec-5-en-2-one) (R,E-THFA) and 1 mol-%, of the Ir complex of the formula as indicated in table 3' and 4 g solvent as indicated in table 3' were put. The autoclave was closed and a pressure of 30 bar of molecular hydrogen was applied. Under stirring the reaction solution was kept at room temperature for 16 hours. Afterwards the pressure was released and the solvent removed. For determining the conversion the crude product was analysed by achiral gas chromatography without any further purification. The amount for the isomers has been determined using the above method and given in table 3'.

TABLE 3

Asymmetric hydrogenation of R,E-THFA and R,Z-THFA.

|  | 56 R,Z-THFA | 57 R,E-THFA | 58 R,E-THFA |
|---|---|---|---|
| Formula of Ir-complex | III-F | III-F | III-D |
| Configuration of chiral Ir-complex | R | S | S |
| Amount of chiral Ir complex [mol-%] | 0.1 | 0.1 | 1 |
| Conversion [%] | >99 | >99 | 100 |
| (6R,10R)-6,10,14-trimethylpentadecan-2-one [%] | 87.0 | 88.4 | 97.0 |
| (6S,10R)-6,10,14-trimethylpentadecan-2-one [%] | 5.3 | 3.7 | 1.8 |
| (6R,10S)-6,10,14-trimethylpentadecan-2-one [%] | 7.7 | 7.9 | 1.2* |
| (6S,10S)-6,10,14-trimethylpentadecan-2-one [%] | 0.0 | 0.0 |  |

*(6R,10S) and (6S,10S) isomers determined as sum.

TABLE 3'

Asymmetric hydrogenation of R,E-THFA and R,Z-THFA with different Ir complexes.

|  | 59 R,E-THFA | 60 R,E-THFA | 61 R,E-THFA | 62 R,E-THFA |
|---|---|---|---|---|
| Formula of Ir complex | III-C | III-D | III-D | III-A'2 |
| Configuration of chiral Ir complex at * | S | R | S | S |
| Amount of chiral Ir complex [mol-%] | 1 | 1 | 1 | 1 |
| Solvent[1] | DCM | TFE | DCM | DCM |
| Conversion [%] | >99 | >99 | >99 | >99 |

TABLE 3'-continued

Asymmetric hydrogenation of R,E-THFA and R,Z-THFA with different Ir complexes.

| | 59 R,E-THFA | 60 R,E-THFA | 61 R,E-THFA | 62 R,E-THFA |
|---|---|---|---|---|
| Isomer-Distribution | | | | |
| (6R,10R)-6,10,14-trimethylpentadecan-2-one [%] | 97.3 | 0.9 | 96.9 | 96.6 |
| (6S,10R)-6,10,14-trimethylpentadecan-2-one [%] | 1.3 | 97.0 | 1.8 | 2.0 |
| (6R,10S)-6,10,14-trimethylpentadecan-2-one [%] | 1.4 | 0 | 1.3 | 1.4 |
| (6S,10S)-6,10,14-trimethylpentadecan-2-one [%] | 0 | 2.1 | 0 | 0 |

[1]TFE = 2,2,2-trifluoroethanol; DCM = dichloromethane
[2]chiral Ir complex of formula (III-A'):

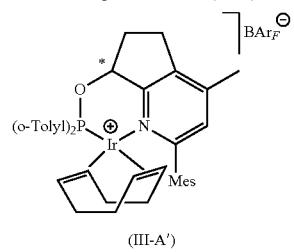

(III-A')

Experiment E6a

Preparation of Ketals of (R,E)-6,10,14-trimethylpentadec-5-en-2-one and (R,Z)-6,10,14-trimethylpentadec-5-en-2-one (Step $f_o$)

The dimethyl ketals, neopentyl glycol ketals or bis(trifluoroethyl) ketals, respectively, of (R,E)-6,10,14-trimethylpentadec-5-en-2-one and (R,Z)-6,10,14-trimethylpentadec-5-en-2-one have been obtained in analogy to experiment E2a described above for 6,10-dimethylundec-5-en-2-one or 6,10-dimethylundeca-5,9-dien-2-one.

TABLE 3a

Preparation of dimethyl and neopentyl glycol ketals of 6,10,14-trimethylpentadec-5-en-2-one.

| | R-E-THFA-DM | R-Z-THFA-DM | R-E-THFA-neo | R-Z-THFA-neo |
|---|---|---|---|---|
| Ketone | (R,E)-6,10,14-trimethylpentadec-5-en-2-one | (R,Z)-6,10,14-trimethylpentadec-5-en-2-one | (R,E)-6,10,14-trimethylpentadec-5-en-2-one | (R,Z)-6,10,14-trimethylpentadec-5-en-2-one |
| Ketal | (R,E)-2,2-dimethoxy-6,10,14-trimethylpentadec-5-ene | (R,Z)-2,2-dimethoxy-6,10,14-trimethylpentadec-5-ene | (R,E)-2,5,5-trimethyl-2-(4,8,12-trimethyltridec-3-en-1-yl)-1,3-dioxane | (R,Z)-2,5,5-trimethyl-2-(4,8,12-trimethyltridec-3-en-1-yl)-1,3-dioxane |
| Yield [%] | 92 | 87 | 83 | 86 |
| E/Z | 99.5/0.5 | 3.6/96.4 | 99.8/0.2 | 4/96 |

Characterization Data (R,E)-2,2-dimethoxy-6,10,14-trimethylpentadec-5-ene (R-E-THFA-DM)

$^1$H NMR (300 MHz, CDCl$_3$): δ 0.84 (d, J=6.6 Hz, 3H), superimposed by 0.86 (d, J=6.6 Hz, 6H), 0.99-1.44 (m, 11H), superimposed by 1.28 (s, 3H), 1.52 (tqq, J=6.6, 6.6, 6.6 Hz, 1H), 1.60 (s, 3H), 1.60-1.66 (m, 2H), 1.90-2.05 (m, 4H), 3.18 (s, 6H), 5.10 (tq, J=7.1, 1.1 Hz, 1H) ppm.
$^{13}$C NMR (75 MHz, CDCl$_3$): δ 16.3 (1C), 20.1 (1C), 21.3 (1C), 23.0 (1C), 23.1 (1C), 23.2 (1C), 25.2 (1C), 25.7 (1C), 28.4 (1C), 33.1 (1C), 36.9 (1C), 37.1 (1C), 37.7 (1C), 39.8 (1C), 40.3 (1C), 48.4 (2C), 101.9 (1C), 124.0 (1C), 136.0 (1C) ppm.
MS (EI, m/z): No GC-MS was obtained due to decomposition on the column.
IR (cm$^{-1}$): 2952 (m), 2927 (s), 2869 (m), 2828 (w), 1461 (m), 1377 (m), 1301 (w), 1262 (m), 1222 (m), 1197 (m), 1172 (m), 1120 (m), 1101 (m), 1076 (m), 1054 (s), 930 (w), 854 (m), 737 (w), 620 (w).

(R,Z)-2,2-dimethoxy-6,10,14-trimethylpentadec-5-ene (R-Z-THFA-DM)

$^1$H NMR (300 MHz, CDCl$_3$): δ 0.85 (d, J=6.4 Hz, 3H), superimposed by 0.87 (d, J=6.4 Hz, 6H), 1.01-1.27 (m, 7H), 1.28 (s, 3H), 1.29-1.44 (m, 4H), 1.53 (dqq, J=6.5, 6.5 Hz, 6.5 Hz, 1H), 1.58-1.66 (m, 2H), 1.68 (q, J=1.1 Hz, 3H), 1.91-2.08 (m, 4H), 3.18 (s, 6H), 5.11 (t, J=6.8 Hz, 1H) ppm.
$^{13}$C NMR (75 MHz, CDCl$_3$): δ) 19.7 (1C), 20.9 (1C), 22.60 (1C), 22.69 (1C), 22.71 (1C), 23.4 (1C), 24.8 (1C), 25.5 (1C), 28.0 (1C), 32.0 (1C), 32.7 (1C), 36.8 (1C), 37.0 (1C), 37.3 (1C), 39.3 (1C), 48.0 (2C), 101.5 (1C), 124.3 (1C), 135.9 (1C) ppm.
MS (EI, m/z): No GC-MS was obtained due to decomposition on the column.
IR (cm$^{-1}$): 2952 (m), 2927 (m), 2869 (m), 2828 (w), 1462 (m), 1376 (m), 1301 (w), 1261 (w), 1197 (w), 1172 (m), 1119 (m), 1098 (m), 1074 (m), 1054 (s), 1022 (w), 854 (m), 736 (w), 622 (w).

(R,E)-2,5,5-trimethyl-2-(4,8,12-trimethyltridec-3-en-1-yl)-1,3-dioxane (R-E-THFA-neo)

$^1$H NMR (300 MHz, CDCl$_3$): δ 0.84 (d, J=6.4 Hz, 3H), 0.86 (d, J=6.6 Hz, 6H), 0.92 (s, 3H), 0.99 (s, 3H), superimposed by 0.97-1.44 (m, 11H), superimposed by 1.37 (s, 3H), 1.52 (qqt, J=6.9, 6.9, 6.9 Hz, 1H), 1.60 (s, 3H), 1.67-1.76 (m, 2H), 1.93 (t, J=7.4 Hz, 2H), 2.03-2.18 (m, 2H), AB signal (δ$_A$=3.45, δ$_B$=3.52, J$_{AB}$=11.4 Hz, 4H), 5.12 (tq, J=7.2, 1.0 Hz, 1H) ppm.
$^{13}$C NMR (75 MHz, CDCl$_3$): δ 15.8 (1C), 19.7 (1C), 20.9 (1C), 22.0 (1C), 22.6 (2C), 22.7 (2C), 24.8 (1C), 25.3 (1C), 27.9 (1C), 29.9 (1C), 32.6 (1C), 36.6 (1C), 37.3 (1C), 37.4 (1C), 39.3 (1C), 39.9 (1C), 70.3 (2C), 98.8 (1C), 123.8 (1C), 135.5 (1C) ppm.
MS (EI, m/z): 352 (M$^+$, 4), 337 [(M-CH$_3$)$^+$, 8), 265 (6), 129 (100), 95 (10), 69 (25), 43 (25).
IR (cm$^{-1}$): 2953 (s), 2926 (s), 2867 (m), 1462 (m), 1394 (w), 1369 (m), 1270 (w), 1249 (m), 1211 (m), 1187 (w), 1119 (s), 1088 (s), 1043 (m), 1021 (w), 951 (w), 925 (w), 907 (w), 862 (m), 791 (w), 738 (w), 678 (w).

(R,Z)-2,5,5-trimethyl-2-(4,8,12-trimethyltridec-3-en-1-yl)-1,3-dioxane (R-Z-THFA-neo)

$^1$H NMR (300 MHz, CDCl$_3$): δ 0.84 (d, J=6.4 Hz, 3H), superimposed by 0.86 (d, J=6.6 Hz, 6H), 0.93 (s, 3H), 0.97

(s, 3H), 1.00-1.42 (m, 11H), superimposed by 1.36 (s, 3H), 1.52 (qqt, J=6.7, 6.7, 6.7 Hz, 1H), 1.63-1.76 (m, 2H), 1.67 (s, 3H), 1.94-2.15 (m, 4H), AB signal ($\delta_A$=3.45, $\delta_B$=3.51, $J_{AB}$=11.1 Hz, 4H), 5.12 (t, J=7.1 Hz, 1H) ppm.

$^{13}$C NMR (75 MHz, CDCl$_3$): δ 19.6 (1C), 21.1 (1C), 21.9 (1C), 22.60 (2C), 22.67 (2C), 22.69 (1C), 23.4 (1C), 24.8 (1C), 25.4 (1C), 27.9 (1C), 29.9 (1C), 32.0 (1C), 32.7 (1C), 36.9 (1C), 37.3 (1C), 39.3 (1C), 70.3 (2C), 98.8 (1C), 124.6 (1C), 135.7 (1C) ppm.

MS (EI, m/z): 352 (M$^+$, 3), 337 [(M-CH$_3$)$^+$, 9), 265 (6), 129 (100), 95 (10), 69 (24), 43 (25).

IR (cm$^{-1}$): 2953 (s), 2926 (s), 2860 (m), 1463 (m), 1394 (w), 1371 (m), 1270 (w), 1250 (w), 1211 (m), 1188 (w), 1117 (s), 1086 (s), 1043 (m), 1022 (w), 951 (w), 925 (w), 907 (w), 855 (m), 792 (w), 737 (w), 667 (w).

Experiment E6b

Asymmetric Hydrogenations of Ketals of (R,E)-6,10,14-trimethylpentadec-5-en-2-one and (R,Z)-6,10,14-trimethylpentadec-5-en-2-one An autoclave was charged with 0.5 mmol of ketals of (R,E)-6,10,14-trimethylpentadec-5-en-2-one and (R,Z)-6,10,14-trimethylpentadec-5-en-2-one as indicated in tables 3b and 3c, and with 4 g of the solvent as indicated in tables 3b and 3c and a solution of the chiral iridium complex of formula (III-F) having the chirality given in tables 3b and 3c at the centre indicated by * in said formula in the amount indicated in tables 3b and 3c. The autoclave was closed and a pressure of 30 bar of molecular hydrogen was applied. The reaction mixture was stirred for 16 hours at room temperature. Afterwards the pressure was released and the solvent was removed.

Hydrogenation of (R,E)-6,10,14-trimethyl-2,2-bis(2,2,2-trifluoroethoxy)pentadec-5-ene yielded (6R,10R)-6,10,14-trimethyl-2,2-bis(2,2,2-trifluoroethoxy)pentadecane using the Ir complex of formula (III-F) of the S configuration at the chiral centre marked by *.

The characterization of the hydrogenated ketals is given hereafter.

TABLE 3b

Asymmetric hydrogenation of different ketals of (R,E)-6,10,14-trimethylpentadec-5-en-2-one leading to (6R,10R)-6,10,14-trimethylpentadecan-2-one.

| | 63 | 64 | 65 |
|---|---|---|---|
| Ketal to be hydrogenated | R-E-THFA-DM | R-E-THFA-DM | R-E-THFA-neo |
| Formula of Ir complex | III-F | III-F | III-F |
| Configuration of chiral Ir complex at * | (S) | (S) | (S) |
| Amount of chiral Ir complex [mol-%] | 0.25 | 0.25 | 0.5 |
| Solvent[1] | DCM | TFE | DCM |
| Conversion [%] | >99 | >99 | >99 |
| Isomer-Distribution[2,3] | | | |
| (RR) [%] | 90.0 | 88.7 | 90.6 |
| ((SS) + (RS)) [%] | 8.0 | 8.7 | 9.4 |
| (SR) [%] | 2.0 | 2.6 | 0.0 |

Conditions: 0.5 mmol ketal, 4 g solvent, pressure p(H$_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal TABLE 3c Asymmetric hydrogenation of different ketals of (R,Z)-6,10,14-trimethylpentadec-5-en-2-one leading to (6R,10R)-6,10,14-trimethylpentadecan-2-one.

| | 66 | 67 | 68 | 69 |
|---|---|---|---|---|
| Ketal to be hydrogenated | R-Z-THFA-DM | R-Z-THFA-DM | R-Z-THFA-neo | R-Z-THFA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.5 | 0.5 | 0.5 |
| Solvent[1] | DCM | TFE | DCM | TFE |
| Conversion [%] | >99 | >99 | >99 | >99 |
| Isomer-Distribution[2,3] | | | | |
| (RR) [%] | 86.3 | 87.4 | 86.8 | 85.5 |
| ((SS) + (RS)) [%] | 8.2 | 7.5 | 8.2 | 9.4 |
| (SR) [%] | 5.5 | 5.1 | 5.0 | 5.1 |

Conditions: 0.5 mmol ketal, 4 g solvent, pressure p(H$_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal.

Characterization Data (6R,10R)-2,2-dimethoxy-6,10,14-trimethylpentadecane (RR18-DM)

$^1$H NMR (300 MHz, CDCl$_3$): δ 0.83-0.80 (m, 12H), 0.98-1.45 (m, 21H), 1.46-1.65 (m, 3H), 3.18 (s, 6H).

$^{13}$C NMR (75 MHz, CDCl$_3$): δ 19.68 (1C), 19.73 (1C), 21.0 (1C), 21.7 (1C), 22.6 (1C), 22.7 (1C), 24.5 (1C), 24.8 (1C), 28.0 (1C), 32.72 (1C), 32.78 (1C), 36.8 (1C), 37.28 (1C), 37.33 (1C), 37.36 (1C), 37.41 (1C), 39.4 (1C), 48.0 (2C), 101.7 (1C) ppm.

IR (cm$^{-1}$): 2951 (s), 2926 (s), 2869 (s), 2828 (m), 1734 (w), 1723 (w), 1216 (w), 1463 (s), 1377 (s), 1308 (w), 1255 (m), 1215 (m), 1172 (s), 1105 (s), 1090 (s), 1054 (s), 971 (w), 933 (w), 860 (s), 815 (m), 736 (w) 618 (w).

2,5,5-trimethyl-2-((4R,8R)-4,8,12-trimethyltridecyl)-1,3-dioxane (RR18-neo)

$^1$H NMR (300 MHz, CDCl$_3$): δ 0.78-0.95 (m, 15H), 0.95-1.61 (m, 19H), superimposed by 1.01 (s, 3H), 1.36 (s, 3H), 1.63-1.74 (m, 2H), AB signal ($\delta_A$=3.44, $\delta_B$=3.55, $J_{AB}$=11.7 Hz, 4H) ppm.

$^{13}$C NMR (75 MHz, CDCl$_3$): δ 19.72 (1C), 19.74 (1C), 20.4 (1C), 20.9 (1C), 22.56 (1C), 22.62 (1C), 22.72 (1C), 22.77 (1C), 24.5 (1C), 24.8 (1C), 28.0 (1C), 30.0 (1C), 32.8 (1C), 32.8 (1C), 37.28 (1C), 37.35 (1C), 37.42 (2C), 38.2 (1C), 39.4 (1C), 70.3 (2C), 99.1 (1C) ppm.

MS (EI, m/z): 339 [(M-CH$_3$)$^+$, 83], 269 (5), 129 (100), 69 (21), 43 (18).

IR (cm$^{-1}$): 2952 (s), 2925 (s), 2867 (m), 1463 (m), 1394 (m), 1372 (m), 1258 (m), 1211 (m), 1189 (w), 1141 (w), 1100 (s), 1043 (m), 1020 (m), 951 (w), 925 (w), 907 (m), 858 (m), 792 (w), 737 (w), 677 (w).

(6R,10R)-6,10,14-trimethyl-2,2-bis(2,2,2-trifluoroethoxy)pentadecane (RR18-tfe)

$^1$H NMR (600 MHz, CDCl$_3$): δ 0.86 (d, J=6.6 Hz, 3H), 0.879 (d, J=6.6 Hz, 3H), 0.882 (d, J=6.6 Hz, 3H), 0.884 (d,

J=6.6 Hz, 3H), 1.03-1.46 (m, 18H), superimposed by 1.40 (s, 3H), 1.54 (qqt, J=6.6, 6.6, 6.6 Hz, 1H), 1.60-1.70 (m, 2H), 3.77-3.90 (m, 4H) ppm.

$^{13}C$ NMR (151 MHz, CDCl$_3$): δ 19.6 (1C), 19.7 (1C), 21.4 (1C), 21.5 (1C), 22.6 (1C), 22.7 (1C), 24.5 (1C), 24.8 (1C), 28.0 (1C), 32.6 (1C), 32.8 (1C), 37.0 (1C), 37.24 (1C), 37.30 (1C), 37.34 (1C), 37.43 (1C), 39.4 (1C), 59.2 (q, $^2J_{C,F}$=35.0 Hz, 2C), 103.6 (1C), 124.0 (q, $^1J_{C,F}$=277.0 Hz, 2C) ppm.

MS (EI, m/z): 435 [(M-CH$_3$)$^+$, 1], 351 (1), 250 (1), 225 [(CF$_3$CH$_2$O)$_2$C—CH$_3$)$^+$, 100], 153 (7), 140 (5), 83 (CF$_3$CH$_2$$^+$, 3), 43 (6).

IR (cm$^{-1}$): 2954 (m), 2927 (m), 2871 (w), 1463 (w), 1419 (w), 1384 (w), 1281 (s), 1215 (w), 1157 (s), 1123 (m), 1082 (s), 972 (s), 892 (m), 861 (w), 737 (w), 679 (w), 663 (m).

Experiment E6c

Hydrolysis of Hydrogenated Ketals of (R,E)-6,10,14-trimethylpentadec-5-en-2-one and (R,Z)-6,10,14-trimethylpentadec-5-en-2-one After the asymmetric hydrogenation of the corresponding ketals of (R,E)-6,10,14-trimethylpentadec-5-en-2-one and (R,Z)-6,10,14-trimethylpentadec-5-en-2-one, the hydrogenated ketals obtained were hydrolyzed to the ketone and yielded (6R,10R)-6,10,14-trimethylpentadecan-2-one.

The hydrogenated ketals have been hydrolyzed as described in Experiment E2c

Formation of (R,R)-isophytol

Experiment E6-I

Ethynylation of (6R,10R)-6,10,14-trimethylpentadecan-2-one (Step g)

(6R,10R)-6,10,14-trimethylpentadecan-2-one (35.0 g, 129 mmol, 1.0 eq., 98.8%) was added to an autoclave equipped with thermostat, dosing pump, acetylene inlet and ammonia inlet. The reactor was sealed, evacuated, then flushed with nitrogen and cooled to 15° C. Ammonia (715 g, 45.0 mol, 326 eq., 99.8%) was condensed into the reactor and cooled to 15° C., resulting in a pressure of 8-9 bar. Acetylene was introduced until 12 bar was reached, followed by a dosed addition of KOH (40 wt % in water, 5.0 g, 35.6 mmol, 28 mol %) at 15° C. The reaction progress was monitored by GC. At the desired conversion (after approx. 2 h), the reaction mixture was neutralized with acetic acid, and the reactor was subsequently vented at 25° C. The reaction mixture was washed and concentrated in vacuo and purified by distillation in vacuo furnishing 26.9 g (7R,11R)-3,7,11,15-tetramethylhexadec-1-yn-3-ol with a purity of 98.8 area % (70% yield).

Experiment E6-II

Hydrogenation of (6R,10R)-6,10,14-trimethylpentadecan-2-one in the Presence of a Lindlar Catalyst (Step h)

(7R,11R)-3,7,11,15-tetramethylhexadec-1-yn-3-ol (10 g, 33.4 mmol, 98.4% purity), dissolved in heptane (40 g) and Lindlar catalyst (850 mg) were placed into an autoclave. The reactor was sealed, flushed with nitrogen and subsequently heated to 85° C. When the desired temperature was reached, the reaction was pressurized with 2 bar hydrogen. The reaction was stirred for approximately 22 hours at this temperature until the required amount of hydrogen gas was consumed. After filtration, the crude product was combined with a second reaction batch. 11.9 g of the crude material was purified by distillation, furnishing 11.1 g of (R,R)-isophytol (97.6% purity by GC, 88% overall yield).

Experiment E6-III

Vinylation of (6R,10R)-6,10,14-trimethylpentadecan-2-one (Step h')

A dried 100 mL four-necked flask equipped with overhead stirrer, thermometer, condenser and argon inlet was evacuated and purged with argon. Vinylmagnesium chloride (18.3 mL of a 1.6 M solution in THF, 29.0 mmol, 1.59 eq.) was added at room temperature. A solution of (6R,10R)-6,10,14-trimethylpentadecan-2-one (5.00 g, 18.3 mmol, 98.2%, 1.0 eq.) in dry THF (20 mL) was added slowly within 25 min. The exothermic reaction was maintained between 25 and 30° C. internal temperature by cooling with an ice bath. After complete addition the reaction was allowed to stir at room temperature for 1 h. Saturated NH$_4$Cl solution (10 mL) was added carefully to quench excess Grignard reagent. Pentane (150 mL), water (150 mL) and brine (150 mL) was added. The organic phase was extracted with brine (2×150 mL) and the aqueous phase was back-extracted with pentane (2×150 mL). The combined organic phases were dried (MgSO$_4$) and concentrated in vacuo, resulting in a colorless oil (5.58 g). The crude product was purified by vacuum distillation in a Kugelrohr apparatus. The main fraction distilled at 143° C./3.5×10$^{-2}$ mbar, furnishing (R,R)-isophytol (=(7R,11R)-3,7,11,15-tetramethylhexadec-1-en-3-ol) as colorless oil with a purity of 99.3% (5.271 g, 96% yield).

Experiment E7

Formation of (2-ambo)-α-tocopherol (Step m)

(R,R)-isophytol (=(7R,11R)-3,7,11,15-tetramethylhexadec-1-en-3-ol) was condensed with 2,3,5-trimethylbenzene-1,4-diol (=2,3,5-trimethylhydroquinone) in the presence of a condensation catalyst to (2-ambo)-α-tocopherol according to the procedure disclosed in WO 2005/121115 A1.

Experiment E8

Formation of (2R,4'R,8'R)-α-tocopherol (Step n)

As shown in FIG. 7, (2-ambo)-α-tocopherol was separated by means of chromatographic separation using a chiral phase. The preparative chromatography yielded (2R,4'R,8'R)-α-tocopherol and (2S,4'R,8'R)-α-tocopherol:

The (2-ambo)-α-tocopherol of experiment E7 was analyzed by HPLC (Column: Daicel Chiracel® OD-H, 250 mm×4.6 mm; eluent 0.5% ethanol in n-heptane; flow 1 ml/min; detection 220 nm, 2 μl injection. FIG. 7b) shows this chromatogram (Retention time 7.2 resp. 8.2 min, 50.2:49.2).

A solution of 140 mg (2-ambo)-α-tocopherol in heptane was injected and two peaks with retention time at maximum of 13.4 min (1) (50.1%) and 15.0 min (2) (49.9%) were separated by the preparative HPLC separation. FIG. 7a) shows the chromatogram of the preparative HPLC separation.

After evaporation to dryness and dissolution the two collected fractions have been reanalysed on an analytical column (Daicel Chiracel® OD-H, 250 mm×4.6 mm; eluent 0.5% ethanol in n-heptane; flow 1 ml/min; detection 220 nm, 2 μl injection). FIG. 7c), respectively FIG. 7d), show the chromatogram of the first fraction, respectively the second fraction. The isomeric ratios of the two isomers (Retention time 7.2 min, resp. 8.2 min) in said fractions are 99.5:0.5 (FIG. 7c)) and 0.8:99.2 (FIG. 7d), respectively. Hence, the two isomers have been separation by preparative chromatography almost completely.

The isomers have been identified to be (2R,4'R,8'R)-α-tocopherol (retention time 7.2 min) and (2S,4'R,8'R)-α-tocopherol (retention time 8.2 min).

Experimental Details for Chromatography of Experiment E8:

Preparative separations were performed on an Agilent 1100 series HPLC system consisting of an Agilent 1100 degasser, Agilent 1100 preparative pump. Agilent 1100 diode array detector. Agilent 1100 MPS G2250A autosampler/fraction collector controlled by chemstation/CC-mode software package.

HPLC Conditions for Preparative Separation:

Column: Daicel Chiracel® OD-H, 250 mm×20 mm; eluent 0.5% isopropanol, 0.2% acetic acid in n-heptane; flow 13 ml/min; detection 220 nm, 400 μl injection.

The invention claimed is:

1. A process of manufacturing (6R,10R)-6,10,14-trimethylpentadecan-2-one in a multistep synthesis from 6,10-dimethylundec-5-en-2-one or 6,10-dimethylundeca-5,9-dien-2-one comprising the sequential steps of:
   a) providing a mixture of (E)-6,10-dimethylundec-5-en-2-one and (Z)-6,10-dimethylundec-5-en-2-one or a mixture of (E)-6,10-dimethylundeca-5,9-dien-2-one and (Z)-6,10-dimethylundeca-5,9-dien-2-one;
   b) separating one isomer of 6,10-dimethylundec-5-en-2-one or of 6,10-dimethylundeca-5,9-dien-2-one from the mixture of step a);
   c) conducting asymmetric hydrogenation using molecular hydrogen in the presence of a chiral iridium complex and yielding (R)-6,10-dimethylundecan-2-one;
   d) chemically transforming (R)-6,10-dimethylundecan-2-one to a mixture of (R,E)-6,10,14-trimethylpentadec-5-en-2-one and (R,Z)-6,10,14-trimethylpentadec-5-en-2-one;
   e) separating one isomer of (R)-6,10,14-trimethylpentadec-5-en-2-one from the mixture obtained in step d); and
   f) conducting asymmetric hydrogenation using molecular hydrogen in the presence of a chiral iridium complex and yielding (6R,10R)-6,10,14-trimethylpentadecan-2-one, wherein
step d) is practiced by:
   d1) ethynylation of (R)-6,10-dimethylundecan-2-one using ethyne in the presence of a basic substance to yield (7R)-3,7,11-trimethyldodec-1-yn-3-ol; and
   d2) hydrogenation of (7R)-3,7,11-trimethyldodec-1-yn-3-ol with molecular hydrogen in the presence of a Lindlar catalyst to yield (7R)-3,7,11-trimethyldodec-1-en-3-ol;
or step d) is practiced by:
   d1') vinylation of (R)-6,10-dimethylundecan-2-one by addition of a vinyl Grignard reagent to yield (7R)-3,7,11-trimethyldodec-1-en-3-ol;
followed by either
   d3) reacting (7R)-3,7,11-trimethyldodec-1-en-3-ol with 2-methoxyprop-1-ene to yield a mixture of (R,E)-6,10,14-trimethylpentadec-5-en-2-one and (R,Z)-6,10,14-trimethylpentadec-5-en-2-one;
or
   d3') reacting (7R)-3,7,11-trimethyldodec-1-en-3-ol with an alkyl acetoacetate or diketene in the presence of a base and/or an acid to yield a mixture of (R,E)-6,10,14-trimethylpentadec-5-en-2-one and (R,Z)-6,10,14-trimethylpentadec-5-en-2-one.

2. The process according to claim 1, which further comprises a step $c_o$) before step c):
   $c_o$) forming of a ketal of the isomer of 6,10-dimethylundec-5-en-2-one or of 6,10-dimethylundeca-5,9-dien-2-one separated in step b), and wherein
the ketal of 6,10-dimethylundec-5-en-2-one or of 6,10-dimethylundeca-5,9-dien-2-one in step c) is asymmetrically hydrogenated and after the asymmetric hydrogenation the hydrogenated ketal is hydrolysed to the ketone thereby yielding (R)-6,10-dimethylundecan-2-one.

3. The process according to claim 1, wherein the process further comprises a step $f_o$) before the step f) of:
   $f_o$) forming a ketal of the isomer of (R)-6,10,14-trimethylpentadec-5-en-2-one separated in step e), and wherein
step f) comprises asymmetrically hydrogenating the ketal of (R)-6,10,14-trimethylpentadec-5-en-2-one and then subsequently after the asymmetric hydrogenation, hydrolysing the hydrogenated ketal to the ketone to thereby yield (6R,10R)-6,10,14-trimethylpentadecan-2-one.

4. The process according to claim 1, wherein the asymmetric hydrogenation in step c) and/or step f) takes place in the presence of an additive which is selected from the group consisting of organic sulfonic acids, transition metal salts of organic sulfonic acids, metal alkoxides, aluminoxanes, alkyl aluminoxanes and $B(R)_{(3-v)}(OZ)_v$, wherein v stands for 0, 1, 2 or 3, R stands for F, a $C_{1-6}$-alkyl, a halogenated $C_{1-6}$-alkyl, an aryl or halogenated aryl group, and Z stands a $C_{1-6}$-alkyl, a halogenated $C_{1-6}$-alkyl, an aryl or halogenated aryl group.

5. The process according to claim 1, wherein the separation of isomers in step b) and/or e) is done by distillation.

6. The process according to claim 5, wherein the distillation is done in the presence of a cis/trans isomerization catalyst.

7. The process according to claim 1, which further comprises isomerizing residual isomer in the presence of a cis/trans isomerization catalyst, and respectively adding the isomerized residual isomer to the corresponding mixture of isomers provided by steps a) and d).

8. The process according to claim 1, wherein the chiral iridium complex in steps c) and/or f) is a chiral iridium complex of formula (III-0)

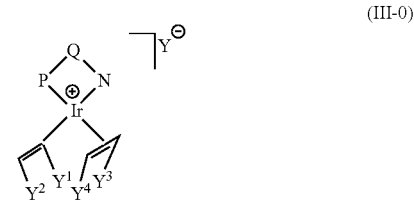

(III-0)

wherein
P-Q-N stands for a chelating organic ligand comprising a stereogenic centre or has planar or axial chirality and has a nitrogen and phosphorous atom as binding site to the iridium centre of the complex;

$Y^1$, $Y^2$, $Y^3$ and $Y^4$ independently from each other are hydrogen atoms, $C_{1-12}$-alkyl, $C_{5-10}$-cycloalkyl, or aromatic group; or at least two of $Y^1$, $Y^2$, $Y^3$ and $Y^4$ form together at least a two-valent bridged group of at least 2 carbon atoms; with the proviso that $Y^1$, $Y^2$, $Y^3$ and $Y^4$ are not all hydrogen atoms; and $Y^\ominus$ is an anion selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$.

9. The process according to claim 1, wherein the chiral iridium complex in steps c) and/or f) is a chiral iridium complex of formula (III)

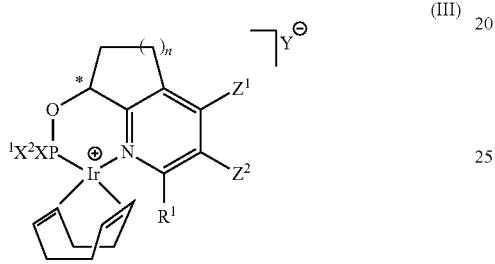

(III)

wherein n is 1, 2 or 3;

$X^1$ and $X^2$ are independently from each other hydrogen atoms, $C_{1-4}$-alkyl, $C_{5-7}$-cycloalkyl, adamantyl, phenyl optionally substituted with one to three $C_{1-5}$-alkyl, $C_{1-4}$-alkoxy, $C_{1-4}$-perfluoroalkyl groups and/or one to five halogen atoms, benzyl, 1-naphthyl, 2-naphthyl, 2-furyl or ferrocenyl;

$Z^1$ and $Z^2$ are independently from each other hydrogen atoms, $C_{1-5}$-alkyl or $C_{1-5}$-alkoxy groups or $Z^1$ and $Z^2$ stand together for a bridging group forming a 5 to 6 membered ring;

$Y^\ominus$ is an anion selected from the group consisting of halide, $PF_6^-$, $SbF_6^-$, tetra(3,5-bis(trifluoromethyl)phenyl)borate($BAr_F^-$), $BF_4^-$, perfluorinated sulfonates, $ClO_4^-$, $Al(OC_6F_6)_4^-$, $Al(OC(CF_3)_3)_4^-$, $N(SO_2CF_3)_2^-N(SO_2C_4F_9)_2^-$ and $B(C_6F_6)_4^-$;

$R^1$ represents either phenyl or o-tolyl or m-tolyl or p-tolyl or a group of formula (IVa) or (IVb) or (IVc):

(IVa)

(IVb)

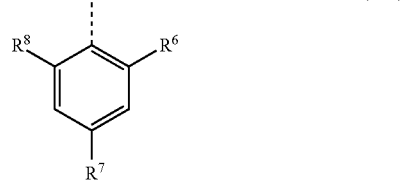

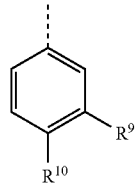

(IVc)

wherein $R^2$ and $R^3$ represent either both H or a $C_{1-4}$-alkyl group or a halogenated $C_{1-4}$-alkyl group or represent a divalent group forming together a 6-membered cycloaliphatic or an aromatic ring which optionally is substituted by halogen atoms or by $C_{1-4}$-alkyl groups or by $C_{1-4}$-alkoxy groups;

$R^4$ and $R^5$ represent either both H or a $C_{1-4}$-alkyl group or a halogenated $C_{1-4}$-alkyl group or a divalent group forming together a 6-membered cycloaliphatic or an aromatic ring which optionally is substituted by halogen atoms or by $C_{1-4}$-alkyl groups or by $C_{1-4}$-alkoxy groups;

$R^6$ and $R^7$ and $R^8$ represent each a $C_{1-4}$-alkyl group or a halogenated $C_{1-4}$-alkyl group;

$R^9$ and $R^{19}$ represent either both H or a $C_{1-4}$-alkyl group or a halogenated $C_{1-4}$-alkyl group or a divalent group forming together a 6-membered cycloaliphatic or an aromatic ring which optionally is substituted by halogen atoms or by $C_{1-4}$-alkyl groups or by $C_{1-4}$-alkoxy groups; and wherein the symbol * represents a stereogenic centre of the complex of formula (III).

10. The process according to claim 9, wherein the chiral iridium complex of formula (III) used in step c) and/or f) for the asymmetric hydrogenation has the S-configuration at the stereogenic centre indicated by the symbol * in case (E)-6,10-dimethylundec-5-en-2-one or (E)-6,10-dimethylundeca-5,9-dien-2-one, or ketals thereof, or (R,E)-6,10,14-trimethylpentadec-5-en-2-one, or ketals thereof, are to be hydrogenated; or the chiral iridium complex of formula (III) used in step c) and/or f) for the asymmetric hydrogenation has the R-configuration at the stereogenic centre indicated by the symbol * in case (Z)-6,10-dimethylundec-5-en-2-one or (Z)-6,10-dimethylundeca-5,9-dien-2-one, or ketals thereof, or (R,Z)-6,10,14-trimethylpentadec-5-en-2-one, or ketals thereof, are to be hydrogenated.

11. A process of manufacturing (R,R)-isophytol ((3RS,7R,11R)-3,7,11,15-tetramethylhexadec-1-en-3-ol) comprising manufacturing (6R,10R)-6,10,14-trimethylpentadecan-2-one according to claim 1, followed by the steps of:

g) ethynylation of (6R,10R)-6,10,14-trimethylpentadecan-2-one using ethyne in the presence of a basic substance to yield (7R,11R)-3,7,11,15-tetramethylhexadec-1-yn-3-ol; and either h) hydrogenation of (7R,11R)-3,7,11,15-tetramethylhexadec-1-yn-3-ol with molecular hydrogen in the presence of a Lindlar catalyst to yield (R,R)-isophytol; or h') vinylation of (6R,10R)-6,10,14-trimethylpentadecan-2-one by addition of a vinyl Grignard reagent to yield (R,R)-isophytol.

12. A process of manufacturing compound of formula (V) comprising manufacturing (6R,10R)-6,10,14-trimethylpentadecan-2-one according to 1, followed by the steps of:

g) ethynylation of (6R,10R)-6,10,14-trimethylpentadecan-2-one using ethyne in the presence of a basic substance to yield (7R,11R)-3,7,11,15-tetramethylhexadec-1-yn-3-ol; and either h) hydrogenation of (7R,11R)-3,7,11,15-tetramethylhexadec-1-yn-3-ol with molecular hydrogen in the presence of a Lindlar catalyst to yield (R,R)-isophytol; or h') vinylation of (6R,10R)-6,10,14-trimethylpentadecan-2-one by addition of a vinyl Grignard reagent to yield (R,R)-isophytol; and then subsequently followed by the step of:

m) condensing (R,R)-isophytol with a compound of formula (VI) to yield the compound of formula (V) being an isomeric mixture in view of the chirality at the centre indicated by the symbol #;

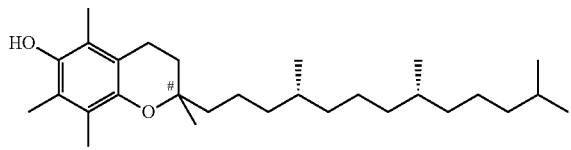
(V)

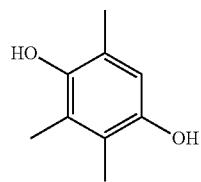
(VI)

and wherein the symbol # represents a stereogenic centre.

13. A process of manufacturing compound of formula (V-A) comprising manufacturing (6R,10R)-6,10,14-trimethylpentadecan-2-one according to claim 1, followed by the steps of:

g) ethynylation of (6R,10R)-6,10,14-trimethylpentadecan-2-one using ethyne in the presence of a basic substance to yield (7R,11R)-3,7,11,15-tetramethylhexadec-1-yn-3-ol; and either h) hydrogenation of (7R,11R)-3,7,11,15-tetramethylhexadec-1-yn-3-ol with molecular hydrogen in the presence of a Lindlar catalyst to yield (R,R)-isophytol; or h') vinylation of (6R,10R)-6,10,14-trimethylpentadecan-2-one by addition of a vinyl Grignard reagent to yield (R,R)-isophytol; and then subsequently followed by the steps of:

m) condensing (R,R)-isophytol with compound of formula (VI) to yield compound of formula (V) being an isomeric mixture in view of the chirality at the centre indicated by the symbol #;

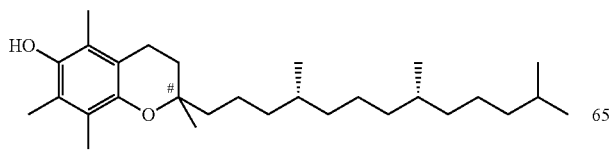
(V)

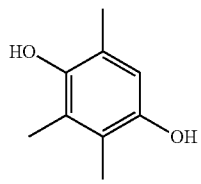
(VI)

wherein $R^{11}$, $R^{13}$ and $R^{14}$ are independently from each other hydrogen or methyl groups; and wherein the symbol # represents a stereogenic centre; and n) isolating the compound of formula (V-A) from the isomeric mixture of formula (V)

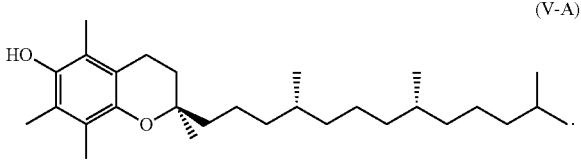 [SMILES: Cc1c(C)c2c(c(C)c1O)CC[C@@](C)(CCC[C@H](C)CCC[C@H](C)CCCC(C)C)O2]
(V-A)

14. A composition comprising:
at least one ketal of formula (XI) or (XII); and
at least one chiral iridium complex,

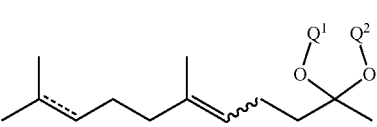
(XI)

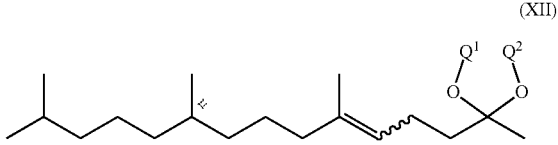
(XII)

wherein a wavy line represents a carbon-carbon bond which is linked to the adjacent carbon-carbon double bond so as to have the carbon-carbon double bond either in the Z or in the E-configuration; and wherein the double bond having dotted lines ===== in formula (XI) represent either a single carbon-carbon bond or a double carbon-carbon bond; and wherein
the symbol ✧ represents a stereogenic centre; and wherein
$Q^1$ and $Q^2$ stand either individually or both for a $C_1$-$C_{10}$ alkyl group or a halogenated $C_1$-$C_{10}$ alkyl group; or $Q^1$ and $Q^2$ form together a $C_2$-$C_6$ alkylene group or a $C_6$-$C_8$ cycloalkylene group.

15. A ketal of formula (XX-A), (XX-B), (XX-C) or (XX-D):

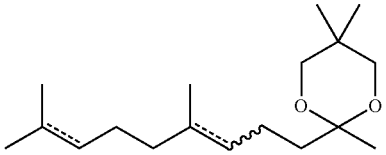
(XX-A)

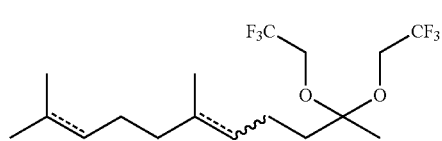
(XX-B)

-continued

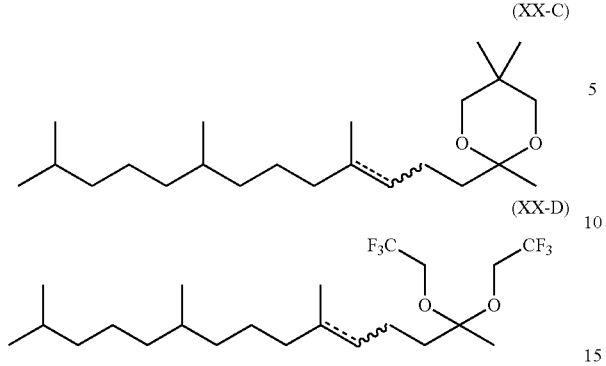

(XX-C)

(XX-D)

wherein the double bond having dotted lines (=====) in the above formulae represents either a single carbon-carbon bond or a double carbon-carbon bond; and wherein a wavy line represents a carbon-carbon bond which is linked to an adjacent single carbon bond (===== representing—) or to an adjacent carbon-carbon double bond (===== representing=) so as to have the carbon-carbon double bond either in the Z or in the E-configuration.

16. The process according to claim 8, wherein $Y^O$ is $F_3C-SO_3^-$ or $F_9C_4-SO_3^-$.

17. The process according to claim 9, wherein $Y^O$ is $F_3C-SO_3^-$ or $F_9C_4-SO_3^-$.

* * * * *